United States Patent
Gourlay et al.

(10) Patent No.: US 12,178,818 B2
(45) Date of Patent: Dec. 31, 2024

(54) METHODS FOR TREATING IMMUNE THROMBOCYTOPENIA BY ADMINISTERING (R)-2-[3-[4-AMINO-3-(2-FLUORO-4-PHENOXY-PHENYL)PYRAZOLO[3,4-D]PYRIMIDIN-1-YL]PIPERIDINE-1-CARBONYL]-4-METHYL-4-[4-(OXETAN-3-YL)PIPERAZIN-1-YL]PENT-2-ENENITRILE

(71) Applicant: Principia Biopharma Inc., Bridgewater, NJ (US)

(72) Inventors: Steven Gourlay, Queens Park (AU); Ann Neale, Danville, CA (US); Philip Nunn, Mountain View, CA (US); Claire Langrish, Redwood City, CA (US); Olga Bandman, Mountain View, CA (US); Dolca Thomas, San Francisco, CA (US)

(73) Assignee: Principia Biopharma Inc., Bridgewater, NJ (US)

( * ) Notice: Subject to any disclaimer, the term of this patent is extended or adjusted under 35 U.S.C. 154(b) by 0 days.

(21) Appl. No.: 17/946,585

(22) Filed: Sep. 16, 2022

(65) Prior Publication Data
US 2023/0124267 A1  Apr. 20, 2023

Related U.S. Application Data

(63) Continuation of application No. 17/069,218, filed on Oct. 13, 2020, now abandoned.
(Continued)

(51) Int. Cl.
*A61K 31/519* (2006.01)
*A61K 9/00* (2006.01)
(Continued)

(52) U.S. Cl.
CPC .......... *A61K 31/519* (2013.01); *A61K 9/0053* (2013.01); *A61K 9/28* (2013.01); *A61P 7/00* (2018.01); *A61K 45/06* (2013.01)

(58) Field of Classification Search
CPC ...... A61K 31/519; A61K 9/0053; A61K 9/28; A61K 45/06; A61P 7/00
See application file for complete search history.

(56) References Cited

U.S. PATENT DOCUMENTS

| 4,721,710 A | 1/1988 | Bernhart et al. |
| 4,861,760 A | 8/1989 | Mazuel et al. |

(Continued)

FOREIGN PATENT DOCUMENTS

| CA | 2890111 A1 | 5/2014 |
| CN | 1274280 A | 11/2000 |

(Continued)

OTHER PUBLICATIONS

Bussel et al., Blood, vol. 118(1), pp. 28-36, publ. 2011 (Year: 2011).*

(Continued)

*Primary Examiner* — Sarah Pihonak
(74) *Attorney, Agent, or Firm* — McNeill PLLC

(57) ABSTRACT

Methods for treating immune thrombocytopenia comprising administering at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof are disclosed. Pharmaceutical compositions comprising at least one compound chosen from PRN1008 and pharmaceutically acceptable salts thereof are also disclosed.

22 Claims, 10 Drawing Sheets

Related U.S. Application Data

(60) Provisional application No. 62/951,302, filed on Dec. 20, 2019, provisional application No. 62/914,688, filed on Oct. 14, 2019.

(51) Int. Cl.
  *A61K 9/28* (2006.01)
  *A61K 45/06* (2006.01)
  *A61P 7/00* (2006.01)

(56) References Cited

U.S. PATENT DOCUMENTS

| | | |
|---|---|---|
| 4,911,920 A | 3/1990 | Jani et al. |
| 5,212,162 A | 5/1993 | Missel et al. |
| 5,403,841 A | 4/1995 | Lang et al. |
| 5,514,711 A | 5/1996 | Kitano et al. |
| 5,792,771 A | 8/1998 | App et al. |
| 6,331,555 B1 | 12/2001 | Hirth et al. |
| 6,410,486 B2 | 6/2002 | Wetterich et al. |
| 6,596,746 B1 | 7/2003 | Das et al. |
| 6,660,744 B1 | 12/2003 | Hirst et al. |
| 7,217,682 B2 | 5/2007 | Mori |
| 7,514,444 B2 | 4/2009 | Honigberg et al. |
| 7,700,648 B2 | 4/2010 | Mori |
| 8,673,925 B1 | 3/2014 | Goldstein |
| 8,759,358 B1 | 6/2014 | Goldstein |
| 8,828,426 B2 | 9/2014 | Shah et al. |
| 8,940,744 B2 | 1/2015 | Owens et al. |
| 8,946,241 B2 | 2/2015 | Goldstein |
| 8,957,080 B2 | 2/2015 | Goldstein et al. |
| 8,962,635 B2 | 2/2015 | Goldstein |
| 8,962,831 B2 | 2/2015 | Goldstein |
| 9,090,621 B2 | 7/2015 | Goldstein |
| 9,266,895 B2 | 2/2016 | Owens et al. |
| 9,376,438 B2 | 6/2016 | Goldstein et al. |
| 9,572,811 B2 | 2/2017 | Babler et al. |
| 9,688,676 B2 | 6/2017 | Owens |
| 9,994,576 B2 | 6/2018 | Owens et al. |
| 10,092,569 B2 | 10/2018 | Masjedizadeh et al. |
| 10,456,403 B2 | 10/2019 | Masjedizadeh et al. |
| 10,485,797 B2 | 11/2019 | Gourlay |
| 10,533,013 B2 | 1/2020 | Owens et al. |
| 11,040,980 B2 | 6/2021 | Owens et al. |
| 2003/0153752 A1 | 8/2003 | Hirst et al. |
| 2003/0187001 A1 | 10/2003 | Calderwood et al. |
| 2004/0006083 A1 | 1/2004 | Hirst et al. |
| 2004/0157847 A1 | 8/2004 | Field et al. |
| 2005/0008640 A1 | 1/2005 | Waegell et al. |
| 2005/0026945 A1 | 2/2005 | Kafka et al. |
| 2005/0065176 A1 | 3/2005 | Field et al. |
| 2006/0025383 A1 | 2/2006 | Wishart et al. |
| 2006/0058297 A1 | 3/2006 | Roifman et al. |
| 2006/0058324 A1 | 3/2006 | Capraro et al. |
| 2006/0079494 A1 | 4/2006 | Santi et al. |
| 2006/0275376 A1 | 12/2006 | Guimberteau et al. |
| 2007/0149464 A1 | 6/2007 | Billen et al. |
| 2007/0149550 A1 | 6/2007 | Billen et al. |
| 2007/0232668 A1 | 10/2007 | Priebe et al. |
| 2007/0232688 A1 | 10/2007 | Orchansky et al. |
| 2008/0076921 A1 | 3/2008 | Honigberg et al. |
| 2008/0146643 A1 | 6/2008 | Billen et al. |
| 2008/0176865 A1 | 7/2008 | Billen et al. |
| 2008/0260818 A1 | 10/2008 | Penhasi et al. |
| 2009/0215750 A1 | 8/2009 | Bamberg et al. |
| 2009/0215788 A1 | 8/2009 | Elworthy et al. |
| 2009/0306396 A1 | 12/2009 | Toyoshima et al. |
| 2010/0113520 A1 | 5/2010 | Miller |
| 2010/0144705 A1 | 6/2010 | Miller |
| 2010/0152143 A1 | 6/2010 | Priebe et al. |
| 2010/0254905 A1 | 10/2010 | Honigberg et al. |
| 2010/0280035 A1 | 11/2010 | Becker et al. |
| 2011/0021518 A1 | 1/2011 | Magnuson et al. |
| 2011/0086866 A1 | 4/2011 | Chen et al. |
| 2012/0028981 A1 | 2/2012 | Miller |
| 2012/0071497 A1 | 3/2012 | Buggy et al. |
| 2012/0149687 A1 | 6/2012 | Lee et al. |
| 2013/0079327 A1 | 3/2013 | Yamamoto et al. |
| 2013/0197014 A1 | 8/2013 | Chen et al. |
| 2014/0094459 A1 | 4/2014 | Goldstein et al. |
| 2014/0142099 A1 | 5/2014 | Owens |
| 2014/0221398 A1 | 8/2014 | Goldstein et al. |
| 2014/0256734 A1 | 9/2014 | Lawson et al. |
| 2014/0303190 A1 | 10/2014 | Goldstein |
| 2014/0364410 A1 | 12/2014 | Owens et al. |
| 2015/0140085 A1 | 5/2015 | Goldstein |
| 2015/0209432 A1 | 7/2015 | Konda et al. |
| 2015/0328310 A1 | 11/2015 | Allen et al. |
| 2015/0353557 A1 | 12/2015 | Goldstein et al. |
| 2015/0353562 A1 | 12/2015 | Goldstein |
| 2016/0045503 A1 | 2/2016 | Goldstein et al. |
| 2016/0113913 A1 | 4/2016 | Murakawa et al. |
| 2016/0257686 A1 | 9/2016 | Owens |
| 2016/0376277 A1 | 12/2016 | Desai et al. |
| 2017/0065591 A1 | 3/2017 | Masjedizadeh et al. |
| 2018/0015088 A1 | 1/2018 | Nunn et al. |
| 2018/0162861 A1 | 6/2018 | Goldstein et al. |
| 2018/0193274 A1 | 7/2018 | Nunn et al. |
| 2018/0305350 A1 | 10/2018 | Goldstein et al. |
| 2018/0327413 A1 | 11/2018 | Owens et al. |
| 2019/0231784 A1 | 8/2019 | Ferdous et al. |
| 2019/0345159 A1 | 11/2019 | Goldstein et al. |
| 2020/0038405 A1 | 2/2020 | Masjedizadeh et al. |
| 2020/0101059 A1 | 4/2020 | Gourlay |
| 2020/0190092 A1 | 6/2020 | Owens et al. |
| 2021/0106584 A1 | 4/2021 | Gourlay et al. |
| 2021/0221818 A1 | 7/2021 | Phiasivongsa et al. |

FOREIGN PATENT DOCUMENTS

| | | |
|---|---|---|
| CN | 1681483 A | 10/2005 |
| CN | 1874761 A | 12/2006 |
| CN | 101287452 A | 10/2008 |
| CN | 101610676 A | 12/2009 |
| CN | 101730699 A | 6/2010 |
| CN | 101880243 A | 11/2010 |
| CN | 102159214 A | 8/2011 |
| CN | 101610676 B | 3/2013 |
| CN | 103096716 A | 5/2013 |
| CN | 101805341 A | 7/2013 |
| CN | 101805341 B | 7/2013 |
| CN | 103534258 A | 1/2014 |
| CN | 104640861 A | 5/2015 |
| CN | 104736178 A | 6/2015 |
| CN | 104822681 A | 8/2015 |
| CN | 103096716 B | 3/2016 |
| CN | 105753863 A | 7/2016 |
| CN | 103534258 B | 9/2016 |
| CN | 106456652 A | 2/2017 |
| CN | 110483521 A | 11/2019 |
| CN | 106456652 B | 9/2020 |
| EP | 0461546 A2 | 12/1991 |
| EP | 0493767 A2 | 7/1992 |
| EP | 0461546 A3 | 3/1993 |
| EP | 0493767 A3 | 3/1993 |
| EP | 0908457 A1 | 4/1999 |
| EP | 2443929 A1 | 4/2012 |
| EP | 2578585 A1 | 4/2013 |
| EP | 2578585 B1 | 7/2016 |
| FR | 2535721 A1 | 5/1984 |
| GB | 2447933 A | 10/2008 |
| JP | 5663950 A | 5/1981 |
| JP | 021450 A | 1/1990 |
| JP | 04177244 A | 6/1992 |
| JP | 2005239657 A | 9/2005 |
| JP | 2010504324 A | 2/2010 |
| JP | 2010235628 A | 10/2010 |
| JP | 2014513729 A | 6/2014 |
| JP | 2014517838 A | 7/2014 |
| JP | 2015522653 A | 8/2015 |
| JP | 2016503063 A | 2/2016 |
| JP | 6203848 B2 | 9/2017 |
| WO | 9524190 A2 | 9/1995 |
| WO | 9531432 A1 | 11/1995 |

(56) References Cited

FOREIGN PATENT DOCUMENTS

| | | |
|---|---|---|
| WO | 9841499 A1 | 9/1998 |
| WO | 9914216 A1 | 3/1999 |
| WO | 9918938 A1 | 4/1999 |
| WO | 0172751 A1 | 10/2001 |
| WO | 02066463 A1 | 8/2002 |
| WO | 03037890 A2 | 5/2003 |
| WO | 03050080 A1 | 6/2003 |
| WO | 03068157 A2 | 8/2003 |
| WO | 03082807 A2 | 10/2003 |
| WO | 2004016259 A1 | 2/2004 |
| WO | 2004074283 A1 | 9/2004 |
| WO | 2005020929 A2 | 3/2005 |
| WO | 2005023773 A1 | 3/2005 |
| WO | 2005030184 A2 | 4/2005 |
| WO | 2005085210 A1 | 9/2005 |
| WO | 2006086634 A2 | 8/2006 |
| WO | 2006134468 A1 | 12/2006 |
| WO | 2007043401 A1 | 4/2007 |
| WO | 2007087068 A2 | 8/2007 |
| WO | 2007130075 A1 | 11/2007 |
| WO | 2007142755 A2 | 12/2007 |
| WO | 2008005954 A2 | 1/2008 |
| WO | 2008006032 A1 | 1/2008 |
| WO | 2007087068 A3 | 2/2008 |
| WO | 2008039218 A2 | 4/2008 |
| WO | 2008054827 A2 | 5/2008 |
| WO | 2008061740 A1 | 5/2008 |
| WO | 2008072053 A2 | 6/2008 |
| WO | 2008072077 A2 | 6/2008 |
| WO | 2008116064 A2 | 9/2008 |
| WO | 2008121742 A2 | 10/2008 |
| WO | 2009140128 A2 | 11/2009 |
| WO | 2009143477 A1 | 11/2009 |
| WO | 2010009342 A2 | 1/2010 |
| WO | 2010014930 A2 | 2/2010 |
| WO | 2010065898 A2 | 6/2010 |
| WO | 2011031896 A2 | 3/2011 |
| WO | 2011046964 A2 | 4/2011 |
| WO | 2011060440 A2 | 5/2011 |
| WO | 2011144585 A1 | 11/2011 |
| WO | 2011152351 A1 | 12/2011 |
| WO | 2011153514 A2 | 12/2011 |
| WO | 2012021444 A1 | 2/2012 |
| WO | 2012158764 A1 | 11/2012 |
| WO | 2012158795 A1 | 11/2012 |
| WO | 2012158810 A1 | 11/2012 |
| WO | 2012158843 A2 | 11/2012 |
| WO | 2013003629 A2 | 1/2013 |
| WO | 2013010136 A2 | 1/2013 |
| WO | 2013010380 A1 | 1/2013 |
| WO | 2013010868 A1 | 1/2013 |
| WO | 2013010869 A1 | 1/2013 |
| WO | 2013041605 A1 | 3/2013 |
| WO | 2013059738 A2 | 4/2013 |
| WO | 2013102059 A1 | 7/2013 |
| WO | 2013116382 A1 | 8/2013 |
| WO | 2013184572 A1 | 12/2013 |
| WO | 2013185082 A2 | 12/2013 |
| WO | 2013191965 A1 | 12/2013 |
| WO | 2014004707 A1 | 1/2014 |
| WO | 2014022569 A1 | 2/2014 |
| WO | 2014039899 A1 | 3/2014 |
| WO | 2014068527 A1 | 5/2014 |
| WO | 2014078578 A1 | 5/2014 |
| WO | 2014164558 A1 | 10/2014 |
| WO | 2014171542 A1 | 10/2014 |
| WO | 2015127310 A1 | 8/2015 |
| WO | 2015132799 A2 | 9/2015 |
| WO | 2016100914 A1 | 6/2016 |
| WO | 2017041536 A1 | 3/2017 |
| WO | 2017066014 A1 | 4/2017 |
| WO | 2018005849 A1 | 1/2018 |
| WO | 2019208805 A1 | 10/2019 |
| WO | 2021076514 A1 | 4/2021 |
| WO | 2022081512 A1 | 4/2022 |

OTHER PUBLICATIONS

Audia, S., et al., "Pathogenesis of immune thrombocytopenia," Autoimmunity Reviews, vol. 16, pp. 620-632, Apr. 17, 2017.
Cuker, A., et al., "How I treat refractory immune thrombocytopenia," Blood, vol. 128, No. 12, pp. 1547-1554, Sep. 22, 2016.
International Search Report for PCT/US2020/055410 mailed on Jan. 15, 2021 (5 pages).
Kuter, David J., et al., "Phase I/II, Open-Label, Adaptive Study of Oral Bruton Tyrosine Kinase Inhibitor PRN1008 in Patients with Relapsed/Refractory Primary or Secondary Immune Thrombocytopenia", Blood, vol. 134, No. Suppl. 1, Nov. 13, 2019, p. 87, 61st Annual Meeting and Exposition of the American-Society-of-Hematology (ASH), Orlando, FL, USA, Dec. 7-10, 2019.
Langrish, Claire L., et al., "PRN1008, a Reversible Covalent BTK Inhibitor in Clinical Development for Immune Thrombocytopeniarpura", Blood, vol. 130, No. Suppl. 1, Dec. 7, 2017, p. 1052, 59th Annual Meeting of the American-Society-of-Hematology (ASH), Atlanta, GA, Dec. 9-12, 2017.
Rodeghiero, Francesco, "A critical appraisal of the evidence for the role of splenectomy in adults and children with ITP", British Journal of Haematology, vol. 181, No. 2, Feb. 26, 2018, pp. 183-195.
Honigberg, L.A., et al., "The Bruton tyrosine kinase inhibitor PCT-32765 blocks B-cell activation and is efficacious in models of autoimmune disease and B-cell malignancy," PNAS, vol. 107, pp. 13075-13080 (2010).
Horvath, B., et al., "Low dose rituximab is effective in pemphigus," British Journal of Dermatology, vol. 166, No. 2, pp. 405-412 (2012).
Hutcheson, J., et al., "Modulating proximal cell signaling by targeting Btk ameliorates humoral autoimmunity and end-organ disease in murine lupus," Arthritis Research & Therapy, vol. 14, pp. R243 (2012).
Ihrke, P.J., et al., "Pemphigus foliaceus in dogs: a review of 37 cases," Journal of the American Veterinary Medical Association, vol. 186, No. 1, pp. 59-66 (1985).
Irwin, S., "Comprehensive observational assessment: Ia. A systematic, quantitative procedure for assessing the behavioral and physiologic state of the mouse," Psychopharmacologia, vol. 13, No. 3, pp. 222-257 (1968).
Ito, M., et al., "Bruton's tyrosine kinase is essential for NLRP3 inflammasome activation and contributes to ischaemic brain injury," Nature Communications, vol. 6, No. 1, p. 1 (2015).
Ivankovic, S., Fehlende teratogene Wirkung von Nitroprussidnatrium (NNP) an Wistar-Ratten und Kaninchen [Absence of a teratogenic effect of sodium nitroprusside in wistar rats and rabbits (author's transl)]. Arzneimittelforschung, vol. 29, No. 8, pp. 1092-1094 (1979).
Jager, U., et al., "Diagnosis and treatment of autoimmune hemolytic anemia in adults: Recommendations from the First International Consensus Meeting," Blood Review, vol. 41, p. 100648 (2020).
Joly, P., et al., "First-line rituximab combined with short-term prednisone versus prednisone alone for the treatment of pemphigus (Ritux 3): a prospective, multicentre, parallel-group, open-label randomised trial," Lancet, vol. 389, No. 10083, pp. 2031-2040 (2017).
Joly, P., et al., "Pemphigus group (vulgaris, vegetans, foliaceus, herpetiformis, brasiliensis)," Clinical Dermatology, vol. 29, No. 4, pp. 432-436 (2011).
Karra, E., et al., "The role of peptide YY in appetite regulation and obesity," Journal of Physiology, vol. 587, No. 1, pp. 19-25 (2009).
Khellaf, M., et al., "Safety and efficacy of rituximab in adult immune thrombocytopenia: results from a prospective registry including 248 patients," Blood, vol. 124, No. 22, pp. 3228-3236 (2014).
Kihlman, B.A., "Experimentally Induced Chromosome Aberrations in Plants, I. The production of chromosome aberrations by cyanide and other heavy metal complexing agents," Journal of Biophysical & Biochemical Cytology, vol. 3, No. 3, pp. 363-380 (1957).
Kim, K.H., et al., "Imidazo[1.5-a]quinoxalines as irreversible BTK inhibitors for the treatment of rheumatoid arthritis," Bioorganic & Medicinal Chemical Letters, vol. 21, pp. 6258-6263 (2011).

(56) References Cited

OTHER PUBLICATIONS

Klein, N.P., et al., "Rates of autoimmune diseases in Kaiser Permanente for use in vaccine adverse event safety studies," Vaccine, vol. 28, No. 4, pp. 1062-1068 (2010).
Kohrt, H.E., et al., "Ibrutinib antagonizes rituximab-dependent NK cell-mediated cytotoxicity," Blood, vol. 123, No. 12, pp. 1957-1960 (2014).
Kridin, K., et al., "Mortality and Cause of Death in Patients with Pemphigus," Acta Dermato-Venereologica, vol. 97, No. 5, pp. 607-611 (2017).
Kuter, D.J., et al., "22 oral rilzabrutinib Bruton tyrosine kinase inhibitor, showed clinically active and durable platelet responses and was well-tolerated in patients with heavily pretreated immune thrombocytopenia," 62nd ASH Annual Meeting & Exposition, Abstract (presentation) (Dec. 5-8, 2020).
Kuter, D.J., et al., "Rilzabrutinib, an Oral BTK Inhibitor, in Immune Thrombocytopenia," MEJM Paper, vol. 386, No. 15, pp. 1421-1431 (2022).
Kuter, D.J., et al., "Safety and efficacy of rilzabrutinib (PRN1008), an oral Bruton tyrosine kinase inhibitor, in relapsed/refractory patients with primary or secondary immune thrombocytopenia: Phase I/II adaptive study," European Hematology Association (EHA) annual meeting, vol. 4, No. S1, pp. 118-119 (abstract S316) poster presentation (2020).
Langrish, C., et al., Preclinical Efficacy and Anti-Inflammatory Mechanisms of Action of the Bruton Tyrosine Kinase Inhibitor Rilzabrutinib for Immune-Mediated Disease, Journal of Immunology, vol. 206, No. 7, pp. 1454-1486 (2021).
Lindberg, H.A., et al., "Observations of the Pathologic Effects of Thiocyanate: An Experimental Study," American Heart Journal, vol. 21, No. 5, pp. 605-616 (1941).
Lipsky, A., et al., Managing toxicities of Bruton tyrosine kinase inhibitors, Hematology, American Society of Hematology Education Program, vol. 2020, No. 1, pp. 336-345 (2020).
Mahoney, M.G., et al., "Explanations for the clinical and microscopic localization of lesions in pemphigus foliaceus and vulgaris," Journal of Clinical Investigation, vol. 103, No. 4, pp. 461-468 (1999).
Maronpot, R.R., et al., "Hepatic Enzyme Induction: Histopathology," Toxicologic Pathology, vol. 38, pp. 776-795 (2010).
Martin, Y.C., et al., "Do structurally similar molecules have similar biological activity?," Journal of Medicinal Chemistry, vol. 45, No. 19, pp. 4350-4538 (2002).
Masters, S.L., et al., "Activation of the NLRP3 inflammasome by islet amyloid polypeptide provides a mechanism for enhanced IL-1Beta in type 2 diabetes," Nature Immunology, vol. 11, No. 10, pp. 897-904 (2010).
McKenzie, C.G., et al., "Cellular immune dysfunction in immune thrombocytopenia," British Journal of Haematology, vol. 163, pp. 10-23 (2013).
Metz, M., et al., "Fenebrutinib in H1 antihistamine-refractory chronic spontaneous urticaria: a randomized phase 2 trial," Nature Medicine, vol. 27, No. 11, pp. 1961-1969 (2021).
Michel, M., "Classification and therepeutic approaches in autoimmune hemolytic anemia: an update," Expert Review of Hematology, vol. 4, No. 6, pp. 607-618 (2011).
Michel, M., et al., "A randomized and double-blind controlled trial evaluating the safety and efficacy of rituximab for warm autoimmune hemolytic anemia in adults (the RAIHA study)," American Journal of Hematology, vol. 92, No. 1, pp. 23-27 (2017).
Mohamed, A.J., et al., Bruton's tyrosine kinase (Btk): function, regulation, and transformation with special emphasis on the PH domain, Immunology Review, vol. 228, pp. 58-73 (2009).
Montillo, M., et al., "Ibrutinib in previously treated chronic lymphocytic leukemia patients with autoimmune cytopenias in the RESONATE study," Blood Cancer Journal 7, No. e524 Letter to the Editor (2017).
Mosher, K.I., et al., "Go with your gut: microbiota meet microglia," Nature Neuroscience, vol. 18, pp. 930-931 (2015).
Murrell, D.F., et al., "Diagnosis and Management of Pemphigus: recommendations by an International Panel of Experts," Journal of American Academy of Dermatology (2018).
Nagasawa, H., et al., "Inhibitory effects of potassium thiocyanate on normal and neoplastic mammary development in female mice," European Journal of Cancer, vol. 16, No. 4, pp. 473-480 (1980).
Newman, K., et al., "Management of immune cytopenias in patients with systemic lupus erythematosus," Autoimmunity Reviews, vol. 12, No. 7, pp. 784-791 (2013).
Neys, S., et al., "Targeting Bruton's Tyrosine Kinase in Inflammatory and Autoimmune Pathologies," Frontiers in Cell & Developmental Biology, vol. 9, p. 668131 (2021).
Porro, A.M., et al., "Pemphigus vulgaris," Anais Brasileiros de Dermatologia, vol. 94, No. 3, pp. 264-278 (2019).
Press Release, "Sanofi to acquire Principia Biopharma," Aug. 17, 2020.
Rankin, A.L., et al., "Selective inhibition of BTK prevents murine lupus and antibody-mediated glomerulonephritis," Journal of Immunology, vol. 191, No. 9, pp. 4540-4550 (2012).
Rip, J., et al., "The role of Bruton's tyrosine kinase in immune cell signaling and systemic autoimmunity," Critical Reviews in Immunology, vol. 38, No. 1, pp. 17-62 (2018).
Rogers, K.A., et al., "Incidence and description of autoimmune cytopenias during treatment with ibrutinib for chronic lymphocytic leukemia," Leukemia, vol. 30, pp. 346-350 (2016).
Roumier, M., et al., "Characteristics and outcome of warm autoimmune hemolytic anemia in adults: New insights based on a single-center experience with 60 patients," American Journal of Hematology, vol. 89, No. 9, pp. E150-E155 (2014).
Saloojee, Y., et al., "Carboxyhaemoglobin and plasma thiocyanate: complementary indicators of smoking behaviour," Thorax, vol. 37, No. 7, pp. 521-525 (1982).
Schwab, I., et al., "Intravenous immunoglobulin therapy: how does IgG modulate the immune system?," Nature Reviews Immunology, vol. 13, pp. 176-189 (2013).
Serafimova, I.M., et al., "Reversible targeting of noncatalytic cysteines with chemically tuned electrophiles," Nature Chemical Biology, vol. 8, No. 5, pp. 471-476 (2012).
Shekunov, B Y et al., "Crystallization processes in pharmaceutical technology and drug delivery design", Journal of Crystal Growth, vol. 211, No. 104, Apr. 1, 2000, pp. 122-136.
Sideras, P., et al., "Molecular and cellular aspects of X-linked agammaglobulinemia," Advanced Immunology, vol. 59, pp. 135-223 (1995).
Storim, J., et al., "Dose-finding Phase 2 study to evaluate the efficacy and safety of the novel BTK inhibitor LOU064 in patients with CSU inadequately controlled by H1-antihistamines," Poster from 28th European Academy of Dermatology and Venereology Congress, Oct. 9-13, 2019 in Madrid, Spain.
Streicher, E., et al., "Distribution of thiocyanate between plasma and cerebrospinal fluid," American Journal of Physiology, vol. 206, No. 2, pp. 251-254 (1964).
Tan, S., et al., "Targeting the SYK-BTK axis for the treatment of immunological and hematological disorders: Recent progress and therapeutic perspectives," Pharmacological Therapy, vol. 138, No. 2, pp. 294-309 (2013).
Taylor, I., et al., "Comparison of longevity and common tumor profiles between Sprague-Dawley and Han Wistar rats," Journal of Toxicology & Pathology, vol. 33, pp. 189-196 (2020).
Unniappan, S., et al., "Leptin extends the anorectic effects of chronic PYY (3-36) administration in ad libitum-fed rats," American Journal of Physiology-Regulatory, Integrative and Comparitive Physiology, vol. 295, No. 1, pp. R51-R58 (2008).
Weber, A.N., "Targeting the NLRP3 Inflammasome via BTK," Frontiers in Cell and Developmental Biology, vol. 9, p. 630479 (2021).
Weber, A.N., et al., "Bruton's tyrosine kinase: an emerging key player in innate immunity," Frontiers in Immunology, vol. 8, pp. 1454 (2017).
Weber, K., "Differences in types and incidence of neoplasms in Wistar Han and Sprague-Dawley rats," Toxicology & Pathology, vol. 45, No. 1, pp. 64-75 (2017).

(56) References Cited

OTHER PUBLICATIONS

Wree, A., et al., "NLRP3 inflammasome activation results in hepatocyte pyroptosis, liver inflammation, and fibrosis in mice," Hepatology, vol. 59, No. 3, pp. 898-910 (2014).
Xu, D., et al., "RN486, a selective Bruton's tyrosine kinase inhibitor, abrogates immune hypersensitivity responses and arthritis in rodents," Journal of Pharmacology & Experimental Therapy, vol. 341, pp. 90-103 (2012).
Yamaguchi, T., "Mutagenicity of Isothiocyanates, Isocyanates and Thioureas on *Salmonella typhimurium*," Agricultural Biology & Chemistry, vol. 44, No. 12, pp. 3017-3018 (1980).
Zanella, A., et al., "Treatment of autoimmune hemolytic anemias," Haematologica, vol. 99, No. 10, pp. 1547-1554 (2014).
Zhang, D., et al., "Recent Advances in BTK Inhibitors for the Treatment of Inflammatory and Autoimmune Diseases," Molecules, vol. 26, No. 16, p. 4907 (2021).
Advani, R.H., et al., "Bruton tyrosine kinase inhibitor ibrutinib (PCI-32765) has significant activity in patients with relapsed/refractory B-cell malignancies," Journal of Clinical Oncology, vol. 31, No. 1, pp. 88-94 (2013).
American College of Rheumatology; ACR Covid-19 Vaccine Clinical Guidance Task Force, "Covid-19 vaccine clinical guidance summary for patients with rheumatic and musculoskeletal diseases," https://www.rheumatology.org/Portals/0/Files/COVID-19-Vaccine-Clinical-Guidance-Rheumatic-Diseases-Summary.pdf, cited May 10, 2021.
Anderson, R.C., et al., "Absorption and Toxicity of Sodium and Potassium Thiocyanates," Journal of American Pharmacists Association, vol. 29, No. 4, pp. 152-161 (1940).
Banerjee, K.K., et al., "Effect of thiocyanate ingestion through milk on thyroid hormone homeostasis in women," British Journal of Nutrition, vol. 78, No. 5, pp. 679-681 (1997).
Barcellini, W., et al., "Clinical heterogeneity and predictors of outcome in primary autoimmune hemolytic anemia: a GIMEMA study of 308 patients," Blood, vol. 124, No. 19, pp. 2930-2936 (2014).
Barker, M.H., "The Blood Cyanates in the Treatment of Hypertension," Journal of American Medical Association, vol. 106, No. 10, pp. 762-767 (1936).
Barker, M.H., et al., "Further Experiences with Thiocyanates," Journal of American Medical Association, vol. 117, No. 9, pp. 1591-1594 (1941).
Bartsch, R., et al., "Human relevance of follicular thyroid tumors in rodents caused by non-genotoxic substances," Regulatory Toxicology & Pharmacology, vol. 98, pp. 199-208 (2018).
Beissert, S., et al., "A comparison of oral methylprednisolone plus azathioprine or mycophenolate mofetil for the treatment of pemphigus," Archives of Dermatology, vol. 142, No. 11, pp. 1447-1454 (2006).
Bhandari, R.K., et al., "Cyanide toxicokinetics: the behavior of cyanide, thiocyanate and 2-amino-2-thiazoline-4-carboxylic acid in multiple animal models," Journal of Analytical Toxicology, vol. 38, No. 4, pp. 218-225 (2014).
Bizikova, P., et al., "Cloning and establishment of canine desmocollin-1 as a major autoantigen in canine pemphisgus foliaceus," Veterinary Immunology & Immunopathology, vol. 149, pp. 197-207 (2012).
Bizikova, P., et al., "Serum autoantibody profiles of IgA, IgE and IgM in canine pemphigus foliaceus," Veterinary Dermatology, vol. 25, pp. 471-475 (2014).
Bolon, B., et al., "STP Position Paper: Recommended Practices for Sampling and Processing the Nervous System (Brain, Spinal Cord, Nerve, and Eye) during Nonclinical General Toxicity Studies," Toxicologic Pathology, vol. 41, pp. 1028-1048 (2013).
Borthakur, G., et al., "Immune anaemias in patients with chronic lymphocytic leukaemia treated with fludarabine, cyclophosphamide and rituximab—incidence and predictors," British Journal of Haematology, vol. 136, No. 6, pp. 800-805 (2007).
Boulos, B.M., et al., "Placental transfer of antipyrine and thiocyanate and their use in determining maternal and fetal body fluids in a maintained pregnancy," Archives Internacionales de Pharmacodynamie et de Therapie, vol. 201, No. 1, pp. 42-51 (1973).
Bradshaw, J.M., et al., "Prolonged and tunable residence time using reversible covalent kinase inhibitors," Nature Chemical Biology, vol. 11, No. 7, pp. 525-531 (2015).
Brodsky, R.A., "Warm Autoimmune Hemolytic Anemia," New England Journal of Medicine, vol. 381, No. 7, pp. 647-654 (2019).
Brown, J.R., et al., "Phase I study of single-agent CC-292, a highly selective Bruton's tyrosine kinase inhibitor, in relapsed/refractory chronic lymphocytic leukemia," Haematologica, vol. 101, p. e295 (2016).
Burger, J.A., "Bruton Tyrosine Kinase Inhibitors: Present and Future," Cancer Journal, vol. 25, No. 6, pp. 386-393 (2019).
Burger, J.A., et al., "Randomized Trial of Ibrutinib Versus Ibrutinib Plus Rituximab (Ib+R) in Patients with Chronic Lymphocytic Leukemia (CLL)," Blood, vol. 130, p. 427 (2017).
Bussel, J.B., et al., "Eltrombopag for the treatment of chronic idiopathic thrombocytopeniarpura," New England Journal of Medicine, vol. 357, pp. 2237-2247 (2007).
Butt, M.T., et al., "Nervous System: Astrocytosis," In Toxicologic Pathology Nonclinical Safety Assessment, Sahota, P.S., Popp, J.A., Hardisty, J.F., and Gopinath, C. (eds), vol. 20, pp. 901-903 (2013).
Byrd, J.C., et al., "Acalabrutinib (ACP-196) in relapsed chronic lymphocytic leukemia," New England Journal of Medicine, vol. 374, No. 4, pp. 323-332 (2016).
Carnero-Contentti, E., et al., "Bruton's tyrosine kinase inhibitors: a promising emerging treatment option for multiple sclerosis," Expert Opinion on Emerging Drugs, vol. 25, No. 4, pp. 377-381 (2020).
Chandler, J.D., et al., "Biochemical Mechanisms and Therapeutic Potential of the Pseudohalide Thiocyanate in Human Health," Free Radical Research, vol. 49, No. 6, pp. 695-710 (2015).
Chang, B.Y., et al., "The Bruton tyrosine kinase inhibitor PCI-32765 ameliorites autoimmune arthritis by inhibition of multiple effector cells," Arthritis Research & Therapy, vol. 13, No. 4, p. R115 (2011).
Chaplin, H., Jr., "Clinical usefulness of specific antiglobulin reagents in autoimmune hemolytic anemias," Hematology Program, vol. 8, pp. 25-49 (1973).
Chaudhri, O.B., et al., "Can Gut Hormones Control Appetite and Prevent Obesity?," Diabetes Care, vol. 31, pp. S284-S289 (2008).
Chen, J.F., et al., "The clinical significance of circulating B cells and secreting anti-glycoprotein IIb/IIIa antibody and platelet glycoprotein IIb/IIIa in patients with primary immune thrombocytopenia," Hematology, vol. 15, pp. 283-290 (2013).
Code of Federal Regulations, Title 21, Chapter II, Part 1308, Schedules of Controlled Substances, Mar. 12, 2021.
Crowther, M., et al., "Evidence-based focused review of the treatment of idiopathic warm immune hemolytic anemia in adults," Blood, vol. 118, No. 15, pp. 4036-4040 (2011).
DeSilva, A., et al., "Gut Hormones and Appetite Control: A Focus on PYY and GLP-1 as Therapeutic Targets in Obesity," Gut Liver, vol. 6, No. 1, pp. 10-20 (2012).
Dierickx, D., et al., "Rituximab in autoimmune haemolytic anaemia and immune thrombocytopeniarpura: a Belgian retrospective multicentric study," Journal of Internal Medicine, vol. 266, No. 5, pp. 484-491 (2009).
DiPaolo, J.A., et al., "Specific Btk inhibition suppresses B cell- and myeloid cell-mediated arthritis," Nature Chemical Biology, vol. 7, pp. 41-50 (2011).
Dispenza, M.C., et al., "Bruton's tyrosine kinase inhibition effectively protects against human IgE-mediated anaphylaxis," Journal of Clinical Investigation, vol. 130, No. 9, pp. 4759-4770 (2020).
Eaton, W.W., et al., "Epidemiology of autoimmune diseases in Denmark," Journal of Autoimmunity, vol. 29, No. 1, pp. 1-9 (2007).
Elizondo-Vega, R., et al., "The role of tanycytes in hypothalamic glucosensing," Journal of Cellular and Molecular Medicine, vol. 19, pp. 1471-1482 (2015).
Fayyaz, A., et al., "Haematological manifestations of lupus," Lupus Science & Medicine, vol. 2, No. 1, p. e000078 (2015).
Futatani, T., et al., "Bruton's tyrosine kinase is present in normal platelets and its absence identifies patients with X-inked agammaglobulinaemia and carrier females," British Journal of Haematology, vol. 114, No. 1, pp. 141-149 (2001).

(56) References Cited

OTHER PUBLICATIONS

Gao, Y., et al., "Hormones and diet, but not body weight, control hypothalamic microglial activity," Glia, vol. 62, pp. 17-25 (2014).
Garvin, C.F., "The Fatal Toxic Manifestations of the Thiocyanates," Journal of American Medical Association, vol. 112, No. 12, pp. 1125-1127 (1939).
Ghoroi, C., et al., "Multi-faceted characterization of pharmaceutical powders to discern the influence of surface modification", Powder Technology, vol. 236, May 22, 2012, pp. 63-74.
Goodman, T., et al., "Hypothalamic tanycytes—masters and servants of metabolic, neuroendocrine, and neurogenic functions," Frontiers in Neuroscience, vol. 9, p. 387 (2015).
Gordon, R., et al., "Inflammasome inhibition prevents alpha-synuclein pathology and dopaminergic neurodegeneration in mice," Science Translational Medicine, vol. 10, No. 465, p. eaah4066 (2018).
GRAS notification for sodium thiocyanate for use in the lactoperoxidase system, https://www.fda.gov/files/food/published/GRAS-Notice-GRN-753.pdf.
Gregoriou, S., et al., "Management of pemphigus vulgaris: challenges and solutions," Clinical, Cosmetic & Investigational Dermatology, vol. 8, pp. 521-527 (2015).
Heneka, M.T., et al., "NLRP3 is activated in Alzheimer's disease and contributes to pathology in APP/PS1 mice," Nature, vol. 492, No. 7434, pp. 674-678 (2013).
Hertl, M., et al., "Pemphigus. S2 Guideline for diagnosis and treatment—guided by the European Dermatology Forum (EDF) in cooperation with the European Academy of Dermatology and Venereology (EADV)," Journal of the European Academy of Dermatology and Venereology, vol. 29, No. 3, pp. 405-414 (2015).
Hill, Q.A., et al., "The diagnosis and management of primary autoimmune haemolytic anaemia," British Journal of Haematology, vol. 176, No. 3, pp. 395-411 (2017).
Hodgson, K., et al., "Autoimmune cytopenia in chronic lymphocytic leukemia: diagnosis and treatment," British Journal of Haematology, vol. 154, No. 1, pp. 14-22 (2011).
Structure-Based Search Results (May 10, 2011, 10:20 AM), SciFinder.
Structure-Based Search Results (May 10, 2011, 10:46 AM), SciFinder.
Structure-Based Search Results (May 9, 2011, 8:13 PM), SciFinder.
Structure-Based Search Results (May 9, 2011, 8:23 PM), SciFinder.
Structure-Based Search Results (May 9, 2011, 8:33 PM), SciFinder.
Structure-Based Search Results (May 9, 2011, 9:06 PM), SciFinder.
Kamisawa, T., et al., "IgG4-related disease", The Lancet, vol. 385, No. 9976, pp. 1460-1471 (2015).
Van Beek, N et al., "Therapy of pemphigus", Hautarzt, Springer Verlag, Berlin, DE, vol. 70, No. 4, pp. 243-253 (Mar. 18, 2019).
Vayne, C., et al., "Pathophysiology and Diagnostic of Drug-Induced Immune Thrombocytopenia," Journal of Clinical Medicine, vol. 9, No. 7, p. 2212 (2020).
Verhe, R., et al., "Preparation of 2,2-Dialkylcyclopropanes Geminally Substituted with Electron-Withdrawing Groups," Synthesis, vol. 7, pp. 530-532 (1978).
Verhe, R., et al., "Synthesis of 1,1-Bis(Hydroxymethyl) Cyclopropanes," Organic Preparations and Procedures International, vol. 13, No. 1, pp. 13-18 (1981).
Verhe, R., et al., "Thermal Lactonization of Brominated Alkylidenemalonates: Synthesis of 2-Buten-4-Olides," Bulletin des Societes Chimiques Belges, vol. 87, No. 3, pp. 215-222 (1978).
Vo, N., et al., "Transformations of Resin-Bound Pyridinium Ylides: I. A Stereoselective Synthesis of 2,2,3—Trisubstituted Cyclopropanecarboxylates," Tetrahedron Letters, vol. 38, No. 46, pp. 7951-7954 (1997).
Von Hundelshausen, P., et al., "Vaccine-Induced Immune Thrombotic Thrombodytopenia (VITT): Targeting Pathomechanisms with Bruton Tyrosine Kinase Inhibitors", Thrombosis and Haemostasis, vol. 121, No. 11, pp. 1395-1399 (2021).
Wang, G., et al., "Substituted 4-amino-1H-pyrazolo[3,4-d]pyrimidines as multi-targeted inhibitors of insulin-like growth factor-I receptor (IGFIR) and members of ErbB-family receptor kinases," Bioorganic Medicinal and Chemistry Letters, vol. 20, pp. 6067-6071 (2010).
Wang, K., et al., "Cyanoacetamide Multicomponent Reaction (I): Parallel Synthesis of Cyanoacetamides," Journal of Combinatorial Chemistry, vol. 11, pp. 920-927 (2009).
WebMD. 10 Ways to Prevent Psoriasis Flare-Ups. Web: (2016).
WebMD. Multiple Sclerosis (MS)-Prevention. Web: <http://www.webmd.com/multiple-sclerosis/tc/multiple-sclerosis-ms-prevention> (2015).
Wells, G., et al., "Structural Studies on Bioactive Compounds. 32.1 Oxidation of Tyrphostin Protein Tyrosine Kinase Inhibitors with Hypervalent Iodine Reagents," Journal of Medicinal Chemistry, vol. 43. pp. 1550-1562 (2000).
WhatisDryEye.com. Dry Eye vs. Conjunctivitis Web: (2016).
Wilding, I., et al., "Targeting of Drugs and Vaccines to the Gut," Pharmacology and Therapeutics, vol. 62, pp. 97-124 (1994).
Wissner, A., et al., "Synthesis and Structure-Activity Relationships of 6,7-Disubstituted 4-Anilinoquinoline-3-carbonitriles. The Design of an Orally Active, IrreversibleInhibitor of the Tyrosine Kinase Activity of the Epidermal Growth Factor Receptor (EGFR) and the Human Epidermal Growth Factor Receptor-2 (HER-2)," Journal of Medicinal Chemistry, vol. 46, pp. 49-63 (2003).
Zhang, F., et al., "Organic base catalyzed carbonyl allylation of methyl trifluoropyruvate with activated alkenes," Tetrahedron Letters, vol. 65, pp. 83-86 (2009).
Zimmerman, H., et al., "The Diverted Di-π-Methane Rearrangement; Mechanistic and Exploratory Organic Photochemistry," Organic Letters, vol. 4, No. 7, pp. 1155-1158 (2002).
U.S. Appl. No. 63/176,543, filed Apr. 19, 2021, Christopher W. Smith.
"Solubility, Polymorphism, Crystallinity, and Crystal Habit of Acetaminophen and Ibuprofen by Initial Solvent Screening," PharmaTech.com, vol. 30, No. 10, pp. 1-3 (2006).
"Supplement Article", The Authors, British Journal of Haematology, vol. 185, suppl. 1, pp. 3-202 (2019).
2012 ICD-9-CM Diagnosis Code 372.30: Conjunctivitis, unspecified, retrieved Aug. 4, 2016 (1 page).
Abdulahad, W., et al., "Immune regulation and B-cell depletion therapy in patients with primary Sjogren's syndrome," J Autoimmun, 39(1): 103-111 (2012).
Abstract for Nepl Yuev, V., "Nitration and nitrosation of 1, 1,3,3-tetraacyl-1-propenes" Ukrainskii Khimicheskii Zhurnal (Russian Edition), 49(2):192-194 (1 page) (1983).
Abstract for Nepl Yuev, V., "Studies of triacylmethanes VII. 1,1,3,3-Tetraacyl-3-arylazo-1-propenes," Zhurnal Organicheskoi Khimii, 15(3): 563-566 (1 page) (1979).
American Cancer Society. Can Non-Hodgkin's Lymphoma Be Prevented? Web: (2016).
Ansel, H., et al., "Pharmaceutical Dosage Forms and Drug Delivery Systems," Seventh Edition, Lippincott Williams & Wilkins, A Wolters Kluwer Company, Chapters 1-8, pp. 1-243 (1999).
Armesto, D., et al., "Efficient photochemical synthesis of 2-vinylcyclopropanecarbaldehydes, precursors of cyclopropane components present in pyrethroids, by using the oxa-di-TT-methane rearrangement," Tetrahedron, 66: 8690-8697 (2010).
Arnold, L., et al., "Pyrrolo[2,3-d]pyrimidines Containing an Extended 5-Substituent as Potent and Selective Inhibitors of lck I," Bioorg. Med. Chem. Lett., 10:2167-2170 (2000).
Arora, A., et al., "Role of Tyrosine Kinase Inhibitors in Cancer Therapy," J Pharmacol. Exp. Ther., 315(3):971-979 (2005).
Basheer, A., et al., "Enols of Substituted Cyanomalonamides," J Org. Chem. 72:5297-5312 (2007).
Bastin, R., et al., "Salt Selection and Optimisation Procedures for Pharmaceutical New Chemical Entities," Org. Process Res. Dev, 4:427-435 (2000).
Berge, S., et al., "Pharmaceutical Salts," J Pharm. Sci., 66:1-19 (1977).
Bernhart, C., et al., "Synthesis and Antiarrhythmic activity of New [(Dialkylamino)alkyl]pyridylacetamides," J Med Chem., 26:451-455 (1983).

(56) References Cited

OTHER PUBLICATIONS

Bradshaw, J., et al., "Prolonged and tunable residence time using reversible covalent kinase inhibitors," Nat Chem. Biol., 11:525-531 (with online methods) (2015).
Burchat, A., et al., "Pyrrolo[2,3-d]pyrimidines Containing an Extended 5-Substituent as Potent and Selective Inhibitors of lck II," Bioorg. Med. Chem. Lett, 10:2171-2174 (2000).
Burini, E., et al., "Efficient Synthesis of 4-Cyano 2,3-Dihydrooxazoles by Direct Amination of 2-Alkylidene 3-Oxo Nitriles," Synlett, 17: 2673-2675 (2005).
Caira, M., et al., "Crystalline Polymorphism of Organic Compounds," Topics in Current Chemistry, vol. 198, pp. 163-208 (1998).
Calderwood, D., et al., "Pyrrolo[2,3-d]pyrimidines Containing Diverse N-7 Substituents as Potent Inhibitors of Lck," Bioorg. Med. Chem. Lett., 12:1683-1686 (2002).
Carruthers, M., et al., "Development of an IgG4-RD Responder Index," International Journal of Rheumatology, vol. 2012, pp. 1-8 (2012).
CAS RN 26272-41-3, STN entered Nov. 16, 1984 (1 page).
Certified English Translation of CN 105753863 A published in Chinese on Jul. 13, 2016 (57 pages).
Chinese Pharmacopoeia Commission, "The Third Supplement of the Pharmacopoeia of People's Republic of China (Edition 2010)," Beijing: China Medical Science Press, p. 213 (Nov. 30, 2014).
ClinicalTrial.gov ID No. NCT02704429, "A Study of PRN1008 in Adult Patients With Pemphigus Vulgaris", last update posted Feb. 13, 2023 (49 pages).
ClinicalTrial.gov ID No. NCT03395210, "A Study of Rilzabrutinib in Adult Patients With Immune Thrombocytopenia (ITP)", last update posted Jul. 28, 2023 (18 pages).
ClinicalTrial.gov ID No. NCT03762265, "A Study of PRN1008 in Patients With Pemphigus", last update posted Aug. 2, 2023 (104 pages).
ClinicalTrial.gov ID No. NCT04520451, "Open Label Two-Arm Study to Evaluate Rilzabrutinib in IgG4-Related Disease Patients", last update posted Sep. 7, 2023 (20 pages).
ClinicalTrial.gov ID No. NCT04562766, "Study to Evaluate Rilzabrutinib in Adults and Adolescents With Persistent or Chronic Immune Thrombocytopenia (ITP) (LUNA 3)", last update posted Aug. 21, 2023 (24 pages).
ClinicalTrial.gov ID No. NCT04748926, "Food Effect and Relative Bioavailability Study of Rilzabrutinib in HealthyParticipants", last update posted Apr. 25, 2022 (20 pages).
ClinicalTrial.gov ID No. NCT05002777, "Efficacy, Safety and Pharmacokinetics of Rilzabrutinib in Patients With Warm Autoimmune Hemolytic Anemia (wAIHA)", last update posted Jul. 27, 2023 (20 pages).
ClinicalTrial.gov ID No. NCT05018806, "Proof of Concept Study of Rilzabrutinib in Adult Patients With Moderate-to-severe Atopic Dermatitis", last update posted Jul. 6, 2023 (23 pages).
ClinicalTrial.gov ID No. NCT05104892, "Proof of Concept Study of Rilzabrutinib in Adult Participants With Moderate-to-severe Asthma", last update posted Aug. 21, 2023 (25 pages).
ClinicalTrial.gov ID No. NCT05107115, "Rilzabrutinib for the Treatment of Chronic Spontaneous Urticaria in Patients Who Remain Symptomatic Despite the Use of H1 Antihistamine (RILECSU)", last update posted Aug. 24, 2023 (22 pages).
Cohen, M., et al., "Structural Bioinformatics-Based Design of Selective, Irreversible Kinase Inhibitors," Science, 308:1318-1321 (2005).
Cui, C., et al., "Factors Contributing to Drug Release From Enteric-Coated Omeprazole Capsules: An In Vitro and In Vivo Pharmacokinetic Study and IVIVC Evaluation in Beagle Dogs," Nanotechnology and Microtechnology in Drug Delivery Systems, vol. Jan.-Mar. 2020, pp. 1-13 (Jan. 7, 2020).
Database Biosis [Online], Biosciences Information Service, Kuter, D., et al., "Cognitive Impairment Among Patients with Chronic Immune Thromocytopenia," Blood, vol. 140, suppl. 1, pp. 8422-8424 (2022).

Database Biosis [Online], Biosciences Information Service, Langrish, C., et al., "PRN1008, a Reversible Covalent BTK Inhibitor in Cinical Development for Immune Thrombocytopenia Purpura," Blood, vol. 130, suppl. 1, p. 1052 (2017).
Database Embase [Online], Elsevier Science Publishers, Kuter, D., "Oral Rilzabrutinib, a Bruton Tyrosine Kinase Inhibitor, Showed Clinically Active and Durable Platelet Responses and Was Well-Tolerated in Patients with Heavily Pretreated Immune Thrombocytopenia," Blood, vol. 136, suppl. 1, pp. 20201205-20201208 (2020).
Database Embase [Online], Elsevier Science Publishers, Kuter, D., "Updated main study period and long-term extension (LTE) results with oral Bruton tyrosine kinase inhibitor rilzabrutinib in immune thrombocytopenia (ITP)," Research and Practice in Thrombosis and Haemostasis, vol. 6, suppl. 1 (2022).
Deng, Y., et al., "Reversible phospho-Smad3 signalling between tumour suppression and fibrocarcinogenesis in chronic hepatitis B infection," Clin. Exp. Immunol., 176:102-111 (2013).
Dias, A., et al., "Ibrutinib: A New Frontier in the Treatment of Chronic Lymphocytic Leukemia by Bruton's Tyrosine Kinase Inhibition," Cardiovasc Hematol Agents Med Chem, 11 (4):265-271 (2013).
Dick, et al., "Pemphigus: A treatment update," Autoimmunity 2009, vol. 39, No. 7, pp. 591-599 (Jul. 7, 2009).
Donald, A., et al., "Rapid Evolution of 6-Phenylpurine Inhibitors of Protein Kinase B through Structure-Based Design," J Med. Chem., 50:2289-2292 (2007).
Elinson, M., et al., "Electrochemical transformation of cyanoacetic ester and alkylidenecyanoacetic esters into 3-substituted 1,2-dicyanocyclopropane-1,2-dicarboxylates," Russian Chemical Bulletin, 47(6):1133-1136 (1998).
Elliott, M., et al., "Insecticidal activity of the Pyrethrins and Related Compounds x.• 5-Benzyl-3-furylmethyl 2,2-dimethylcyclopropanecarboxylates with ethylenic substituents at position 3 on the cyclopropane ring," Pestic. Sci., 7:499-502 (1976).
Elliott, M., et al., "The Pyrethrins and Related Compounds. Part XVIII. Insecticidal 2,2-Dimethylcyclopropanecarboxylates with New Unsaturated 3-Substituents," Journal of the Chemical Society, Perkin Transactions 1: Organic and Bio-Organic Chemistry, vol. 21, 2470-2474 (1972-1999) (1974).
English Language Abstract for JP 42008308 B4, published Apr. 8, 1967, by Yoshitomi Pharmaceutical Industries, Ltd. (1 page).
English Translation of Office Action issued Apr. 12, 2013, in Chinese Application No. 201080061570.1.
EU Clinical Trials Register, ACT17125, Spain, first entered into EudraCT Dec. 20, 2022 (5 pages).
EU Clinical Trials Register, ACT17207, Germany, first entered into EudraCT Aug. 6, 2021 (5 pages).
EU Clinical Trials Register, ACT17208, Spain, first entered into EudraCT Aug. 5, 2021 (7 pages).
EU Clinical Trials Register, ACT17209, Spain, first entered into EudraCT Jun. 23, 2021 (6 pages).
EU Clinical Trials Register, DFI17124, Czech, first entered into EudraCT Dec. 12, 2017 (8 pages).
EU Clinical Trials Register, DRI17224, Spain, first entered into EudraCT Jul. 15, 2021 (6 pages).
EU Clinical Trials Register, EFC17092, Summary Results, Jul. 29, 2022 (9 pages).
EU Clinical Trials Register, EFC17093, Germany, first entered into EudraCT Oct. 1, 2020 (6 pages).
EU Clinical Trials Register, PRN1008-012, France, first entered into EudraCT Oct. 22, 2018 (6 pages).
Evans, E., et al., "Inhibition of Btk with CC-292 Provides Early Pharmacodynamic Assessment of Activity in Mice and Humans," J. Pharm. Exp. Ther., 346(2):219-28 (2013).
Fioravanti, S., et al., "Parallel Solution-Phase Synthesis of Acrylonitrile Scaffolds Carrying L-a- Amino Acidic or D-Glycosyl Residues," J Comb. Chem., 8: 808-811 (2006).
Ghoreschi, K., et al., "Janus kinases in immune cell signaling," Immunol Rev., 228:273-287 (2009).

(56) References Cited

OTHER PUBLICATIONS

Goldmann, L., et al., "Oral Bruton tyrosine kinase inhibitors block activation of the platelet Fc receptor CD32a (FcgRIIA): a new option in HIT?," Blood Advances, vol. 3, No. 23, pp. 4021-4033 (2020).
Grando, S. "Pemphigus autoimmunity: Hypotheses and realities," Autoimmunity, 45(1):7-35 (2012).
Gyoung, Y., et al., "Regiospecific synthesis of 2-allylated-5-substituted tetrazoles via palladium-catalyzed reaction of nitriles, trimethylsilyl azide, and allyl acetates," Tetrahedron Lett., 41 (21): 4193-4196 (2000).
Hackam, D., et al., "Translation of Research Evidence from Animals to Humans," JAMA, 296(14):1731-1732 (2006).
Hantschel, O., et al., "The Btk tyrosine kinase is a major target of the Bcr-Abl inhibitor dasatinib." PNAS, 104(33):13283-13288 (2007).
Hu, C., "Production and Application of a Pharmaceutical Excipient—Thin Film Coating," Beijing: China Medical Science Press, p. 14 (May 31, 2014).
Hu, R., "Industrial Pharmaceutics," Beijing: China Press of Traditional Chinese Medicine, pp. 237-239 (Jul. 31, 2010).
International Preliminary Report on Patentability for International Application No. PCT/US2010/056890, mailed May 22, 2012, by P. Becamel (10 pages).
International Preliminary Report on Patentability for International Application No. PCT/US2021/012211, mailed on Jul. 21, 2022, by X. Wang (11 pages).
International Preliminary Report on Patentability for International Application No. PCT/US2021/014371, mailed Aug. 4, 2022, by S. Baharlou (7 pages).
International Preliminary Report on Patentability for International Application No. PCT/US2022/024806, mailed Oct. 26, 2023, by X. Tang (8 pages).
International Search Report and Written Opinion for International Application No. PCT/US2010/056890, mailed Jul. 28, 2011, by S. Lee (16 pages).
International Search Report and Written Opinion for International Application No. PCT/US2012/038092, mailed Jul. 5, 2012, by A. Schmid (8 pages).
International Search Report and Written Opinion for International Application No. PCT/US2012/038120, mailed Aug. 20, 2012, by I. Helps (10 pages).
International Search Report and Written Opinion for International Application No. PCT/US2012/038135, mailed Jul. 25, 2012, by I. Helps (9 pages).
International Search Report and Written Opinion for International Application No. PCT/US2012/038163, mailed Jul. 9, 2012, by A. Schmid (8 pages).
International Search Report and Written Opinion for International Application No. PCT/US2012/038214, mailed Feb. 1, 2013, by Y. Kim (12 pages).
International Search Report and Written Opinion for International Application No. PCT/US2013/045266, mailed Sep. 3, 2013, by W. Hoepfner (11 pages).
International Search Report and Written Opinion for International Application No. PCT/US2013/047958, mailed Oct. 1, 2013, by S. Gomez Gallardo (14 pages).
International Search Report and Written Opinion for International Application No. PCT/US2013/053042, mailed Nov. 18, 2013, by M. Kollmannsberger (12 pages).
International Search Report and Written Opinion for International Application No. PCT/US2013/058614, mailed Nov. 5, 2013, by C. Ladenburger (11 pages).
International Search Report and Written Opinion for International Application No. PCT/US2015/000303, mailed Mar. 21, 2016, by J. Konter (12 pages).
International Search Report and Written Opinion for International Application No. PCT/US2015/000515, mailed Apr. 18, 2016, by M. Kollmannsberger (11 pages).
International Search Report and Written Opinion for International Application No. PCT/US2015/016963, mailed Apr. 22, 2015, by T. Albayrak (10 pages).
International Search Report and Written Opinion for International Application No. PCT/US2015/066868, mailed Mar. 9, 2016, by S. Allnutt (13 pages).
International Search Report and Written Opinion for International Application No. PCT/US2016/035588, mailed Aug. 16, 2016, by W. Hoepfner (10 pages).
International Search Report and Written Opinion for International Application No. PCT/US2016/039070, mailed Oct. 6, 2016, by R. Saez Diaz (18 pages).
International Search Report and Written Opinion for International Application No. PCT/US2017/040075, mailed Oct. 2, 2017, by M. Ceyte (9 pages).
International Search Report and Written Opinion for International Application No. PCT/US2020/054809 mailed Jan. 25, 2021, by S. Collins (12 pages).
International Search Report and Written Opinion for International Application No. PCT/US2020/065689, mailed on Apr. 29, 2021, by J. Guspanova (17 pages).
International Search Report and Written Opinion for International Application No. PCT/US2021/012211 mailed on Apr. 9, 2021, by B. Megido (13 pages).
International Search Report and Written Opinion for International Application No. PCT/US2021/014371, mailed Mar. 22, 2021, by S. Bissmire (14 pages).
International Search Report and Written Opinion for International Application No. PCT/US2022/024806, mailed Jul. 21, 2022, by M. Rodriguez-Palmero (12 pages).
International Search Report and Written Opinion for International Application No. PCT/US2023/078211 dated Feb. 12, 2024, by N. Hick (13 pages).
International Search Report and Written Opinion for International Application No. PCT/US2023/083090, mailed on Apr. 30, 2024, by I. Estanol (12 pages).
Izumi, K. et al., "Current Clinical Trials in Pemphigus and Pemphigoid", Frontiers in Immunology, vol. 10, p. 978 (May 3, 2019).
Jenner, G., "Steric effects in high pressure Knoevenagel reactions," Tetrahedron Lett., 42(2): 243-245 (2001).
Liu, J., et al., "Emerging small-molecule inhibitors of the Bruton's tyrosine kinase (BTK): Current development", European Journal of Medicinal Chemistry, vol. 217, Mar. 12, 2021, p. 113329.
Johnson, M., et al., "Coding for Dry Eye," Optometric Management, Issue: Mar. 2004 (1 page).
Jordan, V., "Tamoxifen: A Most Unlikely Pioneering Medicine," Nat Rev. Drug Discov., 2:205-213 (2003).
Kamaly, N., et al., "Degradable Controlled-Release Polymers and Polymeric Nanparticles: Mechanisms of Controlling Drug Release," Chemical Reviews, vol. 116, pp. 2602-2663 (Feb. 8, 2016).
Kamath, S., et al., "Receptor-Guided Alignment-Based Comparative 3D-QSAR Studies of Benzylidene Malonitrile Tyrphostins as EGFR and HER-2 Kinase Inhibitors," J Med. Chem., 46:4657-4668 (2003).
Kamijo, S., et al., "Tetrazole synthesis via the palladium-catalyzed three component coupling reaction," Molecular Diversity, 6: 181-192 (2003).
Kanwar, A., et al., "Rituximab in Pemphigus," Indian J Dermatol. Venereal. Leprol. [serial online], 78:671-676 (2012).
Khosroshani, A., et al., "Rituximab for the treatment of IgG4-Related Disease," Medicine, vol. 91, pp. 57-66 (2012).
Knight, Z., et al., "A membrane capture assay for lipid kinase activity," Nat Protoc., 2(10):2459-2466 (2017).
Kojima, S., et al. "Stereoselective synthesis of activated cyclopropanes with an a-pyridinium acetamide bearing an 8-phenylmenthyl group as the chiral auxiliary," Tetrahedron Lett., 45(18): 3565-3568 (2004).
Komura, K., et al., "Layered silicate PLS-1: A new solid base catalyst for C-C bond forming reactions," Cata! Commun., 8(4): 644-648 (2007).
Kotz, A., et al., "The Action of Chloroform on Methylene and Metheny! Groups," Journal fuer Praktische Chemie (Leipzig), Abstract, 74: 425-48 (1907).

(56) References Cited

OTHER PUBLICATIONS

Kuter, D., et al., "LUNA3 Phase III Multicenter, Double-Blind, Randomized, Placebo-Controlled Trial of the Oral BTK Inhibitor Rilzabrutinib in Adults and Adolescents with Persistent or Chronic Immune Thrombocytopenia," Blood, vol. 138, supplement 1, p. 1010 (2021).
Kuter, D., et al., "Phase I/II, open-label, adaptive study of oral tyrosine inhibitor patients with relapsed/refractory primary or secondary immune thrombodytopenia," Blood, vol. 134 (Suppl 1), p. 87 (2019).
Kuter, D., et al., "Rilzabrutinib versus placebo in adults and adolescents with persistent or chronic immune thrombocytopenia: LUNA3 phase III study," Therapeutic Advances in Hematology, vol. 14, pp. 1-14 (2023).
Langrish, C., et al., "PRN1008, a Reversible Covalent BTK Inhibitor in Clinical Development for Immune Thrombocytopenia Purpura," Blood, vol. 130, suppl. 1, No. 1052 (2017).
Leopold, C., "A Practical Approach in the Design of Colon-specific Drug Delivery System," Wiley-VCH; Drug Targeting Organ-Specific Strategies, Chapter 6, pp. 157-170 (2001).
Zhensu, L., Medicinal Chemistry, Chemical Industry Press, China, Mar. 3, 1981, pp. 435-436.
Liang, C., et al., "The development of Bruton's tyrosine kinase (BTK) inhibitors from 2012 to 2017: A mini-review," European Journal of Medicinal Chemistry, vol. 151, pp. 315-326 (2018).
Lou, Y., et al., "Bruton's Tyrosine Kinase Inhibitors: Approaches to Potent and Selective Inhibition, Preclinical and Clinical Evaluation for Inflammatory Diseases and B Cell Malignancies," J Med. Chem., 55(10): 4539-4550 (2012).
Maas, S., et al., "Conjugate Addition of Dialkylaluminum Chlorides to Alkylidenemalonic Acid Derivatives," Synthesis, vol. 10, pp. 1792-1798 (1999).
Mahajan, V., et al., "IgG4-Related Disease," Annual Review of Pathology: Mechanisms of Disease, vol. 9, pp. 315-347 (2014).
Maurya, R., et al., "Catalyst-free stereoselective cyclopropanation of electron deficient alkenes with ethyl diazoacetate," RSC Advances, vol. 3, pp. 15600-15603 (2013).
MedicineNet.com. Definition of Cancer. Web: (2004).
MedlinePlus. Autoimmune Diseases, Web: (2014).
Meydan, N., et al., "Inhibition of acute lymphoblastic leukaemia by a Jak-2 inhibitor," Nature, vol. 379, pp. 645-648 (1996).
Miller, R., "Electrophilic Fragment-Based Design of Reversible Covalent Kinase Inhibitors," Journal of the American Chemical Society, vol. 135, No. 14, pp. 5298-5301 (2013).
Murrell, D., et al., "A Pilot Study of the Efficacy of a Bruton's Tyrosine Kinase Inhibitor in the Treatment of Dogs with Pemphigus Foliaceus", Australasian Journal of Dermatology, vol. 58, No. S1, p. 73 (Jan. 1, 2017).
Nakamura, M. et al., "Diquafosol Ophthalmic Solution for Dry Eye Treatment," Advances in Therapy, vol. 29, No. 7, pp. 579-589 (2012).
Outerbridge, C., et al., "A new treatment for autoimmune blistering diseases—the efficacy of the Bruton's tyrosine kinase inhibitor PRN473 in canine pemphigus foliaceus," Journal of American Academy of Dermatology, No. 3530, p. AB141 (2016).
Pan, Z. et al., "Discovery of Selective Irreversible Inhibitors for Bruton's Tyrosine Kinase," ChemMedChem, vol. 2, pp. 58-61 (2007).
Patani, G., et al., "Bioisosterism: A Rational Approach in Drug Design," Chemical Reviews, vol. 96, pp. 3147-3176 (1996).

Peng, T., et al., "Data on the drug release profiles and powder characteristics of the ethyl cellulose based microparticles prepared by the ultra-fine particle processing system," Data in Brief, vol. 29, pp. 105629, pp. 1-6 (Feb. 8, 2020).
Pennington, L., et al., "The Necessary Nitrogen Atom: A Versatile High-Impact Design Element for Multiparameter Optimization," Journal of Medicinal Chemistry, vol. 60, No. 9, pp. 3552-3579 (2017).
Porter, D., et al., "The discovery of potent, orally bioavailable pyrimidine-5-carbonitrile-6-alkyl CXCR2 receptor antagonists," Bioorganic and Medicinal Chemistry Letters, vol. 24, pp. 3285-3290 (2014).
Principia Biopharma: "A Study of PRN1008 in Adult Patients with Pemphigus Vulgaris", ClinicalTrials.gov, (Mar. 10, 2016).
Proenca, F., et al., "A simple and eco-friendly approach for the synthesis of 2-imino and 2-oxo-2H-chromene-3-carboxamides," Green Chemistry, vol. 10, pp. 995-998 (2008).
Rellos, P., et al., "Structure and Regulation of the Human Nek2 Centrosomal Kinase," Journal of Biological Chemistry, vol. 282, No. 9, pp. 6833-6842 (2007).
Robak, T., et al., "Tyrosine kinase inhibitors as potential drugs for B-cell lymphoid malignancies and autoimmune disorders," Expert Opinion on Investigational Drugs, vol. 21, No. 7, pp. 921-947 (2012).
Rodeghiero, F., "A critical appraisal of the evidence for the role of splenectomy in adults and children with ITP," British Journal of Haematology, vol. 181, No. 2, pp. 183-195 (2018).
Sadeghi, F., et al., "The influence of drug type of the release profiles from Surelease-coated pellets," International Journal of Pharmaceuticals, vol. 254, pp. 123-135 (2003).
Sammes, M., et al., "α-Cyano-sulphonyl Chlorides: Their Preparation and Reactions with Amines, Alcohols, and Enamines," Journal of the Chemical Society, pp. 2151-2155 (1971).
Sanofi Press Release: Rilzabrutinib LUNA 3 phase 3 study met primary endpoint in immune thrombocytopenia, Apr. 23, 2024.
Santilli, A., et al., "8,9,10,11-Tetrahydro-12H-benzo[5,6]quinoxalino[2,3-e][1,4]diazepin-12-ones. Examples of a New Heterocyclic Ring System," Journal of Organic Chemistry, vol. 29, pp. 2066-2068 (1964).
Santus, G., et al., "Osmotic Drug Delivery: A Review of the Patent Literature," Journal of Controlled Release, vol. 35, pp. 1-21 (1995).
Schwarz, J., et al., "Novel Cyclopropyl β-Amino Acid Analogues of Pregabalin and Gabapentin That Target the α2-0 Protein," Journal of Medicinal Chemistry, vol. 48, pp. 3026-3035 (2005).
Schwobel, J., et al., "Prediction of Michael-Type Acceptor Reactivity toward Glutathione," Chemical Research in Toxicology, vol. 23, pp. 1576-1585 (2010).
Smith, P., et al., "A phase I trial of PRN1008, a novel reversible covalent inhibitor of Bruton's tyrosine kinase, in healthy volunteers: A phase I study of PRN1008", British Journal of Clinical Pharmacology, vol. 83, No. 11, pp. 2367-2376 (Aug. 1, 2017).
Stahl, P., et al., (Eds.) Handbook of Pharmaceutical Salts: Properties, Selection, and Use, Wiley-VCH; pp. 1-374 (2002).
Stevens, C., et al., "Synthesis of Substituted Cyclopropylphosphonates by Michael Induced Ring Closure (MIRC) Reactions," Synlett, vol. 7, pp. 1089-1092 (2002).
Stone, J., et al., "Recommendations for the nomenclature of IgG4-related disease and its individual organ system manifestations", Arthritis & Rheumatism, vol. 64, No. 10, pp. 3016-3067 (2012).
Structure-Based Search Results (May 10, 2011, 10:04 AM), SciFinder.

\* cited by examiner

METHODS FOR TREATING IMMUNE THROMBOCYTOPENIA BY ADMINISTERING (R)-2-[3-[4-AMINO-3-(2-FLUORO-4-PHENOXY-PHENYL)PYRAZOLO[3,4-D]PYRIMIDIN-1-YL] PIPERIDINE-1-CARBONYL]-4-METHYL-4-[4-(OXETAN-3-YL)PIPERAZIN-1-YL]PENT-2-ENENITRILE

CROSS-REFERENCE TO RELATED APPLICATIONS

This application is a continuation of U.S. application Ser. No. 17/069,218 filed on Oct. 13, 2020, which claims priority to U.S. Provisional Application No. 62/914,688, filed on Oct. 14, 2019, and U.S. Provisional Application No. 62/951,302, filed on Dec. 20, 2019, the contents of each of which are incorporated herein by reference in their entirety.

Disclosed herein are methods for treating immune thrombocytopenia. BTK inhibitors and pharmaceutical compositions comprising the same are also disclosed.

Immune thrombocytopenia, commonly referred to as ITP, is a rare autoimmune disease that causes high risk for bleeding, excessive bruising, and fatigue, as well as the potential for life threatening intracranial bleeding due to destruction of platelets. ITP is characterized by immune-mediated (e.g., autoantibody-mediated) platelet destruction and impaired platelet production, resulting in thrombocytopenia, a predisposition to bleeding associated with morbidity and mortality, and adverse impact on patient quality of life (QOL).

Current therapies for adults with ITP include initial treatment with intravenous immunoglobulin (IVIG) and corticosteroids, and subsequent treatment with splenectomy, thrombopoietin receptor agonists (TPO-RAs), rituximab, fostamatinib, and other immunosuppressive therapies (such as, e.g., mycophenolate mofetil (MMF) and cyclosporine). In general, pharmacotherapy (e.g., corticosteroids, IVIG, or anti-D immunoglobulin therapy) is used for symptomatic patients with low platelet counts for reducing platelet destruction. While most patients respond initially to corticosteroids, the rate of continued remission is low. Second line therapies for ITP include rituximab and splenectomy, which are associated with risk of sepsis and immune suppression. Additionally, thrombopoietin (TPO) mimetics (Bussel 2007) are approved for the treatment of patients with chronic ITP who have not had sufficient responses to corticosteroids, IVIG, or splenectomy.

Novel, safe, and effective oral treatments to maintain platelet counts in ITP patients would represent a significant therapeutic advantage over current standard of care. Illustratively, unmet needs in relapsed and refractory ITP include: improving remission rates and durability; avoiding rapid increase of platelet counts/thrombosis risk; steroid-free regimens; and a tolerable and safe therapy that ensures good patient QOL. Thus, there is a need for novel oral therapies for treating ITP, including relapsed and refractory ITP, that address some or all of these limitations of existing therapeutic modalities.

Bruton's agammaglobulinemia tyrosine kinase (BTK) is an essential signaling element downstream of the B-cell receptor (BCR), Fc-gamma receptor (FcγR), and Fc-epsilon receptor (FcεR). BTK is a non-receptor tyrosine kinase and a member of the TEC family of kinases. BTK is essential to B cell lineage maturation, and inhibition of BTK activity in cells produces phenotypic changes consistent with blockade of the BCR. Illustratively, BTK inhibition results in the down-regulation of various B-cell activities, including cell proliferation, differentiation, maturation, and survival, and the up-regulation of apoptosis.

Rather than acting in an "on/off switch" manner, BTK may be best viewed as an immune function "modulator" (Crofford L J et al., 2016; Pal Singh S et al., 2018). Important insights into BTK function come from loss of function analyses in humans and mice. Individuals with loss of function mutations in the BTK gene develop X-linked agammaglobulinemia (XLA), characterized by a complete absence of circulating B cells and plasma cells, and very low levels of immunoglobulins of all classes (Tsukada 1993, Vetrie 1993). This indicates the potential for BTK inhibition to suppress production of autoantibodies thought to be important in the development of autoimmune diseases, such as, e.g., ITP.

While BTK is not expressed in T cells, natural killer cells, and plasma cells and has no traceable direct functions in T cells and plasma cells (Sideras and Smith 1995; Mohamed et al., 2009), the enzyme regulates the activation of other hematopoietic cells, such as basophils, mast cells, macrophages, neutrophils, and platelets. For example, BTK plays a role in the activation of neutrophils, which are key players in the inflammatory response that contributes to wound healing but may also cause tissue damage (Volmering S et al., 2016).

Accordingly, a selective BTK inhibitor has the potential to target multiple pathways involved in inflammation and autoimmunity, including, but not limited to: blocking BCR; inhibiting plasma cell differentiation and antibody production; blocking IgG-mediated FcγR activation, phagocytosis, and inflammatory mediators in monocytes or macrophages; blocking IgE-mediated FcεR activation and degranulation in mast cells or basophils; and inhibiting activation, adhesion, recruitment, and oxidative burst in neutrophils. Based on these effects, a selective BTK inhibitor may block the initiation and progression of various inflammatory diseases and mitigate tissue damage resulting from these diseases. Although individuals with loss of function mutations in the BTK gene have decreased humoral immunity and are susceptible to pyogenic bacterial and enterovirus infections, requiring treatment with intravenous immunoglobulin, inhibition of BTK in individuals with an intact immune system is not predicted to produce similar susceptibility to infection.

Several orally administered BTK inhibitors (BTKi), including ibrutinib (PCI-32765) and spebrutinib (CC-292), are currently marketed or in clinical development for a range of indications (Lee A et al., 2017). For example, ibrutinib has provided further clinical validation of the BTK target and was recently approved for human use in mantle cell lymphoma, Waldenstrom's macroglobulinemia, and chronic lymphocytic leukemia by the U.S. Food and Drug Administration (FDA). Ibrutinib has also demonstrated activity in other hematological malignancies (Wang 2013, Byrd 2013, Imbruvica Package Insert, 2015). In addition, CC-292 has been reported to be well tolerated in a healthy volunteer population at doses which provide 100% occupancy of the BTK enzyme (Evans 2013). Furthermore, evobrutinib recently demonstrated efficacy for multiple sclerosis in a Phase 2 trial (Montalban X et al., 2019). Other BTKi compounds are in clinical development for various immune-mediated disorders, such as pemphigus (NCT02704429), rheumatoid arthritis (NCT03823378, NCT03682705, NCT03233230), and asthma (NCT03944707) (Montalban X et al., 2019; Norman P 2016; Tam C S et al., 2018; Crawford J J et al., 2018; Min T K et al., 2019; Gillooly K M 2017; Nadeem A et al., 2019).

While covalent BTKi, such as ibrutinib and acalabrutinib, improved on the selectivity issues that plagued many first-generation kinase inhibitors, these inhibitors are typically irreversible, causing permanent modification of both on- and off-target kinases and side effects such as thrombocytopenia, anemia, platelet aggregation, and hepatotoxicity (RITUXAN Prescribing Information, 2018; Drug Record Kinase Inhibitors, 2019; Khan Y et al., 2019; Paydas S, 2019; IMBRUVICA, 2013; Rigg R A et al., 2016; Tang C P S et al., 2018). Thus, there is a need for treatment modalities for immune-mediated diseases, such as, e.g., ITP, based on BTKi with reduced side effects.

Compound (I) is a BTK inhibitor of the following structure:

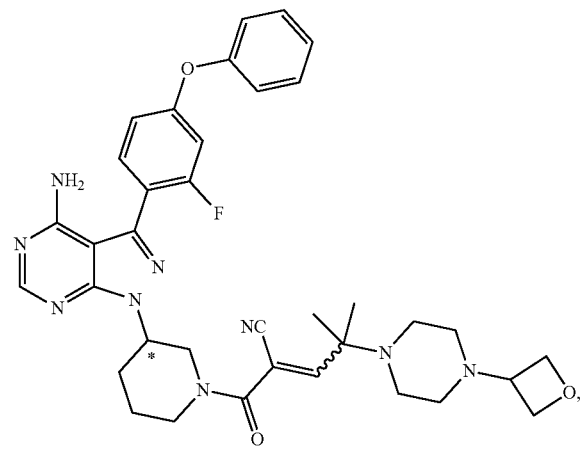 [SMILES: CC(C)(C=C(C#N)C(=O)N1CCCC(Nc2ncnc(N)c2C(=N)c2ccc(Oc3ccccc3)cc2F)C1)N1CCN(C2COC2)CC1]

wherein *C is a stereochemical center. See PCT Publication No. WO 2014/039899, which is incorporated herein by reference, e.g., Example 31.

(R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, having the following structure:

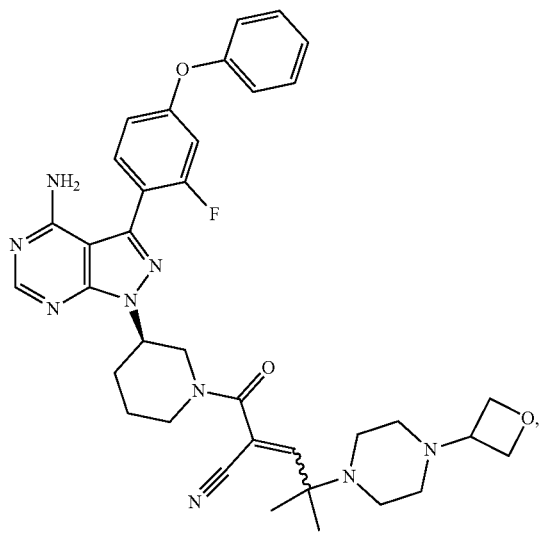 [SMILES: CC(C)(C=C(C#N)C(=O)N1CCC[C@@H](n2nc(-c3ccc(Oc4ccccc4)cc3F)c3c(N)ncnc32)C1)N1CCN(C2COC2)CC1]

is also known as PRN1008 and rilzabrutinib. This compound has been disclosed in several patent publications, such as, e.g., PCT Publication Nos. WO 2014/039899, WO 2015/127310, WO 2016/100914, WO 2016/105531, and WO 2018/005849, the contents of each of which are incorporated by reference herein.

PRN1008 is a novel, highly selective, small molecule inhibitor of non-T cell white blood cell signaling via B-cell receptor, FCγR, and/or FcεR signaling of the BTK pathway. PRN1008 functions as a reversible covalent BTK inhibitor and forms both a non-covalent and a covalent bond with its target, allowing for enhanced selectivity and extended inhibition with low systemic exposure. In comparison to first and second generation BTKi, PRN1008 has shown minimal cross-reactivity with other molecules and is low risk for off-target effects (Smith P F et al., 2017). Importantly, PRN1008's reversible binding minimizes the likelihood of permanently modified peptides (Serafimova I M 2012). In addition, PRN1008 shows improved kinase selectivity relative to the covalent BTK inhibitor ibrutinib, with PRN1008 (1 μM) achieving >90% inhibition for 6 kinases compared to 21 kinases for ibrutinib (1 μM) in a 251-kinase panel.

PRN1008 has shown encouraging results for the treatment of immune-mediated diseases. PRN1008 is the most advanced BTKi in development for an autoimmune disease (Phase 3, NCT03762265) and the first BTKi to be evaluated in the treatment of pemphigus, a blistering disease that, like ITP, is autoantibody-driven. In humans, PRN1008 is rapidly absorbed following oral administration, with a fast half-life (3-4 h) and variable pharmacokinetics (PK).

In Phase 1 studies of PRN1008 with 114 healthy volunteers, target BTK occupancy levels were safely and consistently exceeded, suggesting PRN1008 may be highly effective in treating autoimmune diseases. Moreover, preclinical and clinical PK/PD data showed that treatment effects endured even after the compound was cleared from circulation, consistent with an extended target residence time (Hill R et al., 2015) and high occupancy rate (>90% within four hours) (Smith P F et al., 2015.)

PRN1008 has also demonstrated a favorable safety profile. Based on preclinical reproductive toxicity studies, PRN1008 is not expected to harm fetal development or male fertility. In a Phase 1 study in healthy volunteers, the most commonly reported adverse events were gastrointestinal adverse events, including nausea/vomiting and diarrhea. No serious adverse events or deaths were reported, and no participants discontinued treatment due to an adverse event (Smith P F 2017).

There is preliminary evidence to support the role of BTK inhibition in patients with autoimmune cytopenias (Rogers 2016, Montillo 2017), where sequential episodes of severe autoimmune hemolytic anemia and ITP ceased after initiation of treatment with ibrutinib, a BTK/EGFR/ITK inhibitor, in patients with chronic lymphatic leukemia (CLL). Additionally, and pertinent to the treatment of ITP, PRN1008 treatment in vitro profoundly inhibits human B cell activation and blocks antibody (IgG, IgE) mediated activation of immune cells via Fc receptor signaling. In nonclinical studies, PRN1008 demonstrates a significant dose dependent reduction of platelet-loss (consumption) in a mouse model of immune thrombocytopenia. PRN1008 also shows rapid and significant anti-inflammatory effects in a rat collagen-induced arthritis model, a rat antibody-mediated arthus model, spontaneous canine pemphigus foliaceus, and human pemphigus vulgaris (PV).

Disclosed herein are methods for treating immune thrombocytopenia (ITP) in a human patient in need thereof comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period.

In some embodiments, the treatment period is 8 days. In some embodiments, the treatment period is 28 days. In some embodiments, the treatment period is 84 days. In some embodiments, the treatment period is 168 days.

In some embodiments, the treatment period is at least 8 days. In some embodiments, the treatment period is at least 28 days. In some embodiments, the treatment period is at least 84 days. In some embodiments, the treatment period is at least 168 days.

In some embodiments, the treatment period is from 8 days to 28 days. In some embodiments, the treatment period is from 8 days to 84 days. In some embodiments, the treatment period is from 8 days to 168 days. In some embodiments, the treatment period is from 28 days to 84 days. In some embodiments, the treatment period is from 28 days to 168 days. In some embodiments, the treatment period is from 84 days to 168 days.

In some embodiments, the methods comprise administering to the human patient 400 mg of at least one compound chosen from PRN1008 and pharmaceutically acceptable salts thereof once a day or twice a day. In some embodiments, the methods comprise administering to the human patient 400 mg of at least one compound chosen from PRN1008 and pharmaceutically acceptable salts thereof once a day. In some embodiments, the methods comprise administering to the human patient 400 mg of at least one compound chosen from PRN1008 and pharmaceutically acceptable salts thereof twice a day.

In some embodiments, the methods comprise administering to the human patient 300 mg of at least one compound chosen from PRN1008 and pharmaceutically acceptable salts thereof twice a day.

In some embodiments, the methods comprise treating primary ITP. In some embodiments, the methods comprise treating secondary ITP. In some embodiments, the methods comprise treating chronic ITP. In some embodiments, the methods comprise treating relapsing ITP. In some embodiments, the methods comprise treating refractory ITP.

In some embodiments, the human patient has at least one characteristic prior to the start of the treatment period chosen from:
  an age of from 18 years to 80 years;
  no available and approved therapeutic options;
  a platelet count of less than 30,000/µL;
  an ITP duration of at least one month;
  a history of taking at least one prior ITP therapy; and
  splenectomy.

In some embodiments, the at least one compound chosen from PRN1008 and pharmaceutically acceptable salts thereof is administered as a monotherapy.

In some embodiments, the at least one compound chosen from PRN1008 and pharmaceutically acceptable salts thereof is administered in combination with at least one concomitant ITP therapy.

Also disclosed herein are methods for increasing a platelet count in a human patient with immune thrombocytopenia (ITP) comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period.

In some embodiments, the methods comprise increasing at least 2 consecutive platelet counts relative to a pre-administration baseline platelet count. In some embodiments, the methods comprise increasing at least 2 consecutive platelet counts relative to a pre-administration baseline platelet count without requiring rescue medication.

In some embodiments, the methods comprise increasing a platelet count by at least 5,000/µL relative to a pre-administration baseline platelet count. In some embodiments, the methods comprise increasing a platelet count by at least 10,000/µL relative to a pre-administration baseline platelet count. In some embodiments, the methods comprise increasing a platelet count by at least 15,000/µL relative to a pre-administration baseline platelet count. In some embodiments, the methods comprise increasing a platelet count by at least 20,000/µL relative to a pre-administration baseline platelet count.

In some embodiments, the methods comprise increasing at least 30% of platelet counts measured during the treatment period by at least 20,000/µL relative to a pre-administration baseline platelet count. In some embodiments, the methods comprise increasing at least 40% of platelet counts measured during the treatment period by at least 20,000/µL relative to a pre-administration baseline platelet count. In some embodiments, the methods comprise increasing at least 50% of platelet counts measured during the treatment period by at least 20,000/µL relative to a pre-administration baseline platelet count. In some embodiments, the methods comprise increasing at least 60% of platelet counts measured during the treatment period by at least 20,000/µL relative to a pre-administration baseline platelet count. In some embodiments, the methods comprise increasing at least 70% of platelet counts measured during the treatment period by at least 20,000/µL relative to a pre-administration baseline platelet count.

In some embodiments, the methods comprise increasing at least 2 of the final 8 platelet counts measured during the treatment period by at least 20,000/µL relative to a pre-administration baseline platelet count. In some embodiments, the methods comprise increasing at least 3 of the final 8 platelet counts measured during the treatment period by at least 20,000/µL relative to a pre-administration baseline platelet count. In some embodiments, the methods comprise increasing at least 4 of the final 8 platelet counts measured during the treatment period by at least 20,000/µL relative to a pre-administration baseline platelet count. In some embodiments, the methods comprise increasing at least 5 of the final 8 platelet counts measured during the treatment period by at least 20,000/µL relative to a pre-administration baseline platelet count. In some embodiments, the methods comprise increasing at least 6 of the final 8 platelet counts measured during the treatment period by at least 20,000/µL relative to a pre-administration baseline platelet count. In some embodiments, the methods comprise increasing at least 7 of the final 8 platelet counts measured during the treatment period by at least 20,000/µL relative to a pre-administration baseline platelet count.

In some embodiments, the methods comprise increasing at least 2 of the final 6 platelet counts measured during the treatment period by at least 20,000/µL relative to a pre-administration baseline platelet count. In some embodiments, the methods comprise increasing at least 3 of the final 6 platelet counts measured during the treatment period by at least 20,000/µL relative to a pre-administration baseline platelet count. In some embodiments, the methods comprise increasing at least 4 of the final 6 platelet counts measured during the treatment period by at least 20,000/µL relative to a pre-administration baseline platelet count. In some embodiments, the methods comprise increasing at least 5 of the final 6 platelet counts measured during the treatment period by at least 20,000/μL relative to a pre-administration baseline platelet count.

In some embodiments, the pre-administration baseline platelet count is an average of the human patient's two most recent platelet counts prior to the start of the treatment period and the human patient's platelet count on the first day of the treatment period. In some embodiments, the pre-administration baseline platelet count is an average of the human patient's two most recent platelet counts prior to the start of the treatment period, wherein the two counts are measured no sooner than 7 days apart, and the human patient's platelet count on the first day of the treatment period. In some embodiments, the pre-administration baseline platelet count is an average of the human patient's two most recent platelet counts prior to the start of the treatment period, wherein the two counts are measured no sooner than 7 days apart in the 15 days prior to the start of the treatment period, and the human patient's platelet count on the first day of the treatment period.

In some embodiments, consecutive platelet counts are measured at least 5 days apart.

In some embodiments, the treatment period is 8 days. In some embodiments, the treatment period is 28 days. In some embodiments, the treatment period is 84 days. In some embodiments, the treatment period is 168 days.

In some embodiments, the treatment period is at least 8 days. In some embodiments, the treatment period is at least 28 days. In some embodiments, the treatment period is at least 84 days. In some embodiments, the treatment period is at least 168 days.

In some embodiments, the treatment period is from 8 days to 28 days. In some embodiments, the treatment period is from 8 days to 84 days. In some embodiments, the treatment period is from 8 days to 168 days. In some embodiments, the treatment period is from 28 days to 84 days. In some embodiments, the treatment period is from 28 days to 168 days. In some embodiments, the treatment period is from 84 days to 168 days.

In some embodiments, the methods comprise administering to the human patient 400 mg of at least one compound chosen from PRN1008 and pharmaceutically acceptable salts thereof once a day or twice a day. In some embodiments, the methods comprise administering to the human patient 400 mg of at least one compound chosen from PRN1008 and pharmaceutically acceptable salts thereof once a day. In some embodiments, the methods comprise administering to the human patient 400 mg of at least one compound chosen from PRN1008 and pharmaceutically acceptable salts thereof twice a day.

In some embodiments, the methods comprise administering to the human patient 300 mg of at least one compound chosen from PRN1008 and pharmaceutically acceptable salts thereof twice a day.

In some embodiments, the human patient has primary ITP. In some embodiments, the human patient has secondary ITP. In some embodiments, the human patient has chronic ITP. In some embodiments, the human patient has relapsing ITP. In some embodiments, the human patient has refractory ITP.

In some embodiments, the human patient has at least one characteristic prior to the start of the treatment period chosen from:
- an age of from 18 years to 80 years;
- no available and approved therapeutic options;
- a platelet count of less than 30,000/μL;
- an ITP duration of at least one month;
- a history of taking at least one prior ITP therapy; and
- splenectomy.

In some embodiments, the at least one compound chosen from PRN1008 and pharmaceutically acceptable salts thereof is administered as a monotherapy.

In some embodiments, the at least one compound chosen from PRN1008 and pharmaceutically acceptable salts thereof is administered in combination with at least one concomitant ITP therapy.

Also disclosed herein are methods for achieving a platelet count of at least 50,000/μL in a human patient with immune thrombocytopenia (ITP) comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period.

In some embodiments, the methods comprise achieving at least 2 platelet counts of at least 50,000/μL. In some embodiments, the methods comprise achieving at least 2 platelet counts of at least 50,000/μL without requiring rescue medication.

In some embodiments, the methods comprise achieving at least 2 consecutive platelet counts of at least 50,000/μL. In some embodiments, the methods comprise achieving at least 2 consecutive platelet counts of at least 50,000/μL without requiring rescue medication.

In some embodiments, the methods comprise achieving a platelet count of at least 50,000/μL in at least 30% of platelet counts measured during the treatment period. In some embodiments, the methods comprise achieving a platelet count of at least 50,000/μL in at least 35% of platelet counts measured during the treatment period. In some embodiments, the methods comprise achieving a platelet count of at least 50,000/μL in at least 40% of platelet counts measured during the treatment period. In some embodiments, the methods comprise achieving a platelet count of at least 50,000/μL in at least 45% of platelet counts measured during the treatment period. In some embodiments, the methods comprise achieving a platelet count of at least 50,000/μL in at least 50% of platelet counts measured during the treatment period. In some embodiments, the methods comprise achieving a platelet count of at least 50,000/μL in at least 55% of platelet counts measured during the treatment period. In some embodiments, the methods comprise achieving a platelet count of at least 50,000/μL in at least 60% of platelet counts measured during the treatment period. In some embodiments, the methods comprise achieving a platelet count of at least 50,000/μL in at least 65% of platelet counts measured during the treatment period. In some embodiments, the methods comprise achieving a platelet count of at least 50,000/μL in at least 70% of platelet counts measured during the treatment period.

In some embodiments, the methods comprise achieving a platelet count of at least 50,000/μL in at least 2 of the final 8 platelet counts measured during the treatment period. In some embodiments, the methods comprise achieving a platelet count of at least 50,000/μL in at least 3 of the final 8 platelet counts measured during the treatment period. In some embodiments, the methods comprise achieving a platelet count of at least 50,000/μL in at least 4 of the final 8 platelet counts measured during the treatment period. In some embodiments, the methods comprise achieving a platelet count of at least 50,000/μL in at least 5 of the final 8 platelet counts measured during the treatment period. In some embodiments, the methods comprise achieving a platelet count of at least 50,000/μL in at least 6 of the final 8 platelet counts measured during the treatment period. In some embodiments, the methods comprise achieving a platelet count of at least 50,000/μL in at least 7 of the final 8 platelet counts measured during the treatment period.

In some embodiments, the methods comprise achieving a platelet count of at least 50,000/μL in at least 2 of the final 6 platelet counts measured during the treatment period. In some embodiments, the methods comprise achieving a platelet count of at least 50,000/μL in at least 3 of the final 6 platelet counts measured during the treatment period. In some embodiments, the methods comprise achieving a platelet count of at least 50,000/μL in at least 4 of the final 6 platelet counts measured during the treatment period. In some embodiments, the methods comprise achieving a platelet count of at least 50,000/μL in at least 5 of the final 6 platelet counts measured during the treatment period.

In some embodiments, the methods comprise increasing at least 30% of platelet counts measured during the treatment period by at least 20,000/μL relative to a pre-administration baseline platelet count. In some embodiments, the methods comprise increasing at least 40% of platelet counts measured during the treatment period by at least 20,000/μL relative to a pre-administration baseline platelet count. In some embodiments, the methods comprise increasing at least 50% of platelet counts measured during the treatment period by at least 20,000/μL relative to a pre-administration baseline platelet count. In some embodiments, the methods comprise increasing at least 60% of platelet counts measured during the treatment period by at least 20,000/μL relative to a pre-administration baseline platelet count. In some embodiments, the methods comprise increasing at least 70% of platelet counts measured during the treatment period by at least 20,000/μL relative to a pre-administration baseline platelet count.

In some embodiments, the methods comprise increasing at least 2 of the final 8 platelet counts measured during the treatment period by at least 20,000/μL relative to a pre-administration baseline platelet count. In some embodiments, the methods comprise increasing at least 3 of the final 8 platelet counts measured during the treatment period by at least 20,000/μL relative to a pre-administration baseline platelet count. In some embodiments, the methods comprise increasing at least 4 of the final 8 platelet counts measured during the treatment period by at least 20,000/μL relative to a pre-administration baseline platelet count. In some embodiments, the methods comprise increasing at least 5 of the final 8 platelet counts measured during the treatment period by at least 20,000/μL relative to a pre-administration baseline platelet count. In some embodiments, the methods comprise increasing at least 6 of the final 8 platelet counts measured during the treatment period by at least 20,000/μL relative to a pre-administration baseline platelet count. In some embodiments, the methods comprise increasing at least 7 of the final 8 platelet counts measured during the treatment period by at least 20,000/μL relative to a pre-administration baseline platelet count.

In some embodiments, the methods comprise increasing at least 2 of the final 6 platelet counts measured during the treatment period by at least 20,000/μL relative to a pre-administration baseline platelet count. In some embodiments, the methods comprise increasing at least 3 of the final 6 platelet counts measured during the treatment period by at least 20,000/μL relative to a pre-administration baseline platelet count. In some embodiments, the methods comprise increasing at least 4 of the final 6 platelet counts measured during the treatment period by at least 20,000/μL relative to a pre-administration baseline platelet count. In some embodiments, the methods comprise increasing at least 5 of the final 6 platelet counts measured during the treatment period by at least 20,000/μL relative to a pre-administration baseline platelet count.

In some embodiments, the pre-administration baseline platelet count is an average of the human patient's two most recent platelet counts prior to the start of the treatment period and the human patient's platelet count on the first day of the treatment period. In some embodiments, the pre-administration baseline platelet count is an average of the human patient's two most recent platelet counts prior to the start of the treatment period, wherein the two counts are measured no sooner than 7 days apart, and the human patient's platelet count on the first day of the treatment period. In some embodiments, the pre-administration baseline platelet count is an average of the human patient's two most recent platelet counts prior to the start of the treatment period, wherein the two counts are measured no sooner than 7 days apart in the 15 days prior to the start of the treatment period, and the human patient's platelet count on the first day of the treatment period.

In some embodiments, consecutive platelet counts are measured at least 5 days apart.

In some embodiments, the treatment period is 8 days. In some embodiments, the treatment period is 28 days. In some embodiments, the treatment period is 84 days. In some embodiments, the treatment period is 168 days.

In some embodiments, the treatment period is at least 8 days. In some embodiments, the treatment period is at least 28 days. In some embodiments, the treatment period is at least 84 days. In some embodiments, the treatment period is at least 168 days.

In some embodiments, the treatment period is from 8 days to 28 days. In some embodiments, the treatment period is from 8 days to 84 days. In some embodiments, the treatment period is from 8 days to 168 days. In some embodiments, the treatment period is from 28 days to 84 days. In some embodiments, the treatment period is from 28 days to 168 days. In some embodiments, the treatment period is from 84 days to 168 days.

In some embodiments, the methods comprise administering to the human patient 400 mg of at least one compound chosen from PRN1008 and pharmaceutically acceptable salts thereof once a day or twice a day. In some embodiments, the methods comprise administering to the human patient 400 mg of at least one compound chosen from PRN1008 and pharmaceutically acceptable salts thereof once a day. In some embodiments, the methods comprise administering to the human patient 400 mg of at least one compound chosen from PRN1008 and pharmaceutically acceptable salts thereof twice a day.

In some embodiments, the methods comprise administering to the human patient 300 mg of at least one compound chosen from PRN1008 and pharmaceutically acceptable salts thereof twice a day.

In some embodiments, the human patient has primary ITP. In some embodiments, the human patient has secondary ITP. In some embodiments, the human patient has chronic ITP. In some embodiments, the human patient has relapsing ITP. In some embodiments, the human patient has refractory ITP.

In some embodiments, the human patient has at least one characteristic prior to the start of the treatment period chosen from:
an age of from 18 years to 80 years;
no available and approved therapeutic options;
a platelet count of less than 30,000/μL;

an ITP duration of at least one month;
a history of taking at least one prior ITP therapy; and
splenectomy.

In some embodiments, the at least one compound chosen from PRN1008 and pharmaceutically acceptable salts thereof is administered as a monotherapy.

In some embodiments, the at least one compound chosen from PRN1008 and pharmaceutically acceptable salts thereof is administered in combination with at least one concomitant ITP therapy.

Also disclosed herein are methods for achieving at least one platelet count of at least 50,000/µL and increasing at least one platelet count by at least 20,000/µL in a human patient with immune thrombocytopenia (ITP) comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period.

In some embodiments, the methods comprise achieving at least 2 platelet counts of at least 50,000/µL. In some embodiments, the methods comprise achieving at least 2 platelet counts of at least 50,000/µL without requiring rescue medication.

In some embodiments, the methods comprise achieving at least 2 consecutive platelet counts of at least 50,000/µL. In some embodiments, the methods comprise achieving at least 2 consecutive platelet counts of at least 50,000/µL without requiring rescue medication.

In some embodiments, the methods comprise achieving a platelet count of at least 50,000/µL in at least 30% of platelet counts measured during the treatment period. In some embodiments, the methods comprise achieving a platelet count of at least 50,000/µL in at least 35% of platelet counts measured during the treatment period. In some embodiments, the methods comprise achieving a platelet count of at least 50,000/µL in at least 40% of platelet counts measured during the treatment period. In some embodiments, the methods comprise achieving a platelet count of at least 50,000/µL in at least 45% of platelet counts measured during the treatment period. In some embodiments, the methods comprise achieving a platelet count of at least 50,000/µL in at least 50% of platelet counts measured during the treatment period. In some embodiments, the methods comprise achieving a platelet count of at least 50,000/µL in at least 55% of platelet counts measured during the treatment period. In some embodiments, the methods comprise achieving a platelet count of at least 50,000/µL in at least 60% of platelet counts measured during the treatment period. In some embodiments, the methods comprise achieving a platelet count of at least 50,000/µL in at least 65% of platelet counts measured during the treatment period. In some embodiments, the methods comprise achieving a platelet count of at least 50,000/µL in at least 70% of platelet counts measured during the treatment period.

In some embodiments, the methods comprise achieving a platelet count of at least 50,000/µL in at least 2 of the final 8 platelet counts measured during the treatment period. In some embodiments, the methods comprise achieving a platelet count of at least 50,000/µL in at least 3 of the final 8 platelet counts measured during the treatment period. In some embodiments, the methods comprise achieving a platelet count of at least 50,000/µL in at least 4 of the final 8 platelet counts measured during the treatment period. In some embodiments, the methods comprise achieving a platelet count of at least 50,000/µL in at least 5 of the final 8 platelet counts measured during the treatment period. In some embodiments, the methods comprise achieving a platelet count of at least 50,000/µL in at least 6 of the final 8 platelet counts measured during the treatment period. In some embodiments, the methods comprise achieving a platelet count of at least 50,000/µL in at least 7 of the final 8 platelet counts measured during the treatment period.

In some embodiments, the methods comprise achieving a platelet count of at least 50,000/µL in at least 2 of the final 6 platelet counts measured during the treatment period. In some embodiments, the methods comprise achieving a platelet count of at least 50,000/µL in at least 3 of the final 6 platelet counts measured during the treatment period. In some embodiments, the methods comprise achieving a platelet count of at least 50,000/µL in at least 4 of the final 6 platelet counts measured during the treatment period. In some embodiments, the methods comprise achieving a platelet count of at least 50,000/µL in at least 5 of the final 6 platelet counts measured during the treatment period.

In some embodiments, consecutive platelet counts are measured at least 5 days apart.

In some embodiments, the treatment period is 8 days. In some embodiments, the treatment period is 28 days. In some embodiments, the treatment period is 84 days. In some embodiments, the treatment period is 168 days.

In some embodiments, the treatment period is at least 8 days. In some embodiments, the treatment period is at least 28 days. In some embodiments, the treatment period is at least 84 days. In some embodiments, the treatment period is at least 168 days.

In some embodiments, the treatment period is from 8 days to 28 days. In some embodiments, the treatment period is from 8 days to 84 days. In some embodiments, the treatment period is from 8 days to 168 days. In some embodiments, the treatment period is from 28 days to 84 days. In some embodiments, the treatment period is from 28 days to 168 days. In some embodiments, the treatment period is from 84 days to 168 days.

In some embodiments, the methods comprise administering to the human patient 400 mg of at least one compound chosen from PRN1008 and pharmaceutically acceptable salts thereof once a day or twice a day. In some embodiments, the methods comprise administering to the human patient 400 mg of at least one compound chosen from PRN1008 and pharmaceutically acceptable salts thereof once a day. In some embodiments, the methods comprise administering to the human patient 400 mg of at least one compound chosen from PRN1008 and pharmaceutically acceptable salts thereof twice a day.

In some embodiments, the methods comprise administering to the human patient 300 mg of at least one compound chosen from PRN1008 and pharmaceutically acceptable salts thereof twice a day.

In some embodiments, the human patient has primary ITP. In some embodiments, the human patient has secondary ITP. In some embodiments, the human patient has chronic ITP. In some embodiments, the human patient has relapsing ITP. In some embodiments, the human patient has refractory ITP.

In some embodiments, the human patient has at least one characteristic prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the at least one compound chosen from PRN1008 and pharmaceutically acceptable salts thereof is administered as a monotherapy.

In some embodiments, the at least one compound chosen from PRN1008 and pharmaceutically acceptable salts thereof is administered in combination with at least one concomitant ITP therapy.

Also disclosed herein are methods for achieving a platelet count of at least 30,000/μL in a human patient with immune thrombocytopenia (ITP) comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period.

In some embodiments, the treatment period is 8 days. In some embodiments, the treatment period is 28 days. In some embodiments, the treatment period is 84 days. In some embodiments, the treatment period is 168 days.

In some embodiments, the treatment period is at least 8 days. In some embodiments, the treatment period is at least 28 days. In some embodiments, the treatment period is at least 84 days. In some embodiments, the treatment period is at least 168 days.

In some embodiments, the treatment period is from 8 days to 28 days. In some embodiments, the treatment period is from 8 days to 84 days. In some embodiments, the treatment period is from 8 days to 168 days. In some embodiments, the treatment period is from 28 days to 84 days. In some embodiments, the treatment period is from 28 days to 168 days. In some embodiments, the treatment period is from 84 days to 168 days.

In some embodiments, the methods comprise administering to the human patient 400 mg of at least one compound chosen from PRN1008 and pharmaceutically acceptable salts thereof once a day or twice a day. In some embodiments, the methods comprise administering to the human patient 400 mg of at least one compound chosen from PRN1008 and pharmaceutically acceptable salts thereof once a day. In some embodiments, the methods comprise administering to the human patient 400 mg of at least one compound chosen from PRN1008 and pharmaceutically acceptable salts thereof twice a day.

In some embodiments, the methods comprise administering to the human patient 300 mg of at least one compound chosen from PRN1008 and pharmaceutically acceptable salts thereof twice a day.

In some embodiments, the human patient has primary ITP. In some embodiments, the human patient has secondary ITP. In some embodiments, the human patient has chronic ITP. In some embodiments, the human patient has relapsing ITP. In some embodiments, the human patient has refractory ITP.

In some embodiments, the human patient has at least one characteristic prior to the start of the treatment period chosen from:
an age of from 18 years to 80 years;
no available and approved therapeutic options;
a platelet count of less than 30,000/μL;
an ITP duration of at least one month;
a history of taking at least one prior ITP therapy; and
splenectomy.

In some embodiments, the at least one compound chosen from PRN1008 and pharmaceutically acceptable salts thereof is administered as a monotherapy.

In some embodiments, the at least one compound chosen from PRN1008 and pharmaceutically acceptable salts thereof is administered in combination with at least one concomitant ITP therapy.

Example Embodiments 1

Without limitation, some embodiments of the disclosure include:

1. A method for treating immune thrombocytopenia (ITP) in a human patient in need thereof comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period, wherein the human patient has at least one characteristic chosen from:
an average plasma count of from 3,000/μL to 33,000/μL for a most recent platelet count prior to the start of the treatment period, a second most recent platelet count prior to the start of the treatment period, and a platelet count on the first day of the treatment period;
a history of taking at least 4 prior ITP therapies prior to the start of the treatment period; and
splenectomy prior to the start of the treatment period.

2. A method for increasing a platelet count in a human patient with immune thrombocytopenia (ITP) comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period, wherein the human patient has at least one characteristic chosen from:
an average plasma count of from 3,000/μL to 33,000/μL for a most recent platelet count prior to the start of the treatment period, a second most recent platelet count prior to the start of the treatment period, and a platelet count on the first day of the treatment period;
a history of taking at least 4 prior ITP therapies prior to the start of the treatment period; and
splenectomy prior to the start of the treatment period.

3. The method according to Embodiment 2, wherein increasing the platelet count comprises increasing a platelet count by at least 20,000/μL relative to a pre-administration baseline platelet count.

4. The method according to Embodiment 2 or 3, wherein increasing the platelet count comprises increasing at least 50% of platelet counts measured during the treatment period by at least 20,000/μL relative to a pre-administration baseline platelet count.

5. The method according to any of Embodiments 2-4, wherein increasing the platelet count comprises increasing at least 2 consecutive platelet counts relative to a pre-administration baseline platelet count.

6. The method according to any of Embodiments 3-5, wherein the pre-administration baseline platelet count is an average of the human patient's two most recent platelet counts prior to the start of the treatment period and the human patient's platelet count on the first day of the treatment period.

7. A method for achieving a platelet count of at least 50,000/μL in a human patient with immune thrombocytopenia (ITP) comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period, wherein the human patient has at least one characteristic chosen from:

an average plasma count of from 3,000/µL to 33,000/µL for a most recent platelet count prior to the start of the treatment period, a second most recent platelet count prior to the start of the treatment period, and a platelet count on the first day of the treatment period;

a history of taking at least 4 prior ITP therapies prior to the start of the treatment period; and splenectomy prior to the start of the treatment period.

8. The method according to Embodiment 7, wherein achieving a platelet count comprises achieving at least 2 platelet counts of at least 50,000/µL.

9. The method according to Embodiment 7 or 8, wherein achieving a platelet count comprises achieving at least 2 consecutive platelet counts of at least 50,000/µL.

10. The method according to any of Embodiments 7-9, wherein achieving a platelet count comprises achieving a platelet count of at least 50,000/µL in at least 50% of platelet counts measured during the treatment period.

11. The method according to any of Embodiments 7-10, wherein achieving a platelet count comprises achieving a platelet count of at least 50,000/µL in at least 4 of the final 8 platelet counts measured during the treatment period.

12. The method according to any of Embodiments 7-11, wherein achieving a platelet count comprises achieving a platelet count of at least 50,000/µL in at least 4 of the final 6 platelet counts measured during the treatment period.

13. A method for achieving at least one platelet count of at least 50,000/µL and increasing at least one platelet count by at least 20,000/µL in a human patient with immune thrombocytopenia (ITP) comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period, wherein the human patient has at least one characteristic chosen from:

an average plasma count of from 3,000/µL to 33,000/µL for a most recent platelet count prior to the start of the treatment period, a second most recent platelet count prior to the start of the treatment period, and a platelet count on the first day of the treatment period;

a history of taking at least 4 prior ITP therapies prior to the start of the treatment period; and splenectomy prior to the start of the treatment period.

14. The method according to Embodiment 13, wherein achieving a platelet count comprises achieving at least 2 platelet counts of at least 50,000/µL.

15. The method according to Embodiment 13 or 14, wherein achieving a platelet count comprises achieving at least 2 consecutive platelet counts of at least 50,000/µL.

16. The method according to any of Embodiments 13-15, wherein achieving a platelet count comprises achieving a platelet count of at least 50,000/µL in at least 50% of platelet counts measured during the treatment period.

17. The method according to any of Embodiments 13-16, wherein achieving a platelet count comprises achieving a platelet count of at least 50,000/µL in at least 4 of the final 8 platelet counts measured during the treatment period.

18. The method according to any of Embodiments 13-17, wherein achieving a platelet count comprises achieving a platelet count of at least 50,000/µL in at least 4 of the final 6 platelet counts measured during the treatment period.

19. The method according to any of Embodiments 13-18, wherein achieving a platelet count comprises increasing at least 50% of platelet counts measured during the treatment period by at least 20,000/µL relative to a pre-administration baseline platelet count.

20. The method according to Embodiment 19, wherein the pre-administration baseline platelet count is an average of the human patient's two most recent platelet counts prior to the start of the treatment period and the human patient's platelet count on the first day of the treatment period.

21. A method for achieving a platelet count of at least 30,000/µL in a human patient with immune thrombocytopenia (ITP) comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period, wherein the human patient has at least one characteristic chosen from:

an average plasma count of from 3,000/µL to 33,000/µL for a most recent platelet count prior to the start of the treatment period, a second most recent platelet count prior to the start of the treatment period, and a platelet count on the first day of the treatment period;

a history of taking at least 4 prior ITP therapies prior to the start of the treatment period; and splenectomy prior to the start of the treatment period.

22. The method according to Embodiment 21, wherein achieving a platelet count comprises achieving a platelet count of at least 30,000/µL in at least 50% of platelet counts measured during the treatment period 23. The method according to Embodiment 21 or 22, wherein achieving a platelet count comprises achieving a platelet count of at least 30,000/µL in at least 75% of platelet counts measured during the treatment period 24. The method according to any of Embodiments 1-23, wherein consecutive platelet counts are measured at least 5 days apart.

25. The method according to any of Embodiments 1-24, wherein the human patient has an average plasma count of from 3,000/µL to 33,000/µL for the most recent platelet count prior to the start of the treatment period, the second most recent platelet count prior to the start of the treatment period, and the platelet count on the first day of the treatment period.

26. The method according to any of Embodiments 1-24, wherein the human patient has an average plasma count of from 3,000/µL to 15,000/µL for the most recent platelet count prior to the start of the treatment period, the second most recent platelet count prior to the start of the treatment period, and the platelet count on the first day of the treatment period.

27. The method according to any of Embodiments 1-26, wherein the human patient has a history of taking at least 4 prior ITP therapies prior to the start of the treatment period.

28. The method according to any of Embodiments 1-27, wherein the human patient had a splenectomy prior to the start of the treatment period.

29. The method according to any of Embodiments 1-28, wherein the human patient has primary ITP.

30. The method according to any of Embodiments 1-28, wherein the human patient has secondary ITP.

31. The method according to any of Embodiments 1-28, wherein the human patient has chronic ITP.
32. The method according to any of Embodiments 1-28, wherein the human patient has relapsing ITP.
33. The method according to any of Embodiments 1-32, wherein the human patient has refractory ITP.
34. The method according to any of Embodiments 1-33, wherein the human patient has no available and approved therapeutic options.
35. The method according to any of Embodiments 1-34, wherein the human patient has a platelet count of less than 30,000/μL prior to the start of the treatment period.
36. The method according to any of Embodiments 1-35, wherein the human patient has 2 platelet counts of less than 30,000/μL prior to the start of the treatment period.
37. The method according to any of Embodiments 1-36, wherein the human patient has 2 platelet counts of less than 30,000/μL prior to the start of the treatment period, wherein the 2 counts are measured no sooner than 7 days apart in the 15 days prior to the start of the treatment period.
38. The method according to any of Embodiments 1-37, wherein the at least 4 prior ITP therapies are chosen from corticosteroids, thrombopoietin receptor agonists, intravenous immunoglobulin, anti-D immunoglobulin, and rituximab.
39. The method according to any of Embodiments 1-38, wherein the treatment period is at least 8 days.
40. The method according to any of Embodiments 1-38, wherein the treatment period is at least 28 days.
41. The method according to any of Embodiments 1-38, wherein the treatment period is at least 84 days.
42. The method according to any of Embodiments 1-38, wherein the treatment period is at least 168 days.
43. The method according to any of Embodiments 1-42, comprising administering to the human patient 400 mg of at least one compound chosen from PRN1008 and pharmaceutically acceptable salts thereof once a day or twice a day.
44. The method according to any of Embodiments 1-43, comprising administering to the human patient 400 mg of at least one compound chosen from PRN1008 and pharmaceutically acceptable salts thereof once a day.
45. The method according to any of Embodiments 1-43, comprising administering to the human patient 400 mg of at least one compound chosen from PRN1008 and pharmaceutically acceptable salts thereof twice a day.
46. The method according to any of Embodiments 1-42, comprising administering to the human patient 300 mg of at least one compound chosen from PRN1008 and pharmaceutically acceptable salts thereof twice a day.
47. The method according to any of Embodiments 1-46, wherein the at least one compound is administered as a monotherapy.
48. The method according to any of Embodiments 1-46, wherein the at least one compound is administered in combination with at least one concomitant ITP therapy.
49. The method according to Embodiment 48, wherein the at least one concomitant ITP therapy is chosen from corticosteroids and thrombopoietin receptor agonists.
50. The method according to Embodiment 48 or 49, wherein the at least one concomitant ITP therapy is chosen from corticosteroids, eltrombopag, and romiplostim.
51. The method according to any of Embodiments 1-50, wherein the at least one compound comprises at least one compound chosen from the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.
52. The method according to any of Embodiments 1-50, wherein the at least one compound comprises at least one compound chosen from the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.
53. The method according to any of Embodiments 1-50, wherein the at least one compound comprises a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt of the foregoing.
54. The method according to any of Embodiments 1-53, wherein the at least one compound is orally administered to the human patient.
55. The method according to any of Embodiments 1-54, wherein the at least one compound is administered to the human patient in the form of at least one tablet.
56. The method according to any of Embodiments 1-55, wherein the at least one compound is administered with a glass of water.
57. The method according to any of Embodiments 1-56, wherein the at least one compound is administered with food.
58. The method according to any of Embodiments 1-56, wherein the at least one compound is administered without food.

Example Embodiments 2

Without limitation, some embodiments of the disclosure include:
1. A method for treating immune thrombocytopenia in a human patient comprising: administering to the patient a dose chosen from 400 mg once daily (QD), 300 mg twice daily (BID), and 400 mg BID of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008).
2. The method according to Embodiment 1, wherein PRN1008 comprises a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile.
3. The method according to Embodiment 1, wherein PRN1008 is formulated as a pharmaceutical composition.
4. The method according to Embodiment 3, wherein the pharmaceutical composition comprises one or more pharmaceutical acceptable carriers or excipients.
5. The method according to Embodiment 4, wherein the pharmaceutical composition comprises microcrystalline cellulose, crospovidone, and sodium stearyl fumarate with a film coating.
6. The method according to Embodiment 1, further comprising repeating the administration of PRN1008 to the patient over a treatment period.
7 The method according to Embodiment 1, wherein the dose is 400 mg BID of PRN1008.
8. The method according to Embodiment 1, wherein the patient is administered an initial dose of 400 mg QD of PRN1008, and after 28 days, the dose is escalated to a higher dose of 300 mg BID or 400 mg BID of PRN1008.

9. The method according to Embodiment 1, wherein the patient is administered an initial dose of 300 mg BID of PRN1008, and after 28 days, the dose is escalated to 400 mg BID of PRN1008.

10. The method according to Embodiment 6, wherein the treatment period is for a period of up to 168 days.

11. The method according to Embodiment 6, wherein the treatment period ranges from 28 days to 168 days.

12. The method according to Embodiment 6, wherein the treatment period is for a minimum of 8 days.

13. The method according to Embodiment 6, wherein the treatment period ranges from 8 days to 28 days.

14. The method according to Embodiment 1, wherein before administration, the patient's platelet count is less than 30,000/μL for two or more consecutive platelet counts.

15. The method according to Embodiment 1, wherein after administration over a treatment period, the patient obtains two or more consecutive platelet counts, separated by at least 5 days, of ≥50,000/μL.

16. The method according to Embodiment 15, wherein the treatment period ranges from 28 days to 168 days.

17. The method according to Embodiment 6, wherein after administration over a treatment period, the patient has a stable response of a platelet count of greater than or equal to 50,000/μL during the treatment period and an increase of platelet count of ≥20,000/μL from baseline.

18. The method according to Embodiment 15, wherein the patient has a rapid onset of response within one to two weeks (7-14 days) corresponding to an increased platelet count of about 50,000/μL to 100,000/μL.

19. The method according to Embodiment 15, wherein the patient has a rapid onset of response within one to two weeks (7-14 days) corresponding to an increased platelet count of 60,000/μL to 90,000/μL 20. The method according to Embodiment 16, wherein the rapid onset of response is within 1 week (7 days).

21. The method according to Embodiment 16, wherein the patient is administered an initial dose of 300 mg BID or 400 mg BID of PRN1008.

22. The method according to Embodiment 1, wherein before administration, the patient has relapsed or refractory idiopathic thrombocytopenia, which is primary or secondary to other diseases afflicting the patient.

23. The method according to Embodiment 1, wherein in the patient has secondary ITP.

24. The method according to Embodiment 21, wherein the patient is administered a dose of 400 mg BID.

25. The method according to Embodiment 1, wherein the patient is also taking one or more concomitant medications.

26. The method according to Embodiment 25, wherein the one or more concomitant medication is chosen from corticosteroids, eltrombopag, and romiplostim.

27. A method for treating immune thrombocytopenia in a human patient comprising: administering to the patient a dose chosen from 400 mg once daily (QD), 300 mg twice daily (BID), and 400 mg BID of 2-[(3R)-3-[4-amino-3-(2-fluoro-4-phenoxy-phenyl)pyrazolo[3,4-d]-pyrimidin-1-yl] piperidine-1-carbonyl]-4-methyl-4-[4-(oxetan-3-yl)piper-azin-1-yl]pent-2-enenitrile (PRN1008), wherein before administration, the patient's platelet count is less than 30,000/μL for two or more consecutive platelet counts, and wherein after administration, the patient has a stable response of a platelet count of greater than or equal to 50,000/μL during the treatment period.

28. The method according to Embodiment 27, wherein the dose is 400 mg BID of PRN1008.

29. A method for treating immune thrombocytopenia in a human patient comprising: administering to the patient a dose chosen from 400 mg once daily (QD), 300 mg twice daily (BID), and 400 mg BID of 2-[(3R)-3-[4-amino-3-(2-fluoro-4-phenoxy-phenyl)pyrazolo[3,4-d]-pyrimidin-1-yl] piperidine-1-carbonyl]-4-methyl-4-[4-(oxetan-3-yl)piper-azin-1-yl]pent-2-enenitrile (PRN1008), wherein before administration, the patient's platelet count is less than 30,000/μL for two or more consecutive platelet counts, and after administration over a treatment period, the patient obtains two or more consecutive platelet counts, separated by at least 5 days, of ≥50,000/μL and an increase of platelet count of ≥20,000/μL from baseline.

30. The method according to Embodiment 29, wherein the dose is 400 mg BID of PRN1008.

DEFINITIONS

Figure 1A:
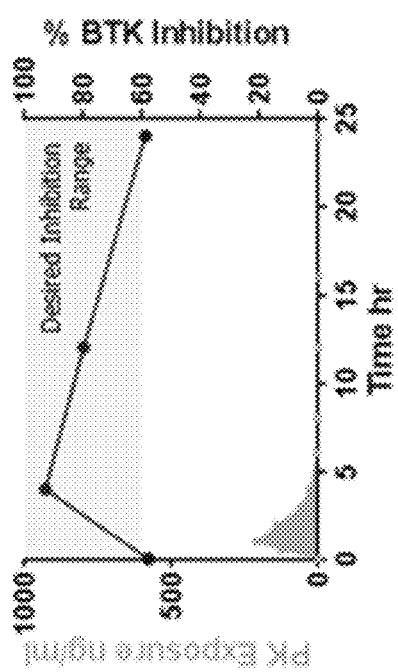
FIG. 1A illustrates PRN1008's reversible covalent binding mechanism, which enables optimized clinical activity with minimal drug exposure and benefits associated with reversibility.
Figure 1B:
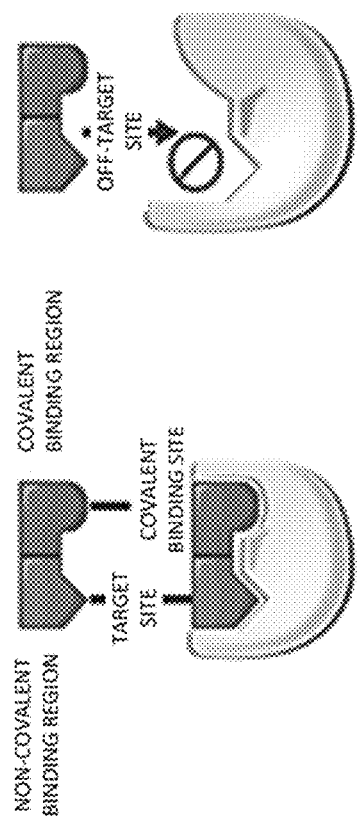
FIG. 1B depicts PK exposure (ng/mL) and % BTK inhibition over 25 h for PRN1008.

Unless otherwise stated, the following terms used in the specification and claims are defined for the purposes of this Application and have the following meanings. All undefined technical and scientific terms used in this Application have the meaning as commonly understood by one of ordinary skill in the art to which this disclosure belongs.

As used herein, "a" or "an" entity refers to one or more of that entity; for example, a compound refers to one or more compounds or at least one compound unless stated otherwise. As such, the terms "a" (or "an"), "one or more", and "at least one" can be used interchangeably herein.

As used herein, the term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. With regard to specific values, it should be understood that specific values described herein for subject populations (e.g., the subject of the described clinical trial) represent median, mean, or statistical numbers, unless otherwise provided. Accordingly, aspects of the present disclosure requiring a particular value in a subject are supported herein by population data in which the relevant value is assessed to be a meaningful delimitation on the subject population.

As used herein, the term "active pharmaceutical ingredient" or "therapeutic agent" ("API") refers to a biologically active compound.

As used herein, the terms "administer," "administering," or "administration" herein refer to providing, giving, dosing, and/or prescribing by either a health practitioner or an authorized agent and/or putting into, taking or consuming by the patient or person himself or herself. For example, "administration" of an API to a patient refers to any route (e.g., oral delivery) of introducing or delivering the API to the patient. Administration includes self administration and administration by another.

As used herein, "BID" and "bid" are used interchangeably to refer to twice a day.

As used herein, "immune thrombocytopenia" (ITP) encompasses or at least also refers to other terms commonly used such as idiopathic thrombocytopenia and idiopathic thrombocytopenic purpura. There are two main types of ITP: short (acute) and chronic (long term). Acute ITP typically lasts less than six months, whereas chronic ITP can last six months or longer. ITP affects multiple age groups and can be seen in children, teenagers, and adults.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other during a treatment period. Unless specified otherwise, the two or more compounds, agents, or active pharmaceutical ingredients may be administered on different schedules during the treatment period, such as, e.g., with one or more compounds, agents, or active pharmaceutical ingredients being administered once a day and one or more other compounds, agents, or active pharmaceutical ingredients being administered twice a day.

As used herein, an amount expressed in terms of "mg of [X]" refers to the total amount in milligrams of [X], i.e., the free base. In some embodiments, PRN1008 may be administered as a pharmaceutically acceptable salt of PRN1008, in which case an amount expressed in terms of "mg of PRN1008" refers to the total amount in milligrams of PRN1008, i.e., the free base, plus the equivalent amount of one or more pharmaceutically acceptable salts of PRN1008 based on the weight of free base therein. For example, "400 mg of at least one compound chosen from PRN1008 and pharmaceutically acceptable salts thereof" includes 400 mg of PRN1008 and a concentration of one or more pharmaceutically acceptable salts of PRN1008 equivalent to 400 mg of PRN1008.

As used herein, a "pharmaceutically acceptable carrier or excipient" means a carrier or an excipient that is useful in preparing a pharmaceutical composition that is generally safe, and neither biologically nor otherwise undesirable, such as, e.g., a carrier or an excipient that is acceptable for mammalian pharmaceutical use.

As used herein, the term "pharmaceutically acceptable salt" refers to a salt form, e.g., an acid addition salt, of an active pharmaceutical agent that is pharmaceutically acceptable and that possesses the desired pharmacological activity of the API of which the salt is made. Pharmaceutically acceptable salts are well known in the art and include those derived from suitable inorganic and organic acids. Such salts include, but are not limited to, salts formed with inorganic acids such as hydrochloric acid, hydrobromic acid, sulfuric acid, phosphoric acid, and the like; or formed with organic acids such as formic acid, acetic acid, propionic acid, hexanoic acid, lactic acid, malonic acid, succinic acid, malic acid, maleic acid, fumaric acid, tartaric acid, citric acid, benzoic acid, mandelic acid, methanesulfonic acid, ethanesulfonic acid, 1,2-ethanedisulfonic acid, benzenesulfonic acid, 4-toluenesulfonic acid, and the like. S. M. Berge et al. describes pharmaceutically acceptable salts in detail in J. Pharmaceutical Sciences, 1977, 66, 1-19.

As used herein, the terms "PRN1008," "rilzabrutinib," "(R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile" and "2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile" are used interchangeably to refer to a compound having the structure:

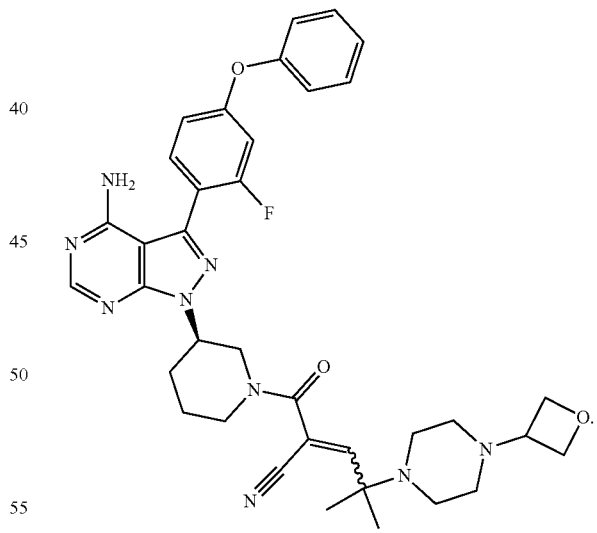

A dose of PRN1008 may contain the corresponding (S) enantiomer as an impurity in less than about 5% by weight, such as, e.g., as an impurity in less than about 1% by weight. Similarly, a dose of the (E) isomer of PRN1008 may contain the corresponding (Z) isomer as an impurity in less than about 1% by weight; a dose of the (Z) isomer of PRN1008 may contain the corresponding (E) isomer as an impurity in less than about 1% by weight. When PRN1008 is denoted as a mixture of (E) and (Z) isomers of (R)-2-[3-[4-amino-3-(2-fluoro-4-phenoxy-phenyl)pyrazolo[3,4-d]pyrimidin-1- yl]piperidine-1-carbonyl]-4-methyl-4-[4-(oxetan-3-yl)piperazin-1-yl]pent-2-enenitrile, it means that the amount of (E) or (Z) isomer in the mixture is greater than about 1% by weight. In some embodiments, the molar ratio of (E) to (Z) isomer is 9:1. PRN1008 or a pharmaceutically acceptable salt thereof may also be referred to herein as a "drug," "active agent," "a therapeutically active agent," or "API."

As used herein, "QD" and "qd" are used interchangeably to refer to once a day.

As used herein, the term "therapeutically effective amount" refers to that an of a compound that produces the desired effect for which it is administered (e.g., improvement in ITP or a symptom of ITP, or lessening the severity of ITP or a symptom of ITP). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the term "treat," "treating," or "treatment," when used in connection with a disorder or condition, includes any effect, e.g., lessening, reducing, modulating, ameliorating, or eliminating, that results in the improvement of the disorder or condition. Improvements in or lessening the severity of any symptom of the disorder or condition can be readily assessed according to standard methods and techniques known in the art.

Some embodiments of the present disclosure relate to methods for treating immune thrombocytopenia (ITP) in a human patient in need thereof comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period.

In some embodiments, the treatment period is 8 days. In some embodiments, the treatment period is 28 days. In some embodiments, the treatment period is 84 days. In some embodiments, the treatment period is 168 days.

In some embodiments, the treatment period is at least 8 days. In some embodiments, the treatment period is at least 28 days. In some embodiments, the treatment period is at least 84 days. In some embodiments, the treatment period is at least 168 days.

In some embodiments, the treatment period is from 8 days to 28 days. In some embodiments, the treatment period is from 8 days to 84 days. In some embodiments, the treatment period is from 8 days to 168 days. In some embodiments, the treatment period is from 28 days to 84 days. In some embodiments, the treatment period is from 28 days to 168 days. In some embodiments, the treatment period is from 84 days to 168 days.

In some embodiments, the methods comprise administering to the human patient 400 mg of at least one compound chosen from PRN1008 and pharmaceutically acceptable salts thereof once a day or twice a day. In some embodiments, the methods comprise administering to the human patient 400 mg of at least one compound chosen from PRN1008 and pharmaceutically acceptable salts thereof once a day. In some embodiments, the methods comprise administering to the human patient 400 mg of at least one compound chosen from PRN1008 and pharmaceutically acceptable salts thereof twice a day.

In some embodiments, the methods comprise administering to the human patient 300 mg of at least one compound chosen from PRN1008 and pharmaceutically acceptable salts thereof twice a day.

In some embodiments, the methods comprise treating primary ITP. In some embodiments, the methods comprise treating secondary ITP. In some embodiments, the methods comprise treating chronic ITP. In some embodiments, the methods comprise treating relapsing ITP. In some embodiments, the methods comprise treating refractory ITP.

In some embodiments, the human patient has at least one characteristic prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient has at least 2 characteristics prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient has at least 3 characteristics prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient has at least 4 characteristics prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient has at least 5 characteristics prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient has all of the following characteristics prior to the start of the treatment period:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient is from 21 to 74 years old prior to the start of the treatment period.

In some embodiments, the human patient has 2 platelet counts of less than 30,000/μL prior to the start of the treatment period. In some embodiments, the human patient has 2 platelet counts of less than 30,000/μL prior to the start of the treatment period, wherein the 2 counts are measured no sooner than 7 days apart. In some embodiments, the human patient has 2 platelet counts of less than 30,000/μL prior to the start of the treatment period, wherein the 2 counts are measured no sooner than 7 days apart in the 15 days prior to the start of the treatment period.

In some embodiments, the human patient has a platelet count of less than 30,000/μL for at least 2 consecutive platelet counts prior to the start of the treatment period. In some embodiments, the human patient has a platelet count of less than 30,000/μL for at least 2 consecutive platelet counts prior to the start of the treatment period, wherein the 2 counts are measured no sooner than 7 days apart. In some embodiments, the human patient has a platelet count of less than 30,000/μL for at least 2 consecutive platelet counts prior to the start of the treatment period, wherein the 2 counts are measured no sooner than 7 days apart in the 15 days prior to the start of the treatment period.

In some embodiments, the average of the human patient's two most recent platelet counts prior to the start of the treatment period is from 3,000/μL to 28,000/μL. In some embodiments, the average of the human patient's two most recent platelet counts prior to the start of the treatment period is from 3,000/μL to 28,000/μL, wherein the two counts are measured no sooner than 7 days apart. In some embodiments, the average of the human patient's two most recent platelet counts prior to the start of the treatment period is from 3,000/μL to 28,000/μL, wherein the two counts are measured no sooner than 7 days apart in the 15 days prior to the start of the treatment period.

In some embodiments, the average of the human patient's two most recent platelet counts prior to the start of the treatment period is from 3,000/μL to 33,000/μL. In some embodiments, the average of the human patient's two most recent platelet counts prior to the start of the treatment period is from 3,000/μL to 33,000/μL, wherein the two counts are measured no sooner than 7 days apart. In some embodiments, the average of the human patient's two most recent platelet counts prior to the start of the treatment period is from 3,000/μL to 33,000/μL, wherein the two counts are measured no sooner than 7 days apart in the 15 days prior to the start of the treatment period.

In some embodiments, the average of the human patient's two most recent platelet counts prior to the start of the treatment period and the human patient's platelet count on the first day of the treatment period is from 3,000/μL to 28,000/μL. In some embodiments, the average of the human patient's two most recent platelet counts prior to the start of the treatment period, wherein the two counts are measured no sooner than 7 days apart, and the human patient's platelet count on the first day of the treatment period is from 3,000/μL to 28,000/μL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/μL to 28,000/μL.

In some embodiments, the average of the human patient's two most recent platelet counts prior to the start of the treatment period and the human patient's platelet count on the first day of the treatment period is from 3,000/μL to 15,000/μL. In some embodiments, the average of the human patient's two most recent platelet counts prior to the start of the treatment period, wherein the two counts are measured no sooner than 7 days apart, and the human patient's platelet count on the first day of the treatment period is from 3,000/μL to 15,000/μL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/μL to 15,000/μL.

In some embodiments, the average of the human patient's two most recent platelet counts prior to the start of the treatment period and the human patient's platelet count on the first day of the treatment period is from 3,000/μL to 33,000/μL. In some embodiments, the average of the human patient's two most recent platelet counts prior to the start of the treatment period, wherein the two counts are measured no sooner than 7 days apart, and the human patient's platelet count on the first day of the treatment period is from 3,000/μL to 33,000/μL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/μL to 33,000/μL.

In some embodiments, the human patient had ITP for at least 2 months prior to the start of the treatment period. In some embodiments, the human patient had ITP for at least 3 months prior to the start of the treatment period. In some embodiments, the human patient had ITP for at least 4 months prior to the start of the treatment period. In some embodiments, the human patient had ITP for at least 5 months prior to the start of the treatment period. In some embodiments, the human patient had ITP for at least 6 months prior to the start of the treatment period.

In some embodiments, the human patient had ITP for at least 1 year prior to the start of the treatment period. In some embodiments, the human patient had ITP for at least 2 years prior to the start of the treatment period. In some embodiments, the human patient had ITP for at least 3 years prior to the start of the treatment period. In some embodiments, the human patient had ITP for at least 4 years prior to the start of the treatment period. In some embodiments, the human patient had ITP for at least 5 years prior to the start of the treatment period. In some embodiments, the human patient had ITP for at least 6 years prior to the start of the treatment period. In some embodiments, the human patient had ITP for at least 7 years prior to the start of the treatment period. In some embodiments, the human patient had ITP for at least 8 years prior to the start of the treatment period. In some embodiments, the human patient had ITP for at least 9 years prior to the start of the treatment period.

In some embodiments, the human patient had ITP for at least 10 years prior to the start of the treatment period. In some embodiments, the human patient had ITP for at least 20 years prior to the start of the treatment period. In some embodiments, the human patient had ITP for at least 30 years prior to the start of the treatment period. In some embodiments, the human patient had ITP for at least 40 years prior to the start of the treatment period. In some embodiments, the human patient had ITP for at least 50 years prior to the start of the treatment period.

In some embodiments, the human patient has a history of taking from 1 to 41 prior ITP therapies prior to the start of the treatment period. In some embodiments, the human patient has a history of taking from 1 to 54 prior ITP therapies prior to the start of the treatment period.

In some embodiments, the human patient has a history of taking at least one prior ITP therapy prior to the start of the treatment period. In some embodiments, the human patient has a history of taking at least 2 prior ITP therapies prior to the start of the treatment period. In some embodiments, the human patient has a history of taking at least 3 prior ITP therapies prior to the start of the treatment period. In some embodiments, the human patient has a history of taking at least 4 prior ITP therapies prior to the start of the treatment period. In some embodiments, the human patient has a history of taking at least 5 prior ITP therapies prior to the start of the treatment period. In some embodiments, the human patient has a history of taking at least 6 prior ITP therapies prior to the start of the treatment period. In some embodiments, the human patient has a history of taking at least 7 prior ITP therapies prior to the start of the treatment period. In some embodiments, the human patient has a history of taking at least 8 prior ITP therapies prior to the start of the treatment period. In some embodiments, the human patient has a history of taking at least 9 prior ITP therapies prior to the start of the treatment period.

In some embodiments, the human patient has a history of taking at least 10 prior ITP therapies prior to the start of the treatment period. In some embodiments, the human patient has a history of taking at least 15 prior ITP therapies prior to the start of the treatment period. In some embodiments, the human patient has a history of taking at least 20 prior ITP therapies prior to the start of the treatment period. In some embodiments, the human patient has a history of taking at least 25 prior ITP therapies prior to the start of the treatment period. In some embodiments, the human patient has a history of taking at least 30 prior ITP therapies prior to the start of the treatment period. In some embodiments, the human patient has a history of taking at least 35 prior ITP therapies prior to the start of the treatment period. In some embodiments, the human patient has a history of taking at least 40 prior ITP therapies prior to the start of the treatment period. In some embodiments, the human patient has a history of taking at least 45 prior ITP therapies prior to the start of the treatment period. In some embodiments, the human patient has a history of taking at least 50 prior ITP therapies prior to the start of the treatment period.

In some embodiments, the at least one prior ITP therapy is chosen from corticosteroids, thrombopoietin receptor agonists, intravenous immunoglobulin, anti-D immunoglobulin, and rituximab.

In some embodiments, the human patient had a splenectomy prior to the start of the treatment period.

In some embodiments, the at least one compound chosen from PRN1008 and pharmaceutically acceptable salts thereof is administered as a monotherapy.

In some embodiments, the at least one compound chosen from PRN1008 and pharmaceutically acceptable salts thereof is administered in combination with at least one concomitant ITP therapy.

In some embodiments, the at least one concomitant ITP therapy is chosen from corticosteroids and thrombopoietin receptor agonists. In some embodiments, the at least one concomitant ITP therapy is chosen from corticosteroids, eltrombopag, and romiplostim.

In some embodiments, the at least one compound chosen from PRN1008 and pharmaceutically acceptable salts thereof comprises at least one compound chosen from the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof comprises at least one compound chosen from the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof comprises a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt of the foregoing.

In some embodiments, the at least one compound chosen from PRN1008 and pharmaceutically acceptable salts thereof consists of at least one compound chosen from the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof consists of at least one compound chosen from the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof consists of a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt of the foregoing.

Some embodiments of the present disclosure relate to methods for increasing a platelet count in a human patient with immune thrombocytopenia (ITP) comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period.

In some embodiments, the methods comprise increasing at least 2 consecutive platelet counts relative to a pre-administration baseline platelet count. In some embodiments, the methods comprise increasing at least 2 consecutive platelet counts relative to a pre-administration baseline platelet count without requiring rescue medication.

In some embodiments, the methods comprise increasing a platelet count by at least 5,000/μL relative to a pre-administration baseline platelet count. In some embodiments, the methods comprise increasing a platelet count by at least 10,000/μL relative to a pre-administration baseline platelet count. In some embodiments, the methods comprise increasing a platelet count by at least 15,000/μL relative to a pre-administration baseline platelet count. In some embodiments, the methods comprise increasing a platelet count by at least 20,000/μL relative to a pre-administration baseline platelet count.

In some embodiments, the methods comprise increasing at least 30% of platelet counts measured during the treatment period by at least 20,000/μL relative to a pre-administration baseline platelet count. In some embodiments, the methods comprise increasing at least 40% of platelet counts measured during the treatment period by at least 20,000/µL relative to a pre-administration baseline platelet count. In some embodiments, the methods comprise increasing at least 50% of platelet counts measured during the treatment period by at least 20,000/µL relative to a pre-administration baseline platelet count. In some embodiments, the methods comprise increasing at least 60% of platelet counts measured during the treatment period by at least 20,000/µL relative to a pre-administration baseline platelet count. In some embodiments, the methods comprise increasing at least 70% of platelet counts measured during the treatment period by at least 20,000/µL relative to a pre-administration baseline platelet count.

In some embodiments, the methods comprise increasing at least 2 of the final 8 platelet counts measured during the treatment period by at least 20,000/µL relative to a pre-administration baseline platelet count. In some embodiments, the methods comprise increasing at least 3 of the final 8 platelet counts measured during the treatment period by at least 20,000/µL relative to a pre-administration baseline platelet count. In some embodiments, the methods comprise increasing at least 4 of the final 8 platelet counts measured during the treatment period by at least 20,000/µL relative to a pre-administration baseline platelet count. In some embodiments, the methods comprise increasing at least 5 of the final 8 platelet counts measured during the treatment period by at least 20,000/µL relative to a pre-administration baseline platelet count. In some embodiments, the methods comprise increasing at least 6 of the final 8 platelet counts measured during the treatment period by at least 20,000/µL relative to a pre-administration baseline platelet count. In some embodiments, the methods comprise increasing at least 7 of the final 8 platelet counts measured during the treatment period by at least 20,000/µL relative to a pre-administration baseline platelet count.

In some embodiments, the methods comprise increasing at least 2 of the final 6 platelet counts measured during the treatment period by at least 20,000/µL relative to a pre-administration baseline platelet count. In some embodiments, the methods comprise increasing at least 3 of the final 6 platelet counts measured during the treatment period by at least 20,000/µL relative to a pre-administration baseline platelet count. In some embodiments, the methods comprise increasing at least 4 of the final 6 platelet counts measured during the treatment period by at least 20,000/µL relative to a pre-administration baseline platelet count. In some embodiments, the methods comprise increasing at least 5 of the final 6 platelet counts measured during the treatment period by at least 20,000/µL relative to a pre-administration baseline platelet count.

In some embodiments, the pre-administration baseline platelet count is an average of the human patient's two most recent platelet counts prior to the start of the treatment period and the human patient's platelet count on the first day of the treatment period. In some embodiments, the pre-administration baseline platelet count is an average of the human patient's two most recent platelet counts prior to the start of the treatment period, wherein the two counts are measured no sooner than 7 days apart, and the human patient's platelet count on the first day of the treatment period. In some embodiments, the pre-administration baseline platelet count is an average of the human patient's two most recent platelet counts prior to the start of the treatment period, wherein the two counts are measured no sooner than 7 days apart in the 15 days prior to the start of the treatment period, and the human patient's platelet count on the first day of the treatment period.

In some embodiments, consecutive platelet counts are measured at least 5 days apart.

In some embodiments, the treatment period is 8 days. In some embodiments, the treatment period is 28 days. In some embodiments, the treatment period is 84 days. In some embodiments, the treatment period is 168 days.

In some embodiments, the treatment period is at least 8 days. In some embodiments, the treatment period is at least 28 days. In some embodiments, the treatment period is at least 84 days. In some embodiments, the treatment period is at least 168 days.

In some embodiments, the treatment period is from 8 days to 28 days. In some embodiments, the treatment period is from 8 days to 84 days. In some embodiments, the treatment period is from 8 days to 168 days. In some embodiments, the treatment period is from 28 days to 84 days. In some embodiments, the treatment period is from 28 days to 168 days. In some embodiments, the treatment period is from 84 days to 168 days.

In some embodiments, the methods comprise administering to the human patient 400 mg of at least one compound chosen from PRN1008 and pharmaceutically acceptable salts thereof once a day or twice a day. In some embodiments, the methods comprise administering to the human patient 400 mg of at least one compound chosen from PRN1008 and pharmaceutically acceptable salts thereof once a day. In some embodiments, the methods comprise administering to the human patient 400 mg of at least one compound chosen from PRN1008 and pharmaceutically acceptable salts thereof twice a day.

In some embodiments, the methods comprise administering to the human patient 300 mg of at least one compound chosen from PRN1008 and pharmaceutically acceptable salts thereof twice a day.

In some embodiments, the human patient has primary ITP. In some embodiments, the human patient has secondary ITP. In some embodiments, the human patient has chronic ITP. In some embodiments, the human patient has relapsing ITP. In some embodiments, the human patient has refractory ITP.

In some embodiments, the human patient has at least one characteristic prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient has at least 2 characteristics prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient has at least 3 characteristics prior to the start of the treatment period chosen from:
an age of from 18 years to 80 years;
no available and approved therapeutic options;
a platelet count of less than 30,000/µL;
an ITP duration of at least one month;

a history of taking at least one prior ITP therapy; and
splenectomy.

In some embodiments, the human patient has at least 4 characteristics prior to the start of the treatment period chosen from:
an age of from 18 years to 80 years;
no available and approved therapeutic options;
a platelet count of less than 30,000/μL;
an ITP duration of at least one month;
a history of taking at least one prior ITP therapy; and
splenectomy.

In some embodiments, the human patient has at least 5 characteristics prior to the start of the treatment period chosen from:
an age of from 18 years to 80 years;
no available and approved therapeutic options;
a platelet count of less than 30,000/μL;
an ITP duration of at least one month;
a history of taking at least one prior ITP therapy; and
splenectomy.

In some embodiments, the human patient has all of the following characteristics prior to the start of the treatment period:
an age of from 18 years to 80 years;
no available and approved therapeutic options;
a platelet count of less than 30,000/μL;
an ITP duration of at least one month;
a history of taking at least one prior ITP therapy; and
splenectomy.

In some embodiments, the human patient is from 21 to 74 years old prior to the start of the treatment period.

In some embodiments, the human patient has 2 platelet counts of less than 30,000/μL prior to the start of the treatment period. In some embodiments, the human patient has 2 platelet counts of less than 30,000/μL prior to the start of the treatment period, wherein the 2 counts are measured no sooner than 7 days apart. In some embodiments, the human patient has 2 platelet counts of less than 30,000/μL prior to the start of the treatment period, wherein the 2 counts are measured no sooner than 7 days apart in the 15 days prior to the start of the treatment period.

In some embodiments, the human patient has a platelet count of less than 30,000/μL for at least 2 consecutive platelet counts prior to the start of the treatment period. In some embodiments, the human patient has a platelet count of less than 30,000/μL for at least 2 consecutive platelet counts prior to the start of the treatment period, wherein the 2 counts are measured no sooner than 7 days apart. In some embodiments, the human patient has a platelet count of less than 30,000/μL for at least 2 consecutive platelet counts prior to the start of the treatment period, wherein the 2 counts are measured no sooner than 7 days apart in the 15 days prior to the start of the treatment period.

In some embodiments, the average of the human patient's two most recent platelet counts prior to the start of the treatment period is from 3,000/μL to 28,000/μL. In some embodiments, the average of the human patient's two most recent platelet counts prior to the start of the treatment period is from 3,000/μL to 28,000/μL, wherein the two counts are measured no sooner than 7 days apart. In some embodiments, the average of the human patient's two most recent platelet counts prior to the start of the treatment period is from 3,000/μL to 28,000/μL, wherein the two counts are measured no sooner than 7 days apart in the 15 days prior to the start of the treatment period.

In some embodiments, the average of the human patient's two most recent platelet counts prior to the start of the treatment period is from 3,000/μL to 33,000/μL. In some embodiments, the average of the human patient's two most recent platelet counts prior to the start of the treatment period is from 3,000/μL to 33,000/μL, wherein the two counts are measured no sooner than 7 days apart. In some embodiments, the average of the human patient's two most recent platelet counts prior to the start of the treatment period is from 3,000/μL to 33,000/μL, wherein the two counts are measured no sooner than 7 days apart in the 15 days prior to the start of the treatment period.

In some embodiments, the average of the human patient's two most recent platelet counts prior to the start of the treatment period and the human patient's platelet count on the first day of the treatment period is from 3,000/μL to 28,000/μL. In some embodiments, the average of the human patient's two most recent platelet counts prior to the start of the treatment period, wherein the two counts are measured no sooner than 7 days apart, and the human patient's platelet count on the first day of the treatment period is from 3,000/μL to 28,000/μL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/μL to 28,000/μL.

In some embodiments, the average of the human patient's two most recent platelet counts prior to the start of the treatment period and the human patient's platelet count on the first day of the treatment period is from 3,000/μL to 15,000/μL. In some embodiments, the average of the human patient's two most recent platelet counts prior to the start of the treatment period, wherein the two counts are measured no sooner than 7 days apart, and the human patient's platelet count on the first day of the treatment period is from 3,000/μL to 15,000/μL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/μL to 15,000/μL.

In some embodiments, the average of the human patient's two most recent platelet counts prior to the start of the treatment period and the human patient's platelet count on the first day of the treatment period is from 3,000/μL to 33,000/μL. In some embodiments, the average of the human patient's two most recent platelet counts prior to the start of the treatment period, wherein the two counts are measured no sooner than 7 days apart, and the human patient's platelet count on the first day of the treatment period is from 3,000/μL to 33,000/μL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/μL to 33,000/μL.

In some embodiments, the human patient had ITP for at least 2 months prior to the start of the treatment period. In some embodiments, the human patient had ITP for at least 3 months prior to the start of the treatment period. In some embodiments, the human patient had ITP for at least 4 months prior to the start of the treatment period. In some embodiments, the human patient had ITP for at least 5 months prior to the start of the treatment period. In some embodiments, the human patient had ITP for at least 6 months prior to the start of the treatment period.

In some embodiments, the human patient had ITP for at least 1 year prior to the start of the treatment period. In some embodiments, the human patient had ITP for at least 2 years prior to the start of the treatment period. In some embodiments, the human patient had ITP for at least 3 years prior to the start of the treatment period. In some embodiments, the human patient had ITP for at least 4 years prior to the start of the treatment period. In some embodiments, the human patient had ITP for at least 5 years prior to the start of the treatment period. In some embodiments, the human patient had ITP for at least 6 years prior to the start of the treatment period. In some embodiments, the human patient had ITP for at least 7 years prior to the start of the treatment period. In some embodiments, the human patient had ITP for at least 8 years prior to the start of the treatment period. In some embodiments, the human patient had ITP for at least 9 years prior to the start of the treatment period.

In some embodiments, the human patient had ITP for at least 10 years prior to the start of the treatment period. In some embodiments, the human patient had ITP for at least 20 years prior to the start of the treatment period. In some embodiments, the human patient had ITP for at least 30 years prior to the start of the treatment period. In some embodiments, the human patient had ITP for at least 40 years prior to the start of the treatment period. In some embodiments, the human patient had ITP for at least 50 years prior to the start of the treatment period.

In some embodiments, the human patient has a history of taking from 1 to 41 prior ITP therapies prior to the start of the treatment period. In some embodiments, the human patient has a history of taking from 1 to 54 prior ITP therapies prior to the start of the treatment period.

In some embodiments, the human patient has a history of taking at least one prior ITP therapy prior to the start of the treatment period. In some embodiments, the human patient has a history of taking at least 2 prior ITP therapies prior to the start of the treatment period. In some embodiments, the human patient has a history of taking at least 3 prior ITP therapies prior to the start of the treatment period. In some embodiments, the human patient has a history of taking at least 4 prior ITP therapies prior to the start of the treatment period. In some embodiments, the human patient has a history of taking at least 5 prior ITP therapies prior to the start of the treatment period. In some embodiments, the human patient has a history of taking at least 6 prior ITP therapies prior to the start of the treatment period. In some embodiments, the human patient has a history of taking at least 7 prior ITP therapies prior to the start of the treatment period. In some embodiments, the human patient has a history of taking at least 8 prior ITP therapies prior to the start of the treatment period. In some embodiments, the human patient has a history of taking at least 9 prior ITP therapies prior to the start of the treatment period.

In some embodiments, the human patient has a history of taking at least 10 prior ITP therapies prior to the start of the treatment period. In some embodiments, the human patient has a history of taking at least 15 prior ITP therapies prior to the start of the treatment period. In some embodiments, the human patient has a history of taking at least 20 prior ITP therapies prior to the start of the treatment period. In some embodiments, the human patient has a history of taking at least 25 prior ITP therapies prior to the start of the treatment period. In some embodiments, the human patient has a history of taking at least 30 prior ITP therapies prior to the start of the treatment period. In some embodiments, the human patient has a history of taking at least 35 prior ITP therapies prior to the start of the treatment period. In some embodiments, the human patient has a history of taking at least 40 prior ITP therapies prior to the start of the treatment period. In some embodiments, the human patient has a history of taking at least 45 prior ITP therapies prior to the start of the treatment period. In some embodiments, the human patient has a history of taking at least 50 prior ITP therapies prior to the start of the treatment period.

In some embodiments, the at least one prior ITP therapy is chosen from corticosteroids, thrombopoietin receptor agonists, intravenous immunoglobulin, anti-D immunoglobulin, and rituximab.

In some embodiments, the human patient had a splenectomy prior to the start of the treatment period.

In some embodiments, the at least one compound chosen from PRN1008 and pharmaceutically acceptable salts thereof is administered as a monotherapy.

In some embodiments, the at least one compound chosen from PRN1008 and pharmaceutically acceptable salts thereof is administered in combination with at least one concomitant ITP therapy.

In some embodiments, the at least one concomitant ITP therapy is chosen from corticosteroids and thrombopoietin receptor agonists. In some embodiments, the at least one concomitant ITP therapy is chosen from corticosteroids, eltrombopag, and romiplostim.

In some embodiments, the at least one compound chosen from PRN1008 and pharmaceutically acceptable salts thereof comprises at least one compound chosen from the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof comprises at least one compound chosen from the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof comprises a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt of the foregoing.

In some embodiments, the at least one compound chosen from PRN1008 and pharmaceutically acceptable salts thereof consists of at least one compound chosen from the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof consists of at least one compound chosen from the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof consists of a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-

[4-(oxetan-3-yl)piperazin-1-yl]pent-2-enenitrile or a pharmaceutically acceptable salt of the foregoing.

Some embodiments of the present disclosure relate to methods for achieving a platelet count of at least 50,000/μL in a human patient with immune thrombocytopenia (ITP) comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period.

In some embodiments, the methods comprise achieving at least 2 platelet counts of at least 50,000/μL. In some embodiments, the methods comprise achieving at least 2 platelet counts of at least 50,000/μL without requiring rescue medication.

In some embodiments, the methods comprise achieving at least 2 consecutive platelet counts of at least 50,000/μL. In some embodiments, the methods comprise achieving at least 2 consecutive platelet counts of at least 50,000/μL without requiring rescue medication.

In some embodiments, the methods comprise achieving a platelet count of at least 50,000/μL in at least 30% of platelet counts measured during the treatment period. In some embodiments, the methods comprise achieving a platelet count of at least 50,000/μL in at least 35% of platelet counts measured during the treatment period. In some embodiments, the methods comprise achieving a platelet count of at least 50,000/μL in at least 40% of platelet counts measured during the treatment period. In some embodiments, the methods comprise achieving a platelet count of at least 50,000/μL in at least 45% of platelet counts measured during the treatment period. In some embodiments, the methods comprise achieving a platelet count of at least 50,000/μL in at least 50% of platelet counts measured during the treatment period. In some embodiments, the methods comprise achieving a platelet count of at least 50,000/μL in at least 55% of platelet counts measured during the treatment period. In some embodiments, the methods comprise achieving a platelet count of at least 50,000/μL in at least 60% of platelet counts measured during the treatment period. In some embodiments, the methods comprise achieving a platelet count of at least 50,000/μL in at least 65% of platelet counts measured during the treatment period. In some embodiments, the methods comprise achieving a platelet count of at least 50,000/μL in at least 70% of platelet counts measured during the treatment period.

In some embodiments, the methods comprise achieving a platelet count of at least 50,000/μL in at least 2 of the final 8 platelet counts measured during the treatment period. In some embodiments, the methods comprise achieving a platelet count of at least 50,000/μL in at least 3 of the final 8 platelet counts measured during the treatment period. In some embodiments, the methods comprise achieving a platelet count of at least 50,000/μL in at least 4 of the final 8 platelet counts measured during the treatment period. In some embodiments, the methods comprise achieving a platelet count of at least 50,000/μL in at least 5 of the final 8 platelet counts measured during the treatment period. In some embodiments, the methods comprise achieving a platelet count of at least 50,000/μL in at least 6 of the final 8 platelet counts measured during the treatment period. In some embodiments, the methods comprise achieving a platelet count of at least 50,000/μL in at least 7 of the final 8 platelet counts measured during the treatment period.

In some embodiments, the methods comprise achieving a platelet count of at least 50,000/μL in at least 2 of the final 6 platelet counts measured during the treatment period. In some embodiments, the methods comprise achieving a platelet count of at least 50,000/μL in at least 3 of the final 6 platelet counts measured during the treatment period. In some embodiments, the methods comprise achieving a platelet count of at least 50,000/μL in at least 4 of the final 6 platelet counts measured during the treatment period. In some embodiments, the methods comprise achieving a platelet count of at least 50,000/μL in at least 5 of the final 6 platelet counts measured during the treatment period.

In some embodiments, the methods comprise increasing at least 30% of platelet counts measured during the treatment period by at least 20,000/μL relative to a pre-administration baseline platelet count. In some embodiments, the methods comprise increasing at least 40% of platelet counts measured during the treatment period by at least 20,000/μL relative to a pre-administration baseline platelet count. In some embodiments, the methods comprise increasing at least 50% of platelet counts measured during the treatment period by at least 20,000/μL relative to a pre-administration baseline platelet count. In some embodiments, the methods comprise increasing at least 60% of platelet counts measured during the treatment period by at least 20,000/μL relative to a pre-administration baseline platelet count. In some embodiments, the methods comprise increasing at least 70% of platelet counts measured during the treatment period by at least 20,000/μL relative to a pre-administration baseline platelet count.

In some embodiments, the methods comprise increasing at least 2 of the final 8 platelet counts measured during the treatment period by at least 20,000/μL relative to a pre-administration baseline platelet count. In some embodiments, the methods comprise increasing at least 3 of the final 8 platelet counts measured during the treatment period by at least 20,000/μL relative to a pre-administration baseline platelet count. In some embodiments, the methods comprise increasing at least 4 of the final 8 platelet counts measured during the treatment period by at least 20,000/μL relative to a pre-administration baseline platelet count. In some embodiments, the methods comprise increasing at least 5 of the final 8 platelet counts measured during the treatment period by at least 20,000/μL relative to a pre-administration baseline platelet count. In some embodiments, the methods comprise increasing at least 6 of the final 8 platelet counts measured during the treatment period by at least 20,000/μL relative to a pre-administration baseline platelet count. In some embodiments, the methods comprise increasing at least 7 of the final 8 platelet counts measured during the treatment period by at least 20,000/μL relative to a pre-administration baseline platelet count.

In some embodiments, the methods comprise increasing at least 2 of the final 6 platelet counts measured during the treatment period by at least 20,000/μL relative to a pre-administration baseline platelet count. In some embodiments, the methods comprise increasing at least 3 of the final 6 platelet counts measured during the treatment period by at least 20,000/μL relative to a pre-administration baseline platelet count. In some embodiments, the methods comprise increasing at least 4 of the final 6 platelet counts measured during the treatment period by at least 20,000/μL relative to a pre-administration baseline platelet count. In some embodiments, the methods comprise increasing at least 5 of the final 6 platelet counts measured during the treatment period by at least 20,000/μL relative to a pre-administration baseline platelet count.

In some embodiments, the pre-administration baseline platelet count is an average of the human patient's two most recent platelet counts prior to the start of the treatment period and the human patient's platelet count on the first day of the treatment period. In some embodiments, the pre-administration baseline platelet count is an average of the human patient's two most recent platelet counts prior to the start of the treatment period, wherein the two counts are measured no sooner than 7 days apart, and the human patient's platelet count on the first day of the treatment period. In some embodiments, the pre-administration baseline platelet count is an average of the human patient's two most recent platelet counts prior to the start of the treatment period, wherein the two counts are measured no sooner than 7 days apart in the 15 days prior to the start of the treatment period, and the human patient's platelet count on the first day of the treatment period.

In some embodiments, consecutive platelet counts are measured at least 5 days apart.

In some embodiments, the treatment period is 8 days. In some embodiments, the treatment period is 28 days. In some embodiments, the treatment period is 84 days. In some embodiments, the treatment period is 168 days.

In some embodiments, the treatment period is at least 8 days. In some embodiments, the treatment period is at least 28 days. In some embodiments, the treatment period is at least 84 days. In some embodiments, the treatment period is at least 168 days.

In some embodiments, the treatment period is from 8 days to 28 days. In some embodiments, the treatment period is from 8 days to 84 days. In some embodiments, the treatment period is from 8 days to 168 days. In some embodiments, the treatment period is from 28 days to 84 days. In some embodiments, the treatment period is from 28 days to 168 days. In some embodiments, the treatment period is from 84 days to 168 days.

In some embodiments, the methods comprise administering to the human patient 400 mg of at least one compound chosen from PRN1008 and pharmaceutically acceptable salts thereof once a day or twice a day. In some embodiments, the methods comprise administering to the human patient 400 mg of at least one compound chosen from PRN1008 and pharmaceutically acceptable salts thereof once a day. In some embodiments, the methods comprise administering to the human patient 400 mg of at least one compound chosen from PRN1008 and pharmaceutically acceptable salts thereof twice a day.

In some embodiments, the methods comprise administering to the human patient 300 mg of at least one compound chosen from PRN1008 and pharmaceutically acceptable salts thereof twice a day.

In some embodiments, the human patient has primary ITP. In some embodiments, the human patient has secondary ITP. In some embodiments, the human patient has chronic ITP. In some embodiments, the human patient has relapsing ITP. In some embodiments, the human patient has refractory ITP.

In some embodiments, the human patient has at least one characteristic prior to the start of the treatment period chosen from:
    an age of from 18 years to 80 years;
    no available and approved therapeutic options;
    a platelet count of less than 30,000/μL;
    an ITP duration of at least one month;
    a history of taking at least one prior ITP therapy; and
    splenectomy.

In some embodiments, the human patient has at least 2 characteristics prior to the start of the treatment period chosen from:
    an age of from 18 years to 80 years;
    no available and approved therapeutic options;
    a platelet count of less than 30,000/μL;
    an ITP duration of at least one month;
    a history of taking at least one prior ITP therapy; and
    splenectomy.

In some embodiments, the human patient has at least 3 characteristics prior to the start of the treatment period chosen from:
    an age of from 18 years to 80 years;
    no available and approved therapeutic options;
    a platelet count of less than 30,000/μL;
    an ITP duration of at least one month;
    a history of taking at least one prior ITP therapy; and
    splenectomy.

In some embodiments, the human patient has at least 4 characteristics prior to the start of the treatment period chosen from:
    an age of from 18 years to 80 years;
    no available and approved therapeutic options;
    a platelet count of less than 30,000/μL;
    an ITP duration of at least one month;
    a history of taking at least one prior ITP therapy; and
    splenectomy.

In some embodiments, the human patient has at least 5 characteristics prior to the start of the treatment period chosen from:
    an age of from 18 years to 80 years;
    no available and approved therapeutic options;
    a platelet count of less than 30,000/μL;
    an ITP duration of at least one month;
    a history of taking at least one prior ITP therapy; and
    splenectomy.

In some embodiments, the human patient has all of the following characteristics prior to the start of the treatment period:
    an age of from 18 years to 80 years;
    no available and approved therapeutic options;
    a platelet count of less than 30,000/μL;
    an ITP duration of at least one month;
    a history of taking at least one prior ITP therapy; and
    splenectomy.

In some embodiments, the human patient is from 21 to 74 years old prior to the start of the treatment period.

In some embodiments, the human patient has 2 platelet counts of less than 30,000/μL prior to the start of the treatment period. In some embodiments, the human patient has 2 platelet counts of less than 30,000/μL prior to the start of the treatment period, wherein the 2 counts are measured no sooner than 7 days apart. In some embodiments, the human patient has 2 platelet counts of less than 30,000/μL prior to the start of the treatment period, wherein the 2 counts are measured no sooner than 7 days apart in the 15 days prior to the start of the treatment period.

In some embodiments, the human patient has a platelet count of less than 30,000/μL for at least 2 consecutive platelet counts prior to the start of the treatment period. In some embodiments, the human patient has a platelet count of less than 30,000/μL for at least 2 consecutive platelet counts prior to the start of the treatment period, wherein the 2 counts are measured no sooner than 7 days apart. In some embodiments, the human patient has a platelet count of less than 30,000/μL for at least 2 consecutive platelet counts prior to the start of the treatment period, wherein the 2 counts are measured no sooner than 7 days apart in the 15 days prior to the start of the treatment period.

In some embodiments, the average of the human patient's two most recent platelet counts prior to the start of the treatment period is from 3,000/μL to 28,000/μL. In some embodiments, the average of the human patient's two most recent platelet counts prior to the start of the treatment period is from 3,000/μL to 28,000/μL, wherein the two counts are measured no sooner than 7 days apart. In some embodiments, the average of the human patient's two most recent platelet counts prior to the start of the treatment period is from 3,000/μL to 28,000/μL, wherein the two counts are measured no sooner than 7 days apart in the 15 days prior to the start of the treatment period.

In some embodiments, the average of the human patient's two most recent platelet counts prior to the start of the treatment period is from 3,000/μL to 33,000/μL. In some embodiments, the average of the human patient's two most recent platelet counts prior to the start of the treatment period is from 3,000/μL to 33,000/μL, wherein the two counts are measured no sooner than 7 days apart. In some embodiments, the average of the human patient's two most recent platelet counts prior to the start of the treatment period is from 3,000/μL to 33,000/μL, wherein the two counts are measured no sooner than 7 days apart in the 15 days prior to the start of the treatment period.

In some embodiments, the average of the human patient's two most recent platelet counts prior to the start of the treatment period and the human patient's platelet count on the first day of the treatment period is from 3,000/μL to 28,000/μL. In some embodiments, the average of the human patient's two most recent platelet counts prior to the start of the treatment period, wherein the two counts are measured no sooner than 7 days apart, and the human patient's platelet count on the first day of the treatment period is from 3,000/μL to 28,000/μL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/μL to 28,000/μL.

In some embodiments, the average of the human patient's two most recent platelet counts prior to the start of the treatment period and the human patient's platelet count on the first day of the treatment period is from 3,000/μL to 15,000/μL. In some embodiments, the average of the human patient's two most recent platelet counts prior to the start of the treatment period, wherein the two counts are measured no sooner than 7 days apart, and the human patient's platelet count on the first day of the treatment period is from 3,000/μL to 15,000/μL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/μL to 15,000/μL.

In some embodiments, the average of the human patient's two most recent platelet counts prior to the start of the treatment period and the human patient's platelet count on the first day of the treatment period is from 3,000/μL to 33,000/μL. In some embodiments, the average of the human patient's two most recent platelet counts prior to the start of the treatment period, wherein the two counts are measured no sooner than 7 days apart, and the human patient's platelet count on the first day of the treatment period is from 3,000/μL to 33,000/μL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/μL to 33,000/μL.

In some embodiments, the human patient had ITP for at least 2 months prior to the start of the treatment period. In some embodiments, the human patient had ITP for at least 3 months prior to the start of the treatment period. In some embodiments, the human patient had ITP for at least 4 months prior to the start of the treatment period. In some embodiments, the human patient had ITP for at least 5 months prior to the start of the treatment period. In some embodiments, the human patient had ITP for at least 6 months prior to the start of the treatment period.

In some embodiments, the human patient had ITP for at least 1 year prior to the start of the treatment period. In some embodiments, the human patient had ITP for at least 2 years prior to the start of the treatment period. In some embodiments, the human patient had ITP for at least 3 years prior to the start of the treatment period. In some embodiments, the human patient had ITP for at least 4 years prior to the start of the treatment period. In some embodiments, the human patient had ITP for at least 5 years prior to the start of the treatment period. In some embodiments, the human patient had ITP for at least 6 years prior to the start of the treatment period. In some embodiments, the human patient had ITP for at least 7 years prior to the start of the treatment period. In some embodiments, the human patient had ITP for at least 8 years prior to the start of the treatment period. In some embodiments, the human patient had ITP for at least 9 years prior to the start of the treatment period.

In some embodiments, the human patient had ITP for at least 10 years prior to the start of the treatment period. In some embodiments, the human patient had ITP for at least 20 years prior to the start of the treatment period. In some embodiments, the human patient had ITP for at least 30 years prior to the start of the treatment period. In some embodiments, the human patient had ITP for at least 40 years prior to the start of the treatment period. In some embodiments, the human patient had ITP for at least 50 years prior to the start of the treatment period.

In some embodiments, the human patient has a history of taking from 1 to 41 prior ITP therapies prior to the start of the treatment period. In some embodiments, the human patient has a history of taking from 1 to 54 prior ITP therapies prior to the start of the treatment period.

In some embodiments, the human patient has a history of taking at least one prior ITP therapy prior to the start of the treatment period. In some embodiments, the human patient has a history of taking at least 2 prior ITP therapies prior to the start of the treatment period. In some embodiments, the human patient has a history of taking at least 3 prior ITP therapies prior to the start of the treatment period. In some embodiments, the human patient has a history of taking at least 4 prior ITP therapies prior to the start of the treatment period. In some embodiments, the human patient has a history of taking at least 5 prior ITP therapies prior to the start of the treatment period. In some embodiments, the human patient has a history of taking at least 6 prior ITP therapies prior to the start of the treatment period. In some embodiments, the human patient has a history of taking at least 7 prior ITP therapies prior to the start of the treatment period. In some embodiments, the human patient has a history of taking at least 8 prior ITP therapies prior to the start of the treatment period. In some embodiments, the human patient has a history of taking at least 9 prior ITP therapies prior to the start of the treatment period.

In some embodiments, the human patient has a history of taking at least 10 prior ITP therapies prior to the start of the treatment period. In some embodiments, the human patient has a history of taking at least 15 prior ITP therapies prior to the start of the treatment period. In some embodiments, the human patient has a history of taking at least 20 prior ITP therapies prior to the start of the treatment period. In some embodiments, the human patient has a history of taking at least 25 prior ITP therapies prior to the start of the treatment period. In some embodiments, the human patient has a history of taking at least 30 prior ITP therapies prior to the start of the treatment period. In some embodiments, the human patient has a history of taking at least 35 prior ITP therapies prior to the start of the treatment period. In some embodiments, the human patient has a history of taking at least 40 prior ITP therapies prior to the start of the treatment period. In some embodiments, the human patient has a history of taking at least 45 prior ITP therapies prior to the start of the treatment period. In some embodiments, the human patient has a history of taking at least 50 prior ITP therapies prior to the start of the treatment period.

In some embodiments, the at least one prior ITP therapy is chosen from corticosteroids, thrombopoietin receptor agonists, intravenous immunoglobulin, anti-D immunoglobulin, and rituximab.

In some embodiments, the human patient had a splenectomy prior to the start of the treatment period.

In some embodiments, the at least one compound chosen from PRN1008 and pharmaceutically acceptable salts thereof is administered as a monotherapy.

In some embodiments, the at least one compound chosen from PRN1008 and pharmaceutically acceptable salts thereof is administered in combination with at least one concomitant ITP therapy.

In some embodiments, the at least one concomitant ITP therapy is chosen from corticosteroids and thrombopoietin receptor agonists. In some embodiments, the at least one concomitant ITP therapy is chosen from corticosteroids, eltrombopag, and romiplostim.

In some embodiments, the at least one compound chosen from PRN1008 and pharmaceutically acceptable salts thereof comprises at least one compound chosen from the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof comprises at least one compound chosen from the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof comprises a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt of the foregoing.

In some embodiments, the at least one compound chosen from PRN1008 and pharmaceutically acceptable salts thereof consists of at least one compound chosen from the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof consists of at least one compound chosen from the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof consists of a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt of the foregoing.

Some embodiments of the present disclosure relate to methods for achieving at least one platelet count of at least 50,000/µL and increasing at least one platelet count by at least 20,000/µL in a human patient with immune thrombocytopenia (ITP) comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period.

In some embodiments, the methods comprise achieving at least 2 platelet counts of at least 50,000/µL. In some embodiments, the methods comprise achieving at least 2 platelet counts of at least 50,000/µL without requiring rescue medication.

In some embodiments, the methods comprise achieving at least 2 consecutive platelet counts of at least 50,000/µL. In some embodiments, the methods comprise achieving at least 2 consecutive platelet counts of at least 50,000/µL without requiring rescue medication.

In some embodiments, the methods comprise achieving a platelet count of at least 50,000/µL in at least 30% of platelet counts measured during the treatment period. In some embodiments, the methods comprise achieving a platelet count of at least 50,000/µL in at least 35% of platelet counts measured during the treatment period. In some embodiments, the methods comprise achieving a platelet count of at least 50,000/µL in at least 40% of platelet counts measured during the treatment period. In some embodiments, the methods comprise achieving a platelet count of at least 50,000/µL in at least 45% of platelet counts measured during the treatment period. In some embodiments, the methods comprise achieving a platelet count of at least 50,000/µL in at least 50% of platelet counts measured during the treatment period. In some embodiments, the methods comprise achieving a platelet count of at least 50,000/µL in at least 55% of platelet counts measured during the treatment period. In some embodiments, the methods comprise achieving a platelet count of at least 50,000/µL in at least 60% of platelet counts measured during the treatment period. In some embodiments, the methods comprise achieving a platelet count of at least 50,000/µL in at least 65% of platelet counts measured during the treatment period. In some embodiments, the methods comprise achieving a platelet count of at least 50,000/µL in at least 70% of platelet counts measured during the treatment period.

In some embodiments, the methods comprise achieving a platelet count of at least 50,000/µL in at least 2 of the final 8 platelet counts measured during the treatment period. In some embodiments, the methods comprise achieving a platelet count of at least 50,000/µL in at least 3 of the final 8 platelet counts measured during the treatment period. In some embodiments, the methods comprise achieving a platelet count of at least 50,000/µL in at least 4 of the final 8 platelet counts measured during the treatment period. In some embodiments, the methods comprise achieving a platelet count of at least 50,000/µL in at least 5 of the final 8 platelet counts measured during the treatment period. In some embodiments, the methods comprise achieving a platelet count of at least 50,000/µL in at least 6 of the final 8 platelet counts measured during the treatment period. In some embodiments, the methods comprise achieving a platelet count of at least 50,000/µL in at least 7 of the final 8 platelet counts measured during the treatment period.

In some embodiments, the methods comprise achieving a platelet count of at least 50,000/µL in at least 2 of the final 6 platelet counts measured during the treatment period. In some embodiments, the methods comprise achieving a platelet count of at least 50,000/µL in at least 3 of the final 6 platelet counts measured during the treatment period. In some embodiments, the methods comprise achieving a platelet count of at least 50,000/µL in at least 4 of the final 6 platelet counts measured during the treatment period. In some embodiments, the methods comprise achieving a platelet count of at least 50,000/µL in at least 5 of the final 6 platelet counts measured during the treatment period.

In some embodiments, consecutive platelet counts are measured at least 5 days apart.

In some embodiments, the treatment period is 8 days. In some embodiments, the treatment period is 28 days. In some embodiments, the treatment period is 84 days. In some embodiments, the treatment period is 168 days.

In some embodiments, the treatment period is at least 8 days. In some embodiments, the treatment period is at least 28 days. In some embodiments, the treatment period is at least 84 days. In some embodiments, the treatment period is at least 168 days.

In some embodiments, the treatment period is from 8 days to 28 days. In some embodiments, the treatment period is from 8 days to 84 days. In some embodiments, the treatment period is from 8 days to 168 days. In some embodiments, the treatment period is from 28 days to 84 days. In some embodiments, the treatment period is from 28 days to 168 days. In some embodiments, the treatment period is from 84 days to 168 days.

In some embodiments, the methods comprise administering to the human patient 400 mg of at least one compound chosen from PRN1008 and pharmaceutically acceptable salts thereof once a day or twice a day. In some embodiments, the methods comprise administering to the human patient 400 mg of at least one compound chosen from PRN1008 and pharmaceutically acceptable salts thereof once a day. In some embodiments, the methods comprise administering to the human patient 400 mg of at least one compound chosen from PRN1008 and pharmaceutically acceptable salts thereof twice a day.

In some embodiments, the methods comprise administering to the human patient 300 mg of at least one compound chosen from PRN1008 and pharmaceutically acceptable salts thereof twice a day.

In some embodiments, the human patient has primary ITP. In some embodiments, the human patient has secondary ITP. In some embodiments, the human patient has chronic ITP. In some embodiments, the human patient has relapsing ITP. In some embodiments, the human patient has refractory ITP.

In some embodiments, the human patient has at least one characteristic prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient has at least 2 characteristics prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient has at least 3 characteristics prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient has at least 4 characteristics prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient has at least 5 characteristics prior to the start of the treatment period chosen from:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient has all of the following characteristics prior to the start of the treatment period:
an age of from 18 years to 80 years;
no available and approved therapeutic options;
a platelet count of less than 30,000/µL;
an ITP duration of at least one month;
a history of taking at least one prior ITP therapy; and
splenectomy.

In some embodiments, the human patient is from 21 to 74 years old prior to the start of the treatment period.

In some embodiments, the human patient has 2 platelet counts of less than 30,000/µL prior to the start of the treatment period. In some embodiments, the human patient has 2 platelet counts of less than 30,000/µL prior to the start of the treatment period, wherein the 2 counts are measured no sooner than 7 days apart. In some embodiments, the human patient has 2 platelet counts of less than 30,000/µL prior to the start of the treatment period, wherein the 2 counts are measured no sooner than 7 days apart in the 15 days prior to the start of the treatment period.

In some embodiments, the human patient has a platelet count of less than 30,000/µL for at least 2 consecutive platelet counts prior to the start of the treatment period. In some embodiments, the human patient has a platelet count of less than 30,000/µL for at least 2 consecutive platelet counts prior to the start of the treatment period, wherein the 2 counts are measured no sooner than 7 days apart. In some embodiments, the human patient has a platelet count of less than 30,000/µL for at least 2 consecutive platelet counts prior to the start of the treatment period, wherein the 2 counts are measured no sooner than 7 days apart in the 15 days prior to the start of the treatment period.

In some embodiments, the average of the human patient's two most recent platelet counts prior to the start of the treatment period is from 3,000/µL to 28,000/µL. In some embodiments, the average of the human patient's two most recent platelet counts prior to the start of the treatment period is from 3,000/µL to 28,000/µL, wherein the two counts are measured no sooner than 7 days apart. In some embodiments, the average of the human patient's two most recent platelet counts prior to the start of the treatment period is from 3,000/µL to 28,000/µL, wherein the two counts are measured no sooner than 7 days apart in the 15 days prior to the start of the treatment period.

In some embodiments, the average of the human patient's two most recent platelet counts prior to the start of the treatment period is from 3,000/µL to 33,000/µL. In some embodiments, the average of the human patient's two most recent platelet counts prior to the start of the treatment period is from 3,000/µL to 33,000/µL, wherein the two counts are measured no sooner than 7 days apart. In some embodiments, the average of the human patient's two most recent platelet counts prior to the start of the treatment period is from 3,000/µL to 33,000/µL, wherein the two counts are measured no sooner than 7 days apart in the 15 days prior to the start of the treatment period.

In some embodiments, the average of the human patient's two most recent platelet counts prior to the start of the treatment period and the human patient's platelet count on the first day of the treatment period is from 3,000/µL to 28,000/µL. In some embodiments, the average of the human patient's two most recent platelet counts prior to the start of the treatment period, wherein the two counts are measured no sooner than 7 days apart, and the human patient's platelet count on the first day of the treatment period is from 3,000/µL to 28,000/µL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/µL to 28,000/µL.

In some embodiments, the average of the human patient's two most recent platelet counts prior to the start of the treatment period and the human patient's platelet count on the first day of the treatment period is from 3,000/µL to 15,000/µL. In some embodiments, the average of the human patient's two most recent platelet counts prior to the start of the treatment period, wherein the two counts are measured no sooner than 7 days apart, and the human patient's platelet count on the first day of the treatment period is from 3,000/µL to 15,000/µL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/µL to 15,000/µL.

In some embodiments, the average of the human patient's two most recent platelet counts prior to the start of the treatment period and the human patient's platelet count on the first day of the treatment period is from 3,000/µL to 33,000/µL. In some embodiments, the average of the human patient's two most recent platelet counts prior to the start of the treatment period, wherein the two counts are measured no sooner than 7 days apart, and the human patient's platelet count on the first day of the treatment period is from 3,000/µL to 33,000/µL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/µL to 33,000/µL.

In some embodiments, the human patient had ITP for at least 2 months prior to the start of the treatment period. In some embodiments, the human patient had ITP for at least 3 months prior to the start of the treatment period. In some embodiments, the human patient had ITP for at least 4 months prior to the start of the treatment period. In some embodiments, the human patient had ITP for at least 5 months prior to the start of the treatment period. In some embodiments, the human patient had ITP for at least 6 months prior to the start of the treatment period.

In some embodiments, the human patient had ITP for at least 1 year prior to the start of the treatment period. In some embodiments, the human patient had ITP for at least 2 years prior to the start of the treatment period. In some embodiments, the human patient had ITP for at least 3 years prior to the start of the treatment period. In some embodiments, the human patient had ITP for at least 4 years prior to the start of the treatment period. In some embodiments, the human patient had ITP for at least 5 years prior to the start of the treatment period. In some embodiments, the human patient had ITP for at least 6 years prior to the start of the treatment period. In some embodiments, the human patient had ITP for at least 7 years prior to the start of the treatment period. In some embodiments, the human patient had ITP for at least 8 years prior to the start of the treatment period. In some embodiments, the human patient had ITP for at least 9 years prior to the start of the treatment period.

In some embodiments, the human patient had ITP for at least 10 years prior to the start of the treatment period. In some embodiments, the human patient had ITP for at least 20 years prior to the start of the treatment period. In some embodiments, the human patient had ITP for at least 30 years prior to the start of the treatment period. In some embodiments, the human patient had ITP for at least 40 years prior to the start of the treatment period. In some embodiments, the human patient had ITP for at least 50 years prior to the start of the treatment period.

In some embodiments, the human patient has a history of taking from 1 to 41 prior ITP therapies prior to the start of the treatment period. In some embodiments, the human patient has a history of taking from 1 to 54 prior ITP therapies prior to the start of the treatment period.

In some embodiments, the human patient has a history of taking at least one prior ITP therapy prior to the start of the treatment period. In some embodiments, the human patient has a history of taking at least 2 prior ITP therapies prior to the start of the treatment period. In some embodiments, the human patient has a history of taking at least 3 prior ITP therapies prior to the start of the treatment period. In some embodiments, the human patient has a history of taking at least 4 prior ITP therapies prior to the start of the treatment period. In some embodiments, the human patient has a history of taking at least 5 prior ITP therapies prior to the start of the treatment period. In some embodiments, the human patient has a history of taking at least 6 prior ITP therapies prior to the start of the treatment period. In some embodiments, the human patient has a history of taking at least 7 prior ITP therapies prior to the start of the treatment period. In some embodiments, the human patient has a history of taking at least 8 prior ITP therapies prior to the start of the treatment period. In some embodiments, the human patient has a history of taking at least 9 prior ITP therapies prior to the start of the treatment period.

In some embodiments, the human patient has a history of taking at least 10 prior ITP therapies prior to the start of the treatment period. In some embodiments, the human patient has a history of taking at least 15 prior ITP therapies prior to the start of the treatment period. In some embodiments, the human patient has a history of taking at least 20 prior ITP therapies prior to the start of the treatment period. In some embodiments, the human patient has a history of taking at least 25 prior ITP therapies prior to the start of the treatment period. In some embodiments, the human patient has a history of taking at least 30 prior ITP therapies prior to the start of the treatment period. In some embodiments, the human patient has a history of taking at least 35 prior ITP therapies prior to the start of the treatment period. In some embodiments, the human patient has a history of taking at least 40 prior ITP therapies prior to the start of the treatment period. In some embodiments, the human patient has a history of taking at least 45 prior ITP therapies prior to the start of the treatment period. In some embodiments, the human patient has a history of taking at least 50 prior ITP therapies prior to the start of the treatment period.

In some embodiments, the at least one prior ITP therapy is chosen from corticosteroids, thrombopoietin receptor agonists, intravenous immunoglobulin, anti-D immunoglobulin, and rituximab.

In some embodiments, the human patient had a splenectomy prior to the start of the treatment period.

In some embodiments, the at least one compound chosen from PRN1008 and pharmaceutically acceptable salts thereof is administered as a monotherapy.

In some embodiments, the at least one compound chosen from PRN1008 and pharmaceutically acceptable salts thereof is administered in combination with at least one concomitant ITP therapy.

In some embodiments, the at least one concomitant ITP therapy is chosen from corticosteroids and thrombopoietin receptor agonists. In some embodiments, the at least one concomitant ITP therapy is chosen from corticosteroids, eltrombopag, and romiplostim.

In some embodiments, the at least one compound chosen from PRN1008 and pharmaceutically acceptable salts thereof comprises at least one compound chosen from the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof comprises at least one compound chosen from the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof comprises a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt of the foregoing.

In some embodiments, the at least one compound chosen from PRN1008 and pharmaceutically acceptable salts thereof consists of at least one compound chosen from the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof consists of at least one compound chosen from the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof consists of a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt of the foregoing.

Some embodiments of the present disclosure relate to methods for achieving a platelet count of at least 30,000/μL in a human patient with immune thrombocytopenia (ITP) comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008) and pharmaceutically acceptable salts thereof once a day or twice a day for a treatment period.

In some embodiments, the methods comprise achieving a platelet count of at least 30,000/μL in at least 30% of platelet counts measured during the treatment period. In some embodiments, the methods comprise achieving a platelet count of at least 30,000/μL in at least 35% of platelet counts measured during the treatment period. In some embodiments, the methods comprise achieving a platelet count of at least 30,000/μL in at least 40% of platelet counts measured during the treatment period. In some embodiments, the methods comprise achieving a platelet count of at least 30,000/μL in at least 45% of platelet counts measured during the treatment period. In some embodiments, the methods comprise achieving a platelet count of at least 30,000/μL in at least 50% of platelet counts measured during the treatment period. In some embodiments, the methods comprise achieving a platelet count of at least 30,000/μL in at least 55% of platelet counts measured during the treatment period. In some embodiments, the methods comprise achieving a platelet count of at least 30,000/μL in at least 60% of platelet counts measured during the treatment period. In some embodiments, the methods comprise achieving a platelet count of at least 30,000/μL in at least 65% of platelet counts measured during the treatment period. In some embodiments, the methods comprise achieving a platelet count of at least 30,000/μL in at least 70% of platelet counts measured during the treatment period.

In some embodiments, the methods comprise achieving a platelet count of at least 30,000/μL in at least 2 of the final 8 platelet counts measured during the treatment period. In some embodiments, the methods comprise achieving a platelet count of at least 30,000/μL in at least 3 of the final 8 platelet counts measured during the treatment period. In some embodiments, the methods comprise achieving a platelet count of at least 30,000/μL in at least 4 of the final 8 platelet counts measured during the treatment period. In some embodiments, the methods comprise achieving a platelet count of at least 30,000/μL in at least 5 of the final 8 platelet counts measured during the treatment period. In some embodiments, the methods comprise achieving a platelet count of at least 30,000/μL in at least 6 of the final 8 platelet counts measured during the treatment period. In some embodiments, the methods comprise achieving a platelet count of at least 30,000/μL in at least 7 of the final 8 platelet counts measured during the treatment period.

In some embodiments, the methods comprise achieving a platelet count of at least 30,000/μL in at least 2 of the final 6 platelet counts measured during the treatment period. In some embodiments, the methods comprise achieving a platelet count of at least 30,000/μL in at least 3 of the final 6 platelet counts measured during the treatment period. In some embodiments, the methods comprise achieving a platelet count of at least 30,000/μL in at least 4 of the final 6 platelet counts measured during the treatment period. In some embodiments, the methods comprise achieving a platelet count of at least 30,000/μL in at least 5 of the final 6 platelet counts measured during the treatment period.

In some embodiments, the treatment period is 8 days. In some embodiments, the treatment period is 28 days. In some embodiments, the treatment period is 84 days. In some embodiments, the treatment period is 168 days.

In some embodiments, the treatment period is at least 8 days. In some embodiments, the treatment period is at least 28 days. In some embodiments, the treatment period is at least 84 days. In some embodiments, the treatment period is at least 168 days.

In some embodiments, the treatment period is from 8 days to 28 days. In some embodiments, the treatment period is from 8 days to 84 days. In some embodiments, the treatment period is from 8 days to 168 days. In some embodiments, the treatment period is from 28 days to 84 days. In some embodiments, the treatment period is from 28 days to 168 days. In some embodiments, the treatment period is from 84 days to 168 days.

In some embodiments, the methods comprise administering to the human patient 400 mg of at least one compound chosen from PRN1008 and pharmaceutically acceptable salts thereof once a day or twice a day. In some embodiments, the methods comprise administering to the human patient 400 mg of at least one compound chosen from PRN1008 and pharmaceutically acceptable salts thereof once a day. In some embodiments, the methods comprise administering to the human patient 400 mg of at least one compound chosen from PRN1008 and pharmaceutically acceptable salts thereof twice a day.

In some embodiments, the methods comprise administering to the human patient 300 mg of at least one compound chosen from PRN1008 and pharmaceutically acceptable salts thereof twice a day.

In some embodiments, the human patient has primary ITP. In some embodiments, the human patient has secondary ITP. In some embodiments, the human patient has chronic ITP. In some embodiments, the human patient has relapsing ITP. In some embodiments, the human patient has refractory ITP.

In some embodiments, the human patient has at least one characteristic prior to the start of the treatment period chosen from:
an age of from 18 years to 80 years;
no available and approved therapeutic options;
a platelet count of less than 30,000/μL;
an ITP duration of at least one month;
a history of taking at least one prior ITP therapy; and
splenectomy.

In some embodiments, the human patient has at least 2 characteristics prior to the start of the treatment period chosen from:
an age of from 18 years to 80 years;
no available and approved therapeutic options;
a platelet count of less than 30,000/μL;
an ITP duration of at least one month;
a history of taking at least one prior ITP therapy; and
splenectomy.

In some embodiments, the human patient has at least 3 characteristics prior to the start of the treatment period chosen from:
an age of from 18 years to 80 years;
no available and approved therapeutic options;
a platelet count of less than 30,000/μL;
an ITP duration of at least one month;
a history of taking at least one prior ITP therapy; and
splenectomy.

In some embodiments, the human patient has at least 4 characteristics prior to the start of the treatment period chosen from:
an age of from 18 years to 80 years;
no available and approved therapeutic options;
a platelet count of less than 30,000/μL;
an ITP duration of at least one month;
a history of taking at least one prior ITP therapy; and
splenectomy.

In some embodiments, the human patient has at least 5 characteristics prior to the start of the treatment period chosen from:
an age of from 18 years to 80 years;
no available and approved therapeutic options;
a platelet count of less than 30,000/μL;
an ITP duration of at least one month;
a history of taking at least one prior ITP therapy; and
splenectomy.

In some embodiments, the human patient has all of the following characteristics prior to the start of the treatment period:
an age of from 18 years to 80 years;
no available and approved therapeutic options;
a platelet count of less than 30,000/μL;
an ITP duration of at least one month;
a history of taking at least one prior ITP therapy; and
splenectomy.

In some embodiments, the human patient is from 21 to 74 years old prior to the start of the treatment period.

In some embodiments, the human patient has 2 platelet counts of less than 30,000/μL prior to the start of the treatment period. In some embodiments, the human patient has 2 platelet counts of less than 30,000/μL prior to the start of the treatment period, wherein the 2 counts are measured no sooner than 7 days apart. In some embodiments, the human patient has 2 platelet counts of less than 30,000/μL prior to the start of the treatment period, wherein the 2 counts are measured no sooner than 7 days apart in the 15 days prior to the start of the treatment period.

In some embodiments, the human patient has a platelet count of less than 30,000/µL for at least 2 consecutive platelet counts prior to the start of the treatment period. In some embodiments, the human patient has a platelet count of less than 30,000/µL for at least 2 consecutive platelet counts prior to the start of the treatment period, wherein the 2 counts are measured no sooner than 7 days apart. In some embodiments, the human patient has a platelet count of less than 30,000/µL for at least 2 consecutive platelet counts prior to the start of the treatment period, wherein the 2 counts are measured no sooner than 7 days apart in the 15 days prior to the start of the treatment period.

In some embodiments, the average of the human patient's two most recent platelet counts prior to the start of the treatment period is from 3,000/µL to 28,000/µL. In some embodiments, the average of the human patient's two most recent platelet counts prior to the start of the treatment period is from 3,000/µL to 28,000/µL, wherein the two counts are measured no sooner than 7 days apart. In some embodiments, the average of the human patient's two most recent platelet counts prior to the start of the treatment period is from 3,000/µL to 28,000/µL, wherein the two counts are measured no sooner than 7 days apart in the 15 days prior to the start of the treatment period.

In some embodiments, the average of the human patient's two most recent platelet counts prior to the start of the treatment period is from 3,000/µL to 33,000/µL. In some embodiments, the average of the human patient's two most recent platelet counts prior to the start of the treatment period is from 3,000/µL to 33,000/µL, wherein the two counts are measured no sooner than 7 days apart. In some embodiments, the average of the human patient's two most recent platelet counts prior to the start of the treatment period is from 3,000/µL to 33,000/µL, wherein the two counts are measured no sooner than 7 days apart in the 15 days prior to the start of the treatment period.

In some embodiments, the average of the human patient's two most recent platelet counts prior to the start of the treatment period and the human patient's platelet count on the first day of the treatment period is from 3,000/µL to 28,000/µL. In some embodiments, the average of the human patient's two most recent platelet counts prior to the start of the treatment period, wherein the two counts are measured no sooner than 7 days apart, and the human patient's platelet count on the first day of the treatment period is from 3,000/µL to 28,000/µL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/µL to 28,000/µL.

In some embodiments, the average of the human patient's two most recent platelet counts prior to the start of the treatment period and the human patient's platelet count on the first day of the treatment period is from 3,000/µL to 15,000/µL. In some embodiments, the average of the human patient's two most recent platelet counts prior to the start of the treatment period, wherein the two counts are measured no sooner than 7 days apart, and the human patient's platelet count on the first day of the treatment period is from 3,000/µL to 15,000/µL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/µL to 15,000/µL.

In some embodiments, the average of the human patient's two most recent platelet counts prior to the start of the treatment period and the human patient's platelet count on the first day of the treatment period is from 3,000/µL to 33,000/µL. In some embodiments, the average of the human patient's two most recent platelet counts prior to the start of the treatment period, wherein the two counts are measured no sooner than 7 days apart, and the human patient's platelet count on the first day of the treatment period is from 3,000/µL to 33,000/µL. In some embodiments, the average of the human patient's two most recent platelet counts prior to the start of the treatment period, wherein the two counts are measured no sooner than 7 days apart in the 15 days prior to the start of the treatment period, and the human patient's platelet count on the first day of the treatment period is from 3,000/µL to 33,000/µL.

In some embodiments, the human patient had ITP for at least 2 months prior to the start of the treatment period. In some embodiments, the human patient had ITP for at least 3 months prior to the start of the treatment period. In some embodiments, the human patient had ITP for at least 4 months prior to the start of the treatment period. In some embodiments, the human patient had ITP for at least 5 months prior to the start of the treatment period. In some embodiments, the human patient had ITP for at least 6 months prior to the start of the treatment period.

In some embodiments, the human patient had ITP for at least 1 year prior to the start of the treatment period. In some embodiments, the human patient had ITP for at least 2 years prior to the start of the treatment period. In some embodiments, the human patient had ITP for at least 3 years prior to the start of the treatment period. In some embodiments, the human patient had ITP for at least 4 years prior to the start of the treatment period. In some embodiments, the human patient had ITP for at least 5 years prior to the start of the treatment period. In some embodiments, the human patient had ITP for at least 6 years prior to the start of the treatment period. In some embodiments, the human patient had ITP for at least 7 years prior to the start of the treatment period. In some embodiments, the human patient had ITP for at least 8 years prior to the start of the treatment period. In some embodiments, the human patient had ITP for at least 9 years prior to the start of the treatment period.

In some embodiments, the human patient had ITP for at least 10 years prior to the start of the treatment period. In some embodiments, the human patient had ITP for at least 20 years prior to the start of the treatment period. In some embodiments, the human patient had ITP for at least 30 years prior to the start of the treatment period. In some embodiments, the human patient had ITP for at least 40 years prior to the start of the treatment period. In some embodiments, the human patient had ITP for at least 50 years prior to the start of the treatment period.

In some embodiments, the human patient has a history of taking from 1 to 41 prior ITP therapies prior to the start of the treatment period. In some embodiments, the human patient has a history of taking from 1 to 54 prior ITP therapies prior to the start of the treatment period.

In some embodiments, the human patient has a history of taking at least one prior ITP therapy prior to the start of the treatment period. In some embodiments, the human patient has a history of taking at least 2 prior ITP therapies prior to the start of the treatment period. In some embodiments, the human patient has a history of taking at least 3 prior ITP therapies prior to the start of the treatment period. In some embodiments, the human patient has a history of taking at least 4 prior ITP therapies prior to the start of the treatment period. In some embodiments, the human patient has a history of taking at least 5 prior ITP therapies prior to the start of the treatment period. In some embodiments, the human patient has a history of taking at least 6 prior ITP therapies prior to the start of the treatment period. In some embodiments, the human patient has a history of taking at least 7 prior ITP therapies prior to the start of the treatment period. In some embodiments, the human patient has a history of taking at least 8 prior ITP therapies prior to the start of the treatment period. In some embodiments, the human patient has a history of taking at least 9 prior ITP therapies prior to the start of the treatment period.

In some embodiments, the human patient has a history of taking at least 10 prior ITP therapies prior to the start of the treatment period. In some embodiments, the human patient has a history of taking at least 15 prior ITP therapies prior to the start of the treatment period. In some embodiments, the human patient has a history of taking at least 20 prior ITP therapies prior to the start of the treatment period. In some embodiments, the human patient has a history of taking at least 25 prior ITP therapies prior to the start of the treatment period. In some embodiments, the human patient has a history of taking at least 30 prior ITP therapies prior to the start of the treatment period. In some embodiments, the human patient has a history of taking at least 35 prior ITP therapies prior to the start of the treatment period. In some embodiments, the human patient has a history of taking at least 40 prior ITP therapies prior to the start of the treatment period. In some embodiments, the human patient has a history of taking at least 45 prior ITP therapies prior to the start of the treatment period. In some embodiments, the human patient has a history of taking at least 50 prior ITP therapies prior to the start of the treatment period.

In some embodiments, the at least one prior ITP therapy is chosen from corticosteroids, thrombopoietin receptor agonists, intravenous immunoglobulin, anti-D immunoglobulin, and rituximab.

In some embodiments, the human patient had a splenectomy prior to the start of the treatment period.

In some embodiments, the at least one compound chosen from PRN1008 and pharmaceutically acceptable salts thereof is administered as a monotherapy.

In some embodiments, the at least one compound chosen from PRN1008 and pharmaceutically acceptable salts thereof is administered in combination with at least one concomitant ITP therapy.

In some embodiments, the at least one concomitant ITP therapy is chosen from corticosteroids and thrombopoietin receptor agonists. In some embodiments, the at least one concomitant ITP therapy is chosen from corticosteroids, eltrombopag, and romiplostim.

In some embodiments, the at least one compound chosen from PRN1008 and pharmaceutically acceptable salts thereof comprises at least one compound chosen from the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof comprises at least one compound chosen from the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof comprises a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt of the foregoing.

In some embodiments, the at least one compound chosen from PRN1008 and pharmaceutically acceptable salts thereof consists of at least one compound chosen from the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof consists of at least one compound chosen from the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

In some embodiments, the at least one compound chosen from PRN1008 and pharmaceutically acceptable salts thereof consists of a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt of the foregoing.

In some embodiments, the present disclosure is directed to a method for treating immune thrombocytopenia in a human patient comprising: administering to the patient a dose chosen from 400 mg once daily (QD), 300 mg twice daily (BID), and 400 mg BID of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008).

In some embodiments, PRN1008 comprises a mixture of (E) and (Z) isomers of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile. Further, in some embodiments, PRN1008 is formulated as a pharmaceutical composition and the pharmaceutical composition comprises one or more pharmaceutical acceptable carriers or excipients. For example, in some embodiments, the pharmaceutical composition comprises microcrystalline cellulose, crospovidone, and sodium stearyl fumarate with a film coating.

In some embodiments of the present disclosure, the method further comprises repeating the administration of PRN1008 to the patient over a treatment period. Additionally, in some embodiments, the treatment period ranges from 28 days to 168 days, for a minimum of 8 days or from 8 days to 28 days.

In some embodiments, the present disclosure provides that before administration, the patient's platelet count is less than 30,000/μL for two or more consecutive platelet counts. Further, in some embodiments, after administration over a treatment period, the patient obtains two or more consecutive platelet counts, separated by at least 5 days, of ≥50,000/μL; the treatment period ranges from 28 days to 168 days. Additionally, in some embodiments, after administration over a treatment period, the patient has a stable response of a platelet count of greater than or equal to 50,000/μL during the treatment period and an increase of platelet count of ≥20,000/μL from baseline.

In some embodiments, the present disclosure provides that before administration, the patient has relapsed or refractory idiopathic thrombocytopenia, which is primary or secondary to other diseases afflicting the patient. For example, in some embodiments, the patient has secondary ITP. In some embodiments, the patient is administered a dose of 400 mg QD.

In some embodiments, the present disclosure is directed to the occurrence where the patient is also taking one or more concomitant medications. For example, in some embodiments, the one or more concomitant medication is chosen from corticosteroids, eltrombopag, and romiplostim.

In some embodiments, the present disclosure is directed to a method for treating immune thrombocytopenia in a human patient comprising: administering to the patient a dose chosen from 400 mg once daily (QD), 300 mg twice daily (BID), and 400 mg BID of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008), wherein before administration, the patient's platelet count is less than 30,000/μL for two or more consecutive platelet counts, and wherein after administration, the patient has a stable response of a platelet count of greater than or equal to 50,000/μL during the treatment period.

In some embodiments, the present disclosure is directed to a method for treating immune thrombocytopenia in a human patient comprising: administering to the patient a dose chosen from 400 mg once daily (QD), 300 mg twice daily (BID), and 400 mg BID of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (PRN1008), wherein before administration, the patient's platelet count is less than 30,000/μL for two or more consecutive platelet counts, and after administration over a treatment period, the patient obtains two or more consecutive platelet counts, separated by at least 5 days, of ≥50,000/μL and an increase of platelet count of ≥20,000/μL from baseline.

Pharmaceutical Compositions

In some embodiments of the present disclosure, PRN1008 is administered as part of a pharmaceutical composition comprising: at least one compound chosen from PRN1008 and pharmaceutically acceptable salts thereof; and at least one pharmaceutically acceptable excipient. In some embodiments, the pharmaceutical composition is in the form of at least one tablet.

In some embodiments of the present disclosure, PRN1008 is orally administered as part of a pharmaceutical composition comprising: at least one compound chosen from PRN1008 and pharmaceutically acceptable salts thereof; and at least one pharmaceutically acceptable excipient. In some embodiments, the pharmaceutical composition is in the form of at least one tablet. In some embodiments, the pharmaceutical composition is in the form of at least one tablet comprising 100 mg or 300 mg of PRN1008. In some embodiments, the pharmaceutical composition is in the form of at least one tablet comprising 100 mg of PRN1008. In some embodiments, the pharmaceutical composition is in the form of at least one tablet comprising 300 mg of PRN1008.

In some embodiments, PRN1008 is administered in the form of a film-coated tablet.

In some embodiments of the present disclosure, PRN1008 is administered in the form of at least one tablet comprising: at least one compound chosen from PRN1008 and pharmaceutically acceptable salts thereof; and at least one pharmaceutically acceptable excipient. In some embodiments, PRN1008 is administered in the form of at least one tablet comprising: at least one compound chosen from PRN1008 and pharmaceutically acceptable salts thereof; at least one filler; at least one disintegrant; at least one lubricant; and at least one film coating. In some embodiments, the at least one filler is microcrystalline cellulose. In some embodiments, the at least one disintegrant is crospovidone. In some embodiments, the at least one lubricant is sodium stearyl fumarate.

In some embodiments of the present disclosure, PRN1008 is administered in the form of at least one tablet comprising: 100 mg of at least one compound chosen from PRN1008 and pharmaceutically acceptable salts thereof; and at least one pharmaceutically acceptable excipient. In some embodiments, PRN1008 is administered in the form of at least one tablet comprising: 100 mg of at least one compound chosen from PRN1008 and pharmaceutically acceptable salts thereof; at least one filler; at least one disintegrant; at least one lubricant; and at least one film coating. In some embodiments, the at least one filler is microcrystalline cellulose. In some embodiments, the at least one disintegrant is crospovidone. In some embodiments, the at least one lubricant is sodium stearyl fumarate.

In some embodiments of the present disclosure, PRN1008 is administered in the form of at least one tablet comprising: 300 mg of at least one compound chosen from PRN1008 and pharmaceutically acceptable salts thereof; and at least one pharmaceutically acceptable excipient. In some embodiments, PRN1008 is administered in the form of at least one tablet comprising: 300 mg of at least one compound chosen from PRN1008 and pharmaceutically acceptable salts thereof; at least one filler; at least one disintegrant; at least one lubricant; and at least one film coating. In some embodiments, the at least one filler is microcrystalline cellulose. In some embodiments, the at least one disintegrant is crospovidone. In some embodiments, the at least one lubricant is sodium stearyl fumarate.

In some embodiments, PRN1008 is administered with a glass of water.

In some embodiments, PRN1008 is administered with food.

In some embodiments, PRN1008 is administered without food.

The proportion and nature of any pharmaceutically acceptable excipient may be determined by the chosen route of administration and standard pharmaceutical practice. Except insofar as any conventional pharmaceutically acceptable excipient is incompatible with PRN1008, such as by producing any undesirable biological effect or otherwise interacting in a deleterious manner with any other component(s) of the pharmaceutically composition, its use is contemplated to be within the scope of this disclosure.

Some non-limiting examples of materials which may serve as pharmaceutically acceptable excipients include: (1) sugars, such as, e.g., lactose, glucose, and sucrose; (2) starches, such as, e.g., corn starch and potato starch; (3) cellulose and its derivatives, such as, e.g., sodium carboxymethyl cellulose, ethyl cellulose, and cellulose acetate; (4) powdered tragacanth; (5) malt; (6) gelatin; (7) talc; (8) excipients, such as, e.g., cocoa butter and suppository waxes; (9) oils, such as, e.g., peanut oil, cottonseed oil, safflower oil, sesame oil, olive oil, corn oil, and soybean oil; (10) glycols, such as, e.g., propylene glycol; (11) polyols, such as, e.g., glycerin, sorbitol, mannitol, and polyethylene glycol; (12) esters, such as, e.g., ethyl oleate and ethyl laurate; (13) agar; (14) buffering agents, such as, e.g., magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York also discloses additional non-limiting examples of pharmaceutically acceptable excipients, as well as known techniques for preparing and using the same.

One skilled in the art can readily select the proper form and route of administration depending upon the disorder or condition to be treated, the stage of the disorder or condition, and other relevant circumstances.

EXAMPLES

The following example is intended to be illustrative and is not meant in any way to limit the scope of the disclosure.

Abbreviations

AE Adverse event
ALP Alkaline phosphatase
ALT Alanine aminotransferase
ANC Absolute neutrophil count
aPTT Activated partial thromboplastin time
AST Aspartate aminotransferase
AUC Area under the plasma concentration-time curve
bid/BID Twice daily (morning and evening)
BP Blood pressure
BTK Bruton's Tyrosine Kinase
CA Competent Authority
CBC Complete blood count
CI Confidence Interval
CL/F Apparent total clearance of the drug from plasma after oral administration
CLL Chronic lymphocytic leukemia
Cmax Maximum observed plasma concentration
CPK Creatine phosphokinase
CRF Case report form
CRO Contract research organization
CTCAE Common Terminology Criteria for AEs
CYP Cytochrome P450
D Day
DLT Dose-limiting toxicity
EC Ethics Committee
ECG Electrocardiogram
EDC Electronic Data Capture
EQ-5D VAS Euro-QoL 5-Dimension Visual Analog Scale
FSH Follicle Stimulating Hormone
GCP Good Clinical Practice
GFR Glomerular Filtration Rate
H2 Histamine two (receptor)
HCV Hepatitis C Virus
HDPE High-density polyethylene
HIV Human Immunodeficiency Virus
HR Heart rate
IB Investigator's Brochure
ICH International Conference on Harmonization
IDSM Independent Data Safety Monitor
IR Immediate release
IRB Institutional Review Board (Human Research Ethics Committee)
ITP Immune Thrombocytopenic Purpura
ITP-BAT Idiopathic Thrombocytopenic Purpura Bleeding Assessment Tool
IVIG Intravenous immunoglobulin
LPLV Last participant last visit
LTE Long term extension
MAD Multiple ascending dose (trial)
MedDRA Medical Dictionary for Regulatory Activities
NK Natural killer (cell)
NSAID Non-Steroidal Anti-Inflammatory Drug
OTC Over the counter
PK Pharmacokinetic
PT/INR Prothrombin Time/International Normalized Ratio
PV Pemphigus vulgaris
PVG Pharmacovigilance
qd/QD Once a day
QoL Quality of Life
QTcF QT interval corrected for heart rate (Fridiricia Correction)
RR Resting Rate
SAE Serious adverse event
SAP Statistical Analytical Plan
SI Systeme international d'unités (International system of units)
SMC Safety Monitoring Committee
SUSAR Suspected Unexpected Serious Adverse Reaction
TEAE Treatment-Emergent Adverse Event
Tmax Time of observed maximum plasma concentration
TPO Thrombopoietin
t½ Elimination half-life
ULN Upper limit of normal
USUBJID Unique subject identifier
VAS Visual analog scale
WBC White blood cell
WHODD World Health Organization Drug Dictionary Example 1: An Adaptive, Open-Label, Dose-Finding, Phase ½ Study Investigating the Safety, Pharmacokinetics, and Clinical Activity of PRN1008, an Oral BTK Inhibitor, in Patients with Relapsed/Refractory Immune Thrombocytopenia An ongoing phase ½ clinical trial (NCT03395210) investigating the safety, pharmacokinetics, and clinical activity of PRN1008, an oral BTK inhibitor, in patients with relapsed/refractory immune thrombocytopenia (ITP) began enrolling patients on Mar. 22, 2018. As of Oct. 6, 2020, the estimated primary completion date for the study is September 2022, with an estimated study completion date of September 2023. To date, PRN1008 has been well-tolerated in ITP patients with no reported treatment-related bleeding or thrombotic events. Moreover, positive preliminary results have been observed in a highly treatment-resistant and refractory patient population.

The key inclusion criteria for the phase ½ study are: adults aged 18-80 years old with relapsed/refractory ITP; ITP primary or secondary to other diseases (e.g., systemic lupus erythematosus, chronic lymphocytic leukemia); no other available/approved treatment options; ≥2 platelet counts<30,000/µL at study entry; and adequate hematologic, hepatic, and renal function. Key exclusion criteria included: pregnant or lactating women; current drug or alcohol abuse; history of solid organ transplant; and positive screening for HIV, hepatitis B, or hepatitis C. Enrolled patients have low platelet counts, having relapsed on or been refractory to prior therapies with no available and approved therapeutic options and may continue corticosteroids and/or thrombopoietin mimetics during the study. For example, stable concomitant corticosteroid (CS) or thrombopoietin receptor agonist (TPO-RA) treatment is permitted during the study.

The sample size employed in the study is based on clinical considerations with the intention of gaining a sufficiently high confidence level in the study results using normal approximation methods.

Figure 2:
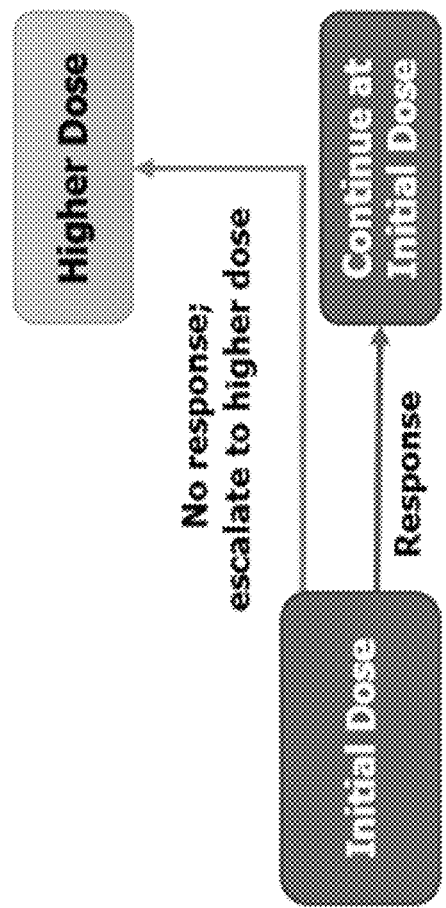
FIG. 2 depicts the dose-escalation rules for the dose-finding portion of an adaptive, open-label, dose-finding, phase ½ study investigating PRN1008 in ITP patients.

The completed PRN1008 intrapatient dose escalation portion of the study used a 3+3 design. Specifically, if response was observed in 1 of 3 patients, then 3 more patients were added to the dose level. However, if no response was observed in 3 patients for 28 days, the dose was dropped, and patients were escalated to higher doses and all subsequently enrolled patients started treatment at the higher dose. During the dose escalation portion, patients were orally dosed with PRN1008 for an active treatment period of 24 weeks at doses of 200 and 400 mg qd and 300 and 400 mg bid. If patients exhibited a response at an initial dose, the patient continued at that dose (FIG. 2). If the patient did not respond to the initial dose, the dose was escalated to a higher dose. Patients were monitored frequently by weekly platelet counts and complete blood counts (CBCs) throughout the active treatment period. PK samples were collected intensively on the first day of each new, higher dose level and at random times following dosing at each on-treatment follow up visit to assess dose response. Other standard clinical and laboratory assessments of patients with ITP were also employed in the dose escalation study, including a bleeding assessment (ITP-BAT; Rodeghiero 2013) that has been used in prior ITP trials.

The safety objective of the phase ½ study is to characterize the safety and tolerability of up to four dose levels of PRN1008 in patients with ITP. In the study, safety is assessed by the incidence, severity, and relationship of TEAEs, including clinically significant changes in physical examination, laboratory tests, and vital signs. Adverse events are categorized as treatment emergent after the first dose of PRN1008 has been received. TEAEs in the post-treatment follow-up period are also assessed and examined for possible relationship to the prior PRN1008 treatment. TEAEs include all AEs that start on or after the first dose of study medication, or AEs that are present prior to the first dose of study medication, but their severity or relationship increases after the first dose of study medication up to and including the final study medication dosing date. Within each preferred term, patients are counted only once if they had more than one event reported during the dosing period.

The pharmacokinetic objective of the study is to characterize the pharmacokinetics of PRN1008 in patients with ITP. Plasma PK parameters ($C_{max}$, $T_{max}$, AUC, $t_{1/2}$, V/F, CL/F) of PRN1008 in ITP patients are evaluated in each patient based on frequent sampling on Day 1 of a new, higher dosing level and reported by dose and, if relevant, overall. Non-compartmental analysis is employed to derive PK parameters for each individual. Results are reported by descriptive statistics, and exploratory analyses may pool these data with the data from other studies of PRN1008.

Efficacy objectives of the study include: (1) to explore the clinical activity of up to four dose levels of PRN1008 in relapsed/refractory patients with ITP (200 and 400 mg qd; 300 and 400 mg bid); and (2) to identify a potential dose regimen to use in future studies of PRN1008 in patients with ITP. The dose-finding/dose escalation portion of the study has been completed, and all enrolled patients are currently being treated with 400 mg bid.

In Part A of the study, the primary efficacy outcome measure is consecutive increased platelet counts, i.e., two or more consecutive platelet counts≥50,000/µL without requiring rescue medication. Specifically, Part A examines the proportion of patients able to achieve two or more consecutive platelet counts, separated by at least 5 days, of ≥50,000/µL and an increase of platelet count of ≥20,000/µL from baseline, without use of rescue medication in the 4 weeks prior to the latest elevated platelet count. The analysis of the primary efficacy endpoint is a weighted logistic regression, with the binary indicator of platelet response as the dependent variable, and dose level in total mg per day as a covariate, weighted by the number of days the patient was on the dose.

Additional efficacy endpoints include: any 2 platelet counts≥50,000/µL; platelet responses over time, by duration of treatment, and clinical benefit (≥30,000/µL; stable response (platelet counts≥50,000/µL at 50% of visits for 4 of the last 8 weeks of active treatment). For example, secondary efficacy endpoints of the study include: (1) proportion of patients able to achieve two or more platelet counts of ≥50,000/µL and increase of platelet count of ≥20,000/µL from baseline at any time (on treatment or during follow up) without use of rescue medication in the 4 weeks prior to the latest elevated platelet count; (2) proportion of patients able to achieve two or more platelet counts, separated by at least 5 days, representing an increase of platelet count of ≥20,000/µL from baseline, by dose level, without use of rescue medication in the 4 weeks prior to the latest elevated platelet count; (3) proportion of patients able to achieve two or more platelet counts, separated by at least 5 days, of ≥100,000/µL, by dose level, without use of rescue medication in the 4 weeks prior to the latest elevated platelet count; (4) change from baseline to the average of the last two platelet counts at each dosing level; (5) time to first platelet response (as defined in the primary endpoint); (6) proportion of patients receiving rescue medication at each dosing level and overall; (7) proportion of patients with a Grade 2 or higher bleeding event at each dosing level and overall; (8) bleeding scale (ITP-BAT scale) at the end of treatment period for each dosing level; and (9) proportion of patients that completed 24 weeks of treatment and demonstrated a platelet response defined as platelet counts≥50,000/µL at ≥50% of the visits during the last 8 weeks of the active treatment period.

Exploratory objectives of the study include: the effect of PRN1008 on platelet autoantibody levels; the effect of PRN1008 on markers of hemolysis; the effect of PRN1008 on thrombopoietin (TPO) levels; the effect of PRN1008 on quality of life (QoL) using the Euro-QoL 5-Dimension Visual Analog Scale (EQ-5D VAS); and plasma metabolite analysis/identification for PRN1008.

Rationale for Doses Used and Duration of Study:

An adaptive, open-label, dose-finding study using rule-based intrapatient dose escalation is an appropriate phase ½ design to evaluate the safety and effect of PRN1008 in patients with ITP, a relatively rare autoimmune disease. The study design is similar to that used to study the initial efficacy and safety of the orally available tyrosine kinase inhibitor fostamatinib in ITP (Podolanczuk et al., 2009).

Figures 3A, 3B:
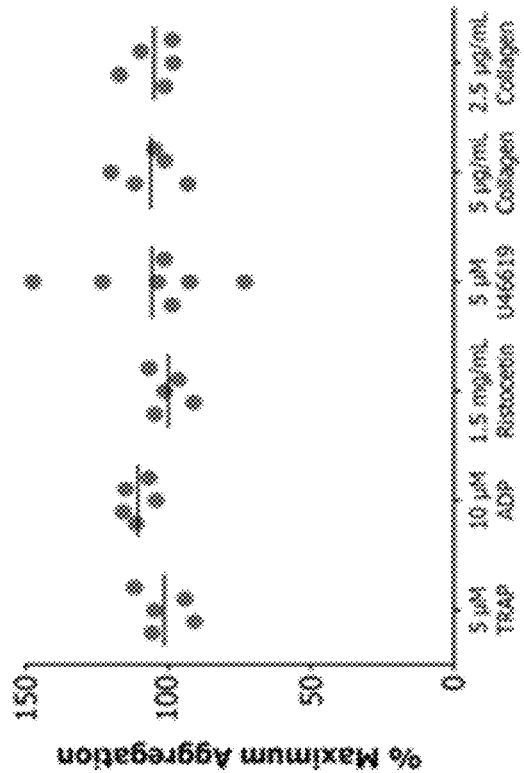
FIG. 3A depicts the effects of 1 μM PRN1008 on platelet function as assessed in vitro in normal healthy volunteer blood platelets using a standard panel of platelet agonists.
FIG. 3B depicts the effects of 1 μM PRN1008 on platelet function as assessed in vitro in ITP patient blood platelets using a standard panel of platelet agonists.
Figure 4:
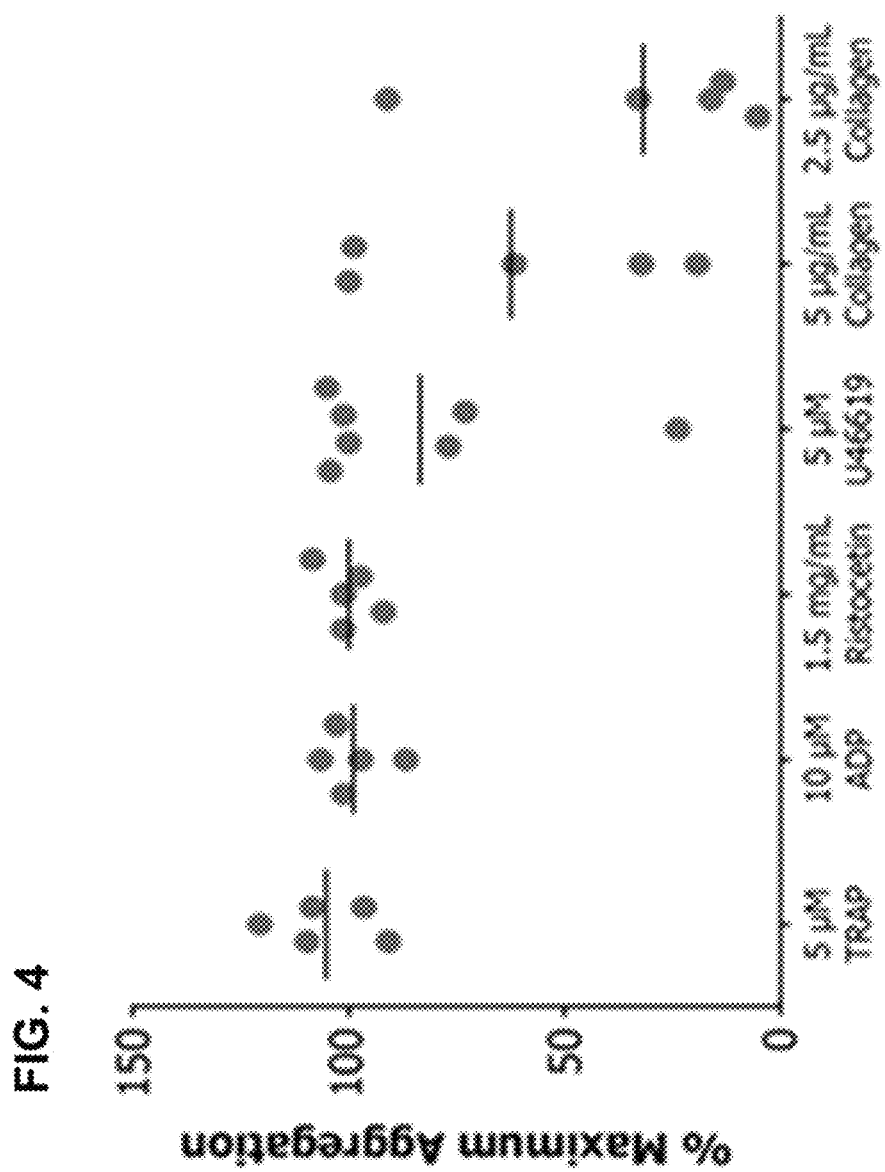
FIG. 4 depicts the effects of 1 μM ibrutinib on platelet function as assessed in vitro in normal healthy volunteer blood platelets using a standard panel of platelet agonists.

The dose and exposure explored in this study has been previously well-tolerated in human studies and their inter-relationships well-characterized. Platelets express high levels of BTK; however, alternative signaling pathways exist which bypass BTK signaling to retain normal platelet functions. PRN1008 had no effect on the platelet aggregation from the blood of healthy volunteers or ITP patients tested ex vivo (≤1 µM) using a standard panel of platelet agonists (FIGS. 3A, 3B). For example, ex vivo treatment with PRN1008 at clinically relevant concentrations did not impact collagen-induced platelet aggregation in either normal or ITP patient platelet samples, or interfere with responses to all other platelet agonists tested. In contrast, the BTK inhibitor ibrutinib has significant effects on platelet aggregation in healthy volunteers (FIG. 4).

Based on BTK occupancies in a mouse model of anti-platelet driven immune thrombocytopenia, the 200 mg qd human starting dose was expected to result in minimal improvement in platelet counts. In that model, a 10 mg/kg/d dose was associated with mean 51% BTK occupancy 1 h post-dose, along with a slight increase in platelet count over vehicle control (mean 83.1% platelet decrease from baseline for vehicle with anti-platelet challenge, compared to a 71.9% platelet decrease for PRN1008 10 mg/kg/d). The top dose of 40 mg/kg/d in that model resulted in a maximum BTK occupancy of 91%, matching the expected peak occupancies with the maximum 400 mg QD and 400 mg BID doses. The 400 mg BID dose was expected to produce higher trough, or pre-dose BTK occupancies of approximately 70% vs. 50% for QD dosing, while having similar peak values. Dosing above 400 mg BID is thought unlikely to result in greater target inhibition.

In prior studies, no accumulation in exposure has been observed with multiple dosing of PRN1008 when administered once daily, with a small amount of accumulation observed with twice daily dosing.

The blistering disease pemphigus is an autoantibody-driven disease like ITP. In Study PRN1008-005, a rapid onset of clinical effect was seen in most pemphigus patients within 4 weeks, with continued improvement to very low levels of skin inflammation by the end of 12 weeks of therapy. Therefore, 28-day cycles to assess the initial platelet response and trigger intrapatient dose-escalation were deemed appropriate for studying ITP. Additionally, a 24-week overall treatment period was preferred for the dose-finding study to enable all patients to potentially dose-escalate to the higher doses and be fully evaluated at those doses.

Dose Escalation Study Design:

Patients in the dose-escalation portion of the study were assigned to 4 cohorts, as shown in Table 1. The starting dose levels were 200 mg QD; 400 mg QD; 600 mg per day (300 mg BID); 800 mg per day (400 mg BID). Due to the study design, not all patients were necessarily dosed at all dose levels shown in Table 1. The "sentinel cohorts" at each dose level consisted of the first 3 patients, or 6, if 3 extra were added for a dose-limiting toxicity (DLT) event or platelet response (as defined in the primary endpoint and sustained for at least 3 of 4 consecutive platelet counts at any dose level). To be evaluable in a sentinel cohort, patients must have ≥75% compliance over the 28-day dosing period.

The following dose escalation rules applied in the study. Individual patients dose-escalate to successive dose levels unless they are withdrawn, have a platelet response at the current dose level, or the next dose level has been determined to be ineligible for further enrollment due to safety concerns. Patients experiencing a platelet response (as defined for the primary endpoint) will not have their dose escalated at the next cycle. If they do not experience a platelet response during the second cycle of the same dose level, then they may dose escalate for the following cycle. If they require rescue medication subsequently because the platelet response was only transient, these patients will be discontinued from the study. Patients experiencing a DLT will be discontinued from the study. Additionally, pregnant patients and patients with abnormal liver function tests suggestive of DILI, defined as: CTCAE≥Grade 3 elevation of ALT and/or AST (i.e. ALT or ALT>5×ULN) or ALT or AST>3×ULN with total bilirubin>2×ULN without ALP>2× ULN in the absence of another cause will be discontinued.

The DLT evaluation period for any patient is defined as the duration of PRN1008 dosing. Dose-limiting toxicity in the phase ½ study, including the completed dose escalation study, is established as follows. Hematologic DLT is determined based on: ANC<500/µL for ≥5 days; Grade 3 or higher decreased hemoglobin in the absence of a pre-existing Grade 2 decreased hemoglobin; febrile neutropenia, with absolute neutrophil count (ANC)<1000/mm$^3$ and single temperature>38.3 degrees C. (101 degrees F.) or a sustained temperature of ≥38° C. (100.4° F.) for more than one hour (CTCAE, version 4.0); and ≥Grade 3 or higher bleeding event requiring platelet transfusion. Non-hematologic DLT is considered any >Grade 3 non-hematologic toxicity per the NCI Common Terminology Criteria for Adverse Events (CTCAE), version 4.0, with the following exceptions: laboratory TEAEs that are asymptomatic and return to baseline or to Grade 1 within 7 days; fatigue; nausea, vomiting or diarrhea that return to baseline or Grade 1 within 7 days; and systemic reactions (such as, e.g., fever, headache) that return to baseline or Grade 1 within 7 days. Any toxicity that, at the discretion of the Investigator, is thought to warrant withholding the study drug for more than 7 days is also considered a DLT.

In Table 1, n indicates the expected enrollment in each cohort unless a sustained platelet response was seen or a DLT, in which case 3 extra patients would be added to that group. A starting dose level could be dropped for futility after 3 or 6 patients were evaluated, or retained if efficacy is observed. Notably, individual patients in each cohort do not dose-escalate when there is a platelet response at a lower dose level or toxicity. If several dose levels are therapeutic, some or all patients would not reach the higher dose levels.

TABLE 1

Adaptive Cohort Dosing

| Cohort | Starting dose level (n) 4 weeks | Next dose level 4 weeks | Next dose level** 4 weeks | Next dose level** | Next dose level** | Next dose level** |
|---|---|---|---|---|---|---|
| 1 | 200 mg QD (3-6) | 400 mg QD | 300 mg BID | 400 mg BID | 400 mg BID | 400 mg BID |
| 2 | 400 mg QD (≤6) | 300 mg BID | 400 mg BID | 400 mg BID | 400 mg BID | 400 mg BID |
| 3 | 300 mg BID (≤6) | 400 mg BID | 400 mg BID | 400 mg BID | 400 mg BID | 400 mg BID |
| 4 | 400 mg BID (≤6) | 400 mg BID | 400 mg BID | 400 mg BID | 400 mg BID | 400 mg BID |

Each patient enrolled in the dose-escalation portion of the study was allowed to up-titrate their dose after 28 days of PRN1008 therapy at each dose level if they did not experience a platelet response (as defined in the primary endpoint) or a DLT at the last dose level. If they experienced a platelet response in the first cycle at any one dose level but did not have a platelet response in the second cycle at that dose, they could dose escalate at the end of the second cycle. Patients experiencing a platelet response (as defined for the primary endpoint) did not have their dose escalated at the next cycle.

Patients could receive PRN1008 treatment for up to 24 weeks, starting on Day 1 and ending on Study Day 169, followed by 4 weeks of post-treatment safety follow-up. However, patients who dose escalated to 400 mg BID could continue in the active treatment period until 24 weeks of treatment at the 400 mg BID dose were completed.

Patients were monitored with weekly platelet counts and CBCs throughout the dose-escalation study. Additionally, PK samples were collected intensively on the first day of each new, higher dose level and at random times following dosing at each on-treatment follow up visit.

Long Term Extension (LTE):

After completing an active treatment period in the phase ½ study (such as, e.g., the dose escalation study), patients demonstrating a platelet response defined as platelet counts≥50,000/μL at ≥50% of the visits during the last 8 weeks of the active treatment period are allowed to enter the Long Term Extension (LTE) to receive study drug at the 400 mg BID dose. Patients may continue in the LTE until the patient is: no longer responding per the LTE-defined platelet response and/or experiences dose limiting toxicities; the drug is no longer being developed by the Sponsor; the program is stopped for safety reasons; or the drug becomes commercially available in the patient's country.

Patients who continue into the LTE will be monitored with weekly platelet counts and CBC's for the first 6 months, and then monthly for an additional 6 months, then once every 3 months.

Patients who previously completed the study, were responders per the LTE requirement, and did not experience a DLT were eligible to enroll in the LTE.

Concomitant Medications:

All patients can receive, but are not required to be taking, concomitant corticosteroids. The dose should be fixed (±10%) for at least 2 weeks before Day 1 and remain unchanged throughout the study unless rescue criteria are triggered. If the patient requires rescue treatment or concomitant ITP drug increases of more than 10% of the Day 1 daily dose, the patient will be discontinued from the study and receive rescue treatment per standard of care. These drugs may not have their dose increased as part of "rescue" medication.

All patients may receive, but are not required to be taking, eltrombopag or romiplostim. The dose should be fixed for at least 2 weeks before Day 1 and remain constant (10% variation from Day 1 daily dose is allowed) throughout the study unless there are safety concerns related to those drugs. These drugs may not have their dose increased as part of "rescue" medication.

In vitro, PRN1008 is a substrate of P-gp and CYP3A, and an inhibitor of CYP3A. When co-administered with midazolam in healthy volunteers, PRN1008 has been shown to act as a moderate CYP3A inhibitor, increasing midazolam exposure by approximately 3-fold. Moderate to strong inducers and inhibitors of cytochrome P450 3A (CYP3A) should be avoided during the study, as they may reduce or increase the exposure of PRN1008 when administered concomitantly. Additionally, clinically relevant CYP3A substrate drugs with a narrow therapeutic window are not permitted as PRN1008 is a weak to moderate CYP3A inhibitor. Other "sensitive substrates" if they are medically necessary for the patient should be monitored as concurrent use with PRN1008 will increase the blood levels of sensitive substrate drugs.

Proton pump inhibitors are not permitted during the phase ½ study as they may reduce the bioavailability of PRN1008 tablets. Co-administration of esomeprazole reduced exposure of the tablet formulation of PRN1008 by 48% in a prior study, demonstrating an impact of gastric pH on absorption. Patients could switch to H2 receptor blocking drugs as a substitute. PRN1008 should be administered 2 hours or more prior to permitted acid-reducing drugs.

Inclusion Criteria:

The following inclusion criteria are used to inform the enrollment of patients in the phase ½ study, including, e.g., the dose escalation study.

1. Male and female patients, aged 18 to 80 years old (Czech Republic and Norway only: aged 18 to 65 years old)
2. Immune-related ITP (both primary and secondary)
3. Refractory or relapsed patients with no available and approved therapeutic options with a platelet count of count<30,000/μL on two occasions no less than 7 days apart in the 15 days prior to beginning study treatment
4. A history of response (two or more platelet counts≥50,000/μL with an increase of ≥20,000/μL) to at least one prior line of therapy (with splenectomy being considered a line of therapy)
5. Adequate hematologic, hepatic, and renal function (absolute neutrophil count≥1.5×10$^9$/L, Hgb>9 g/dL, AST/ALT≤1.5×ULN, albumin≥3 g/dL, total bilirubin≤1.5×ULN, estimated GFR>60 (Cockcroft and Gault method) (C1D1 pre dose may be checked up to Day −3 prior to C1D1)
6. Female patients who are of reproductive potential must agree for the duration of active treatment in the study to use a highly effective means of contraception (hormonal contraception methods that inhibits ovulation, intrauterine device, intrauterine hormone-releasing system, bilateral tubal ligation, vasectomized partner, sexual abstinence). Unless surgically sterile, postmenopausal females should have menopause confirmed by FSH testing.
7. Able to provide written informed consent and agreeable to the schedule of assessment Additionally, participants cannot commence enrollment procedures until all entry criteria have been fulfilled. Where the clinical significance of an abnormal screening test result (lab or any other tests) is uncertain, the test may be repeated.

Exclusion Criteria

The following exclusion criteria are used to inform the enrollment of patients in the phase ½ study, including, e.g., the dose escalation study.

1. Pregnant or lactating women
2. ECG findings of QTcF>450 msec (males) or >470 msec (females), poorly controlled atrial fibrillation (i.e., symptomatic patients or a ventricular rate above 100 beats/min on ECG), or other clinically significant abnormalities
3. History or current, active malignancy requiring or likely to require chemotherapeutic or surgical treatment during the trial, with the exception of non-melanoma skin cancer 4. Transfusion with blood or blood products or plasmapheresis within 2 weeks before Day 1
5. Change in corticosteroid and/or TPO agonist dose within 2 weeks prior to Day 1 (more than 10% variation from Day 1 daily doses)
6. Use of rescue medications other than corticosteroids or TPO in exclusion #5 in the two weeks before Day 1
7. Immunosuppressant drugs other than corticosteroids—these drugs should be discontinued for at least 14 days before Day 1
8. Treatment with rituximab or splenectomy within the 3 months prior to Day 1
9. Ongoing need for the use of proton pump inhibitor drugs such as omeprazole and esomeprazole (it is acceptable to change patient to H2 receptor blocking drugs prior to Day 1)
10. Concomitant use of known strong-to-moderate inducers or inhibitors of CYP3A within 3 days or 5 half-lives (whichever is longer) of Day 1
11. Use of CYP3A-sensitive substrate drugs with a narrow therapeutic index within 3 days or 5 half-lives (whichever is longer) of study drug dosing including, but not limited to, alfentanil, astemizole, cisapride, cyclosporine, dihydroergotamine, ergotamine, fentanyl, pimozide, quinidine, sirolimus, tacrolimus, or terfenadine
12. Planned or concomitant use of any anticoagulants and platelet aggregation inhibiting drugs such as aspirin, NSAIDs, thienopyridenes (within 14 days of planned dosing through end of follow-up)
13. Has received any investigational drug within the 30 days before receiving the first dose of study medication, or at least 5 times elimination half-life of the drug (whichever is longer); patient should not be using an investigational device at the time of dosing
14. Current drug or alcohol abuse
15. Refractory nausea and vomiting, malabsorption, external biliary shunt, or significant bowel resection that would preclude adequate study drug absorption
16. History of solid organ transplant
17. Positive for screening for HIV, hepatitis B (surface and core antibodies unrelated to vaccination), or hepatitis C (anti-HCV antibody confirmed with Hep C RNA)
18. History of serious infections requiring intravenous therapy within the last 3 months before Day 1
19. Clinically significant cognitive dysfunction (≥Grade 1) or medical history suggestive of increased risk for cognitive dysfunction during the study
20. Live vaccine within 28 days prior to Day 1 or plan to receive one during the study
21. Planned surgery in the time frame of the dosing period
22. Any other clinically significant disease, condition, or medical history that, in the opinion of the Investigator, would interfere with patient safety, study evaluations, and/or study procedures Additionally, participants must fulfill all entry criteria to be enrolled into the study. Participants who fail to meet the entry criteria may be rescreened once at the discretion of the Investigator after informing the study Medical Monitor.

Assessments:

After providing informed written consent, subjects typically complete the following clinical assessments: physical examination; medical history; concomitant medications; weight; height; vital signs; ITP-BAT bleeding scale; QOL assessment EQ-5D VAS; online cognitive testing; and safety assessments.

Subjects typically complete the following laboratory and ECG assessments as part of the study:
1. Urinalysis: pH, specific gravity, protein, glucose, ketones, bilirubin, blood, nitrites, urobilinogen and leukocytes measured by dip stick or local requirement
2. Hepatitis B and C, HIV
3. Pregnancy test for women of childbearing potential only. Serum pregnancy tests at screening, urine pregnancy tests at other visits
4. FSH: To confirm postmenopausal status for women who are not surgically sterile and of reproductive potential
5. ABO and Rh blood type
6. Immature Platelet Fraction and Mean Platelet Volume (where available at local lab)
7. Serum chemistry: Aspartate aminotransferase (AST), Alanine aminotransferase (ALT), Total, direct, and indirect bilirubin levels, Alkaline phosphatase (ALP), Albumin, Creatinine, Urea, Total Protein, Sodium, Chloride, Calcium, Phosphate, Potassium, Glucose (random), and creatine phosphokinase (CPK)
8. Hematology (CBC) including differential and reticulocyte counts
9. T/B/NK/monocyte counts by flow cytometry
10. PT/INR PTT
11. TPO levels
12. Hemolysis panel consisting of Coombs test, haptoglobin levels
13. Platelet autoantibody panel (Australia Only: test excluded)
14. PK sampling at various times
15. 12-lead ECG (single and triplicate)

Laboratory assessments may be performed at both central and local laboratories, if required.

Safety assessments include the following: the frequency, severity and relationship of AEs; clinical laboratory test changes; physical examination, ECGs, vital signs, and cognitive function.

In the dose escalation study, patients remain under observation in the clinic for 6 hours after administration of the first dose at the beginning of each new, higher dosing level while having intensive PK sampling performed.

Dosage Forms:

In the study, PRN1008 is administered in the form a film-coated tablet. PRN1008 tablets are packaged in white high-density polyethylene (HDPE) bottles with child-resistant induction-sealed caps; these bottles are intended to be stored at 2-8° C. and can be transported without ice at room temperature. Additionally, the bottles can be kept at room temperature conditions for up to 2 weeks.

Each PRN1008 film-coated tablet contains either 100 mg or 300 mg of PRN1008 drug substance. In addition, the tablet contains Microcrystalline Cellulose (filler), Crospovidone (disintegrant), Sodium Stearyl Fumarate (lubricant), and a non-functional film coating. A 100 mg tablet is a round shape and orange in color. A 300 mg tablet is an oval shape and white in color.

Based on previous studies, food does not appear to impact the extent of PRN1008 absorption but reduces the rate (longer average $T_{max}$ of ~2.5 hours). Accordingly, PRN1008 tablets should be taken with a glass (~8 oz) of water but may be taken with or without food, i.e., a period of fasting is not required.

Analysis Populations:

The Screening Population for this study includes all participants who provide informed consent and have screening assessments evaluated for study participation are included in the Screening Population.

The Safety Population includes all participants who have received at least one dose of PRN1008 will be included in the safety analysis. The Safety Population will be used for all safety analyses. For assessment of safety by the IDSM, with regard to dropping a dose level for futility, 3 evaluable patients, defined as compliance of ≥75% of doses for that dose level, are required. During the study, patients will be replaced if necessary, to fulfill this requirement.

The Intent-to-Treat Exposed (ITT-E) Population includes all participants who have received at least one dose of PRN1008.

The Pharmacokinetic Analysis Population includes all participants who have received at least one dose of PRN1008 and have at least one plasma concentration value will be included in the PK analysis. The Pharmacokinetic Analysis Population will be used for all PK analyses. Participants prematurely discontinued from the study, for reasons other than TEAEs, may be replaced at the discretion of the Sponsor to ensure adequate numbers of evaluable participants.

A patient who withdraws from the study before the planned end of study visit is considered to have withdrawn from the study early. Participants in this study have the right to withdraw at any time for any reason. Additionally, investigators may withdraw participants from the study in the event of intercurrent illness, AEs, treatment failure after a prescribed procedure, lack of compliance with the study and/or study procedures, or any other reasons where they feel it is in the best interest of the participant to be terminated from the study.

Safety and Toxicity Management:

An Independent Data Safety Monitor (IDSM) chosen from expert clinicians in the ITP field provides independent monitoring of the phase ½ study. A Safety Monitoring Committee (SMC), comprised of the IDSM as Chairperson, lead Investigator, Study Medical Monitor, and Sponsor's Medical Monitor, also closely supervises the conduct of the study, meeting approximately quarterly and recommending study modification or termination to the Sponsor, based on review of safety and efficacy information. SMC findings that impact the safety of patients in this study are reported to the local Competent Authority (CA) and IRB/EC.

The IDSM made "sentinel cohort" safety evaluations. The "sentinel patients" for each dose level had their data reviewed by the IDSM, in order to choose the starting dose for additional, new patients. After review, the IDSM could determine that a starting dose for new patients should be dropped for futility (lack of platelet response), increased to the next planned dosing level, kept the same, or reduced. New patients entering the study commenced at the dose level determined by the IDSM based on: (1) f≥⅔ or ≥⅖ of those sentinel patients have a DLT at any dose level, that level shall be determined the "Maximally Administered Dose" and starting doses (new patients) and continuing doses (patients already on study) set at lower dosing levels (or study suspended if the current sentinel dose cohort was 200 mg QD); (2) two or more sustained platelet responses (3 of 4 counts) in the sentinel patients are seen at the current starting dose level the starting dose will not be escalated.

Clinical Adverse Events

The AE Collection Period begins at the time of the first screening/eligibility assessment and ends at the end of the study for each patient. An AE is any untoward medical occurrence in a participant or clinical investigation participant administered a pharmaceutical product and which does not necessarily have to have a causal relationship with the intervention. An AE can therefore be any unfavorable and unintended sign (including an abnormal laboratory finding, for example), symptom, or disease temporally associated with the use of an investigational product, whether or not considered related to the product. Investigators are instructed to record all AEs encountered during the clinical study in detail from the date of participant consent throughout the study follow-up period. Pre-existing conditions that worsen during a study are reported as AEs.

Adverse Event Relationship to Study Drug

Investigators are instructed to use their knowledge of the study participant, the circumstances surrounding the event, and an evaluation of any potential alternative causes to determine whether an AE may be considered as related to the study drug, indicating "yes" or "no" accordingly. Investigators are asked to consider following information in assessing relatedness: (1) temporal relationship of event onset to the initiation of study drug; (2) course of the event, considering especially the effects of dose reduction, discontinuation of study drug, or reintroduction of study drug (if applicable); (3) known association of the event with the study drug or with similar treatments; (4) known association of the event with the disease under study; (5) presence of risk factors in the study participant or use of concomitant medications known to increase the occurrence of the events; and (6) presence of non-treatment-related factors that are known to be associated with the occurrence of the event.

Investigators are instructed to follow up AEs, especially those for which the severity is Grade 3 or higher, until stabilization or until 4 weeks post last dose (considered as the last follow up), based on the PK profile of the drug.

Laboratory and ECG Abnormalities

Investigators are instructed to record any treatment-emergent abnormal laboratory or ECG result that is clinically significant, i.e., meeting one or more of the following conditions, as a single diagnosis on the AE page in the CRF. As non-limiting examples, laboratory and ECG abnormalities accompanied by clinical symptoms, leading to a change in study drug (e.g., dose modification, interruption or permanent discontinuation), or requiring a change in concomitant therapy (e.g., addition of, interruption of, discontinuation of, or any other change in a concomitant medication, therapy or treatment) should be recorded as an AE, with any laboratory or ECG result abnormality fulfilling the criteria for a serious adverse event (SAE) reported as such, in addition to being recorded as an AE.

Adverse Event Intensity Grading

Investigators are instructed to report all clinical AEs encountered during the study. The intensity of AEs is graded based on the NCI CTCAE, Version 4.0 or higher. For any AEs not found in the CTCAE, a description of intensity grading can be found below:

Grade 1: Mild; asymptomatic or mild symptoms; clinical or diagnostic observations only; intervention not indicated.

Grade 2: Moderate; minimal, local or noninvasive intervention indicated; limiting age-appropriate instrumental activities of daily living.

Grade 3: Severe or medically significant but not immediately life-threatening; hospitalization or prolongation of hospitalization indicated; disabling; limiting self-care activities of daily living.

A serious adverse event (SAE) is any experience (clinical AE or abnormal laboratory test) that suggests a significant hazard, contraindication, side effect, or precaution. An SAE must fulfill at least one of the following criteria at any dose level: is fatal (results in the outcome death); is life-threatening; requires in-patient hospitalization or prolongation of existing hospitalization; results in persistent or significant disability/incapacity; is a congenital anomaly/birth defect; or is medically significant or requires intervention to prevent one or other of the outcomes listed above. Investigators are instructed to report life-threatening events or any event with an outcome of death should be reported as an SAE.

Pregnancy

Any female clinical trial participant who becomes pregnant during the study must be instructed to stop taking the study drug and immediately inform the Investigator. Pregnancies occurring up to 90 days after the completion of the study drug must also be reported to the Investigator.

Ethical Considerations:

Investigators are tasked with ensuring that the study is conducted in full conformance with the principles of the "Declaration of Helsinki" or with the laws and regulations of the country in which the research is conducted, whichever affords the greater protection to the individual. Additionally, the study adheres to the principles outlined in current "Guideline for Good Clinical Practice" ICH Tripartite Guideline or with local law if it affords greater protection to the participant.

Signed and dated informed consent is obtained from each participant prior to participating in the study after adequate explanation of the aims, methods, objectives and potential hazards of the study. The Investigator or designee must explain that the participants are completely free to refuse to enter the study or to withdraw from it at any time, for any reason.

Physical Examination Procedures:

At screening and follow-up visits in the study, a complete physical examination consists of checking the normality or abnormality of the following body systems: general appearance, skin, eyes, ears, nose, throat, heart, chest/breast, abdomen, neurological system, lymph nodes, spine and extremities (skeletal) and the conduct of and online cognitive testing of learning and memory. An abbreviated physical examination consists of checking the normality or abnormality of the following body systems: general appearance, skin, abdomen, and cardiorespiratory examination. Height is recorded at screening only. Blood pressure (BP), pulse rate, body temperature and respiratory rate are recorded at specific time points.

Single 12-lead ECG assessments are also obtained at specific time points to confirm eligibility and to ensure real time safety evaluation of the participants in the study. For ECG evaluations, participants should be in a resting position for at least 10 minutes prior to any measurement. Body position should also be consistently maintained for each ECG evaluation. In particular, changes in heart rate should be avoided. There should be no environmental distractions (TV, radio, conversation) during the pre-ECG rest and the ECG recording time.

Heart rate (HR), QRS duration and respiratory rate (RR), and QT intervals are recorded. Changes of the T-wave and U-wave morphology and overall ECG interpretation are documented. All ECG recordings are performed using a standard high-quality, high-fidelity digital electrocardiograph machine equipped with computer-based interval measurements. For triplicate ECG assessments, at least three interpretable ECG recordings (without artifacts) are collected per time point within a ±10 minute period per time point.

Laboratory Test Procedures:

Laboratory assessments are performed at a central laboratory, with the provision for occasional local laboratory testing, if required. Laboratory safety tests are collected at specific time points. Additional blood or urine samples may be taken at an investigator's discretion if the results of any test fall outside the reference ranges, or clinical symptoms necessitate additional testing to monitor participant safety. Where the clinical significance of abnormal lab results is considered uncertain, screening lab tests may be repeated before Day 1 to confirm eligibility. In the event of unexplained abnormal clinically significant laboratory test values, the tests should be repeated immediately and followed up until they have returned to the normal range, are considered to be clinically stable, and/or an adequate explanation of the abnormality is found.

Figure 5:
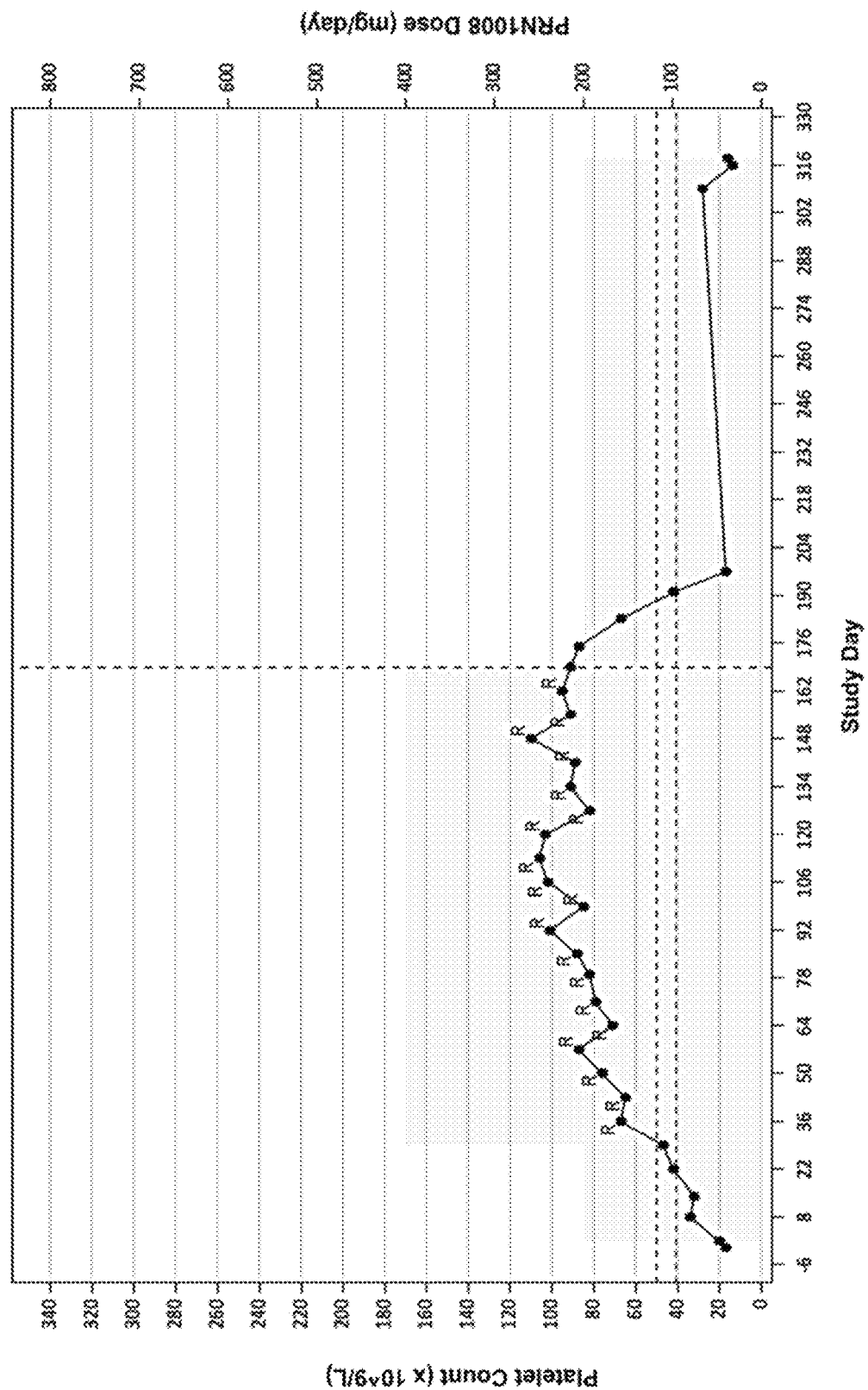
FIG. 5 depicts the platelet count response over time for a patient with secondary ITP enrolled in a phase ½ study investigating PRN1008 in ITP patients.

Preliminary Results:

Positive preliminary data has been observed in the ongoing phase ½ trial of PRN1008 in the treatment of ITP. Illustratively, FIG. 5 shows platelet count response for an enrolled patient with secondary ITP, demonstrating responsiveness to treatment at 400 mg qd. During the completed dose-escalation study, PRN1008 was well-tolerated across all doses (200 and 400 mg qd, 300 and 400 mg bid) in a highly treatment-resistant and refractory patient population with immune thrombocytopenia (ITP). All TEAEs were mild to moderate with no thrombotic events.

Early study data was reported in October 2019. At the time of reporting, the phase ½ trial of PRN1008 had enrolled 26 adult patients who have had two platelet counts<30,000/µL within 15 days prior to treatment. Oral PRN1008 starting doses were 200 mg qd, 400 mg qd, 300 mg bid, and 400 mg bid, with intra-patient dose escalation allowed every four weeks, with the trial having a median treatment duration of 12.7 weeks (range: 0.14 to 39.71) at reporting. In the early study data reported in October 2019, 39 percent (80% confidence interval (CI) 27.3, 51.0) of the 26 patients that had enrolled up to that point achieved the trial's primary endpoint of ≥2 consecutive platelet counts of ≥50,000/µL, separated by at least five days, and increased by ≥20,000/µL from baseline without requiring rescue medication (Tables 2 and 3). In addition, 46 percent (80% CI 34.2, 58.5) of enrolled patients achieved any 2 platelet counts≥50,000/µL (Table 3). These results were observed despite the limited duration of therapy and patients at multiple escalating dose levels. In the preliminary data on 15 patients across all doses who had completed at least 12 weeks of therapy, the response rate was greater than 50 percent for both endpoints. PRN1008 was well-tolerated at all doses studied, whether given as a monotherapy or with allowed concomitant ITP therapy, with no reported treatment related bleeding or thrombotic events, at the time of early reporting.

In Table 2, percentages are based on the number of patients in each dose group and overall. Patients are classified into different dose levels according to the dose they received prior to the start of the platelet response. The 95% confidence interval is based on the Wilson Score method.

TABLE 2

Preliminary Efficacy Data (ITT-E Population, Oct. 2019 Reporting)

|  | 200 mg QD (N = 9) | 400 mg QD (N = 8) | 300 mg BID (N = 12) | 400 mg BID (N = 19) | Overall (N = 26) |
| --- | --- | --- | --- | --- | --- |
| Responder | 1 (11.1) | 2 (25.0) | 4 (33.3) | 6 (31.6) | 10 (38.5) |
| 95% CI | 1.99, 43.5 | 7.15, 59.1 | 13.8, 60.9 | 15.4, 54.0 | 22.4, 54.5 |
| Non-Responder | 8 (88.9) | 6 (75.0) | 8 (66.7) | 13 (68.4) | 16 (61.5) |

TABLE 3

Preliminary Efficacy Data (ITT-E Population, Oct. 2019 Reporting)

| | Platelet counts ≥50 × 10⁹/L 80% (CI) | | | | |
|---|---|---|---|---|---|
| Treatment duration and dose | Primary Endpoint: 2 consecutive | Any 2 | 50% of all | 4 out of final 8 | 4 out of final 6 |
| All patients enrolled (N = 26) | 38.5 (27.3-51) | 46.2 (34.2-8.5) | 26.9 (17.4-39.2) | 19.2 (11.3-30.8) | 19.2 (11.3-30.8) |
| ≥4 weeks, all doses (N = 20) | 45 (31.7-59.1) | 55 (40.9-68.3) | 25 (14.8-39) | 25 (14.8-39) | 25 (14.8-39) |
| ≥12 weeks, all doses (N = 15) | 53.3 (37.3-68.7) | 66.7 (50.1-79.9) | 26.7 (14.9-43.1) | 33.3 (20.1-49.9) | 33.3 (20.1-49.9) |
| ≥12 weeks, 300 mg BID & 400 mg BID (N = 11) | 63.6 (44.4-79.3) | 72.7 (53.5-86.1) | 27.3 (13.9-46.5) | 36.4 (20.7-55.6) | 36.4 (20.7-55.6) |

As of Nov. 13, 2019, the 31 enrolled patients in the phase ½ study were characterized by the demographic information provided in Tables 4 and 5. The median age of enrolled patients was 50, with 29 of 31 classified with primary ITP (94%) and 2 of 31 classified with secondary ITP (6%). At enrollment, patients had ITP for a median duration of 7.8 years, were heavily pretreated (median of 6 prior therapies), and 26% had undergone a prior splenectomy. During the study, 10 patients (32%) received PRN1008 monotherapy and 21 patients (68%) were on ≥1 concomitant ITP medication.

TABLE 4

Patient Demographics (Data Cut-off: Nov. 13, 2019)

| Demographics | N = 31 |
|---|---|
| Median age, y (range) | 50 (21-74) |
| Female, n (%) | 18 (58) |
| ITP classification, n (%) | |
| Primary ITP | 29 (94) |
| Secondary ITP | 2 (6) |
| Median duration of ITP, y (range) | 7.8 (0.5-42.4) |
| Median baseline platelet count, ×10⁹/L (range) | 13 (3-28) |

TABLE 5

Prior ITP Therapy (Data Cut-off: Nov. 13, 2019)

| Prior ITP Therapy | N = 31 |
|---|---|
| Median number of prior ITP therapies (range) | 6 (1-41) |
| Splenectomy, n (%) | 8 (26) |
| Prior ITP therapies, n (%) | |
| Corticosteroids | 26 (84) |
| TPO-RA | 17 (55) |
| IVIG/Anti-D | 11 (35) |
| Rituximab | 10 (32) |

As of Nov. 13, 2019, study data confirmed that the optimal safety and efficacy dose for PRN1008 in the treatment of ITP is 400 mg bid.

The primary endpoint defined as 2 consecutive platelet counts≥50,000 µL without requiring rescue medication, was met in 39% of all patients independent of dose or time on treatment. This patient population was highly treatment-resistant and refractory, with patients characterized by a median of 6 prior therapies, including 55% receiving a prior TPO-RA. Rapid onset (platelet counts>30 k by the first week of treatment) was observed following the start of PRN1008 treatment, and responses were durable in the majority of patients. Platelet response was further improved with longer treatment and at higher doses of PRN1008.

Figure 6:
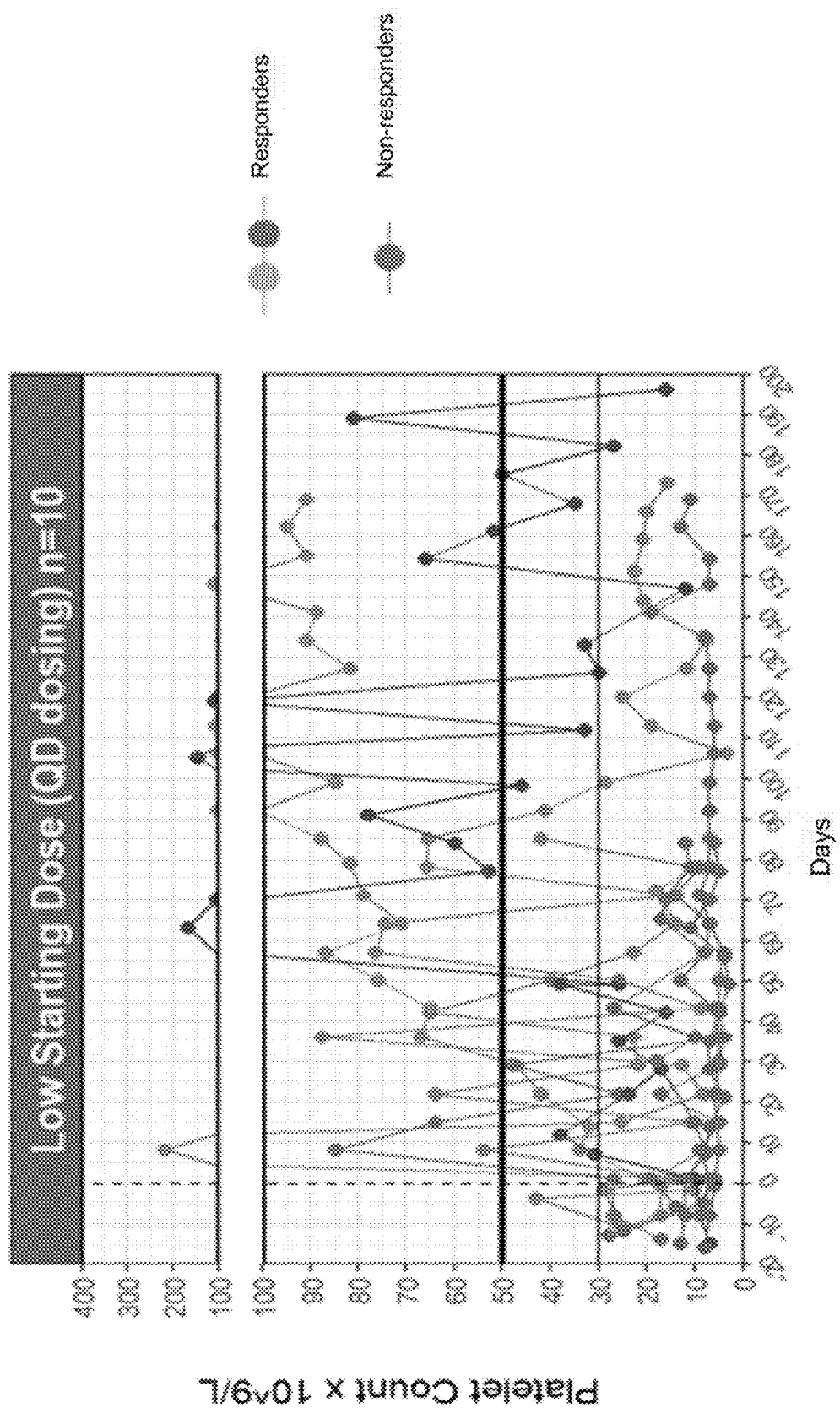
FIG. 6 depicts the platelet count response over time for phase ½ ITP dose-finding study patients who started on a low starting dose of PRN1008 (QD dosing) (n=10) (data cut-off: Nov. 13, 2019).
Figure 7:
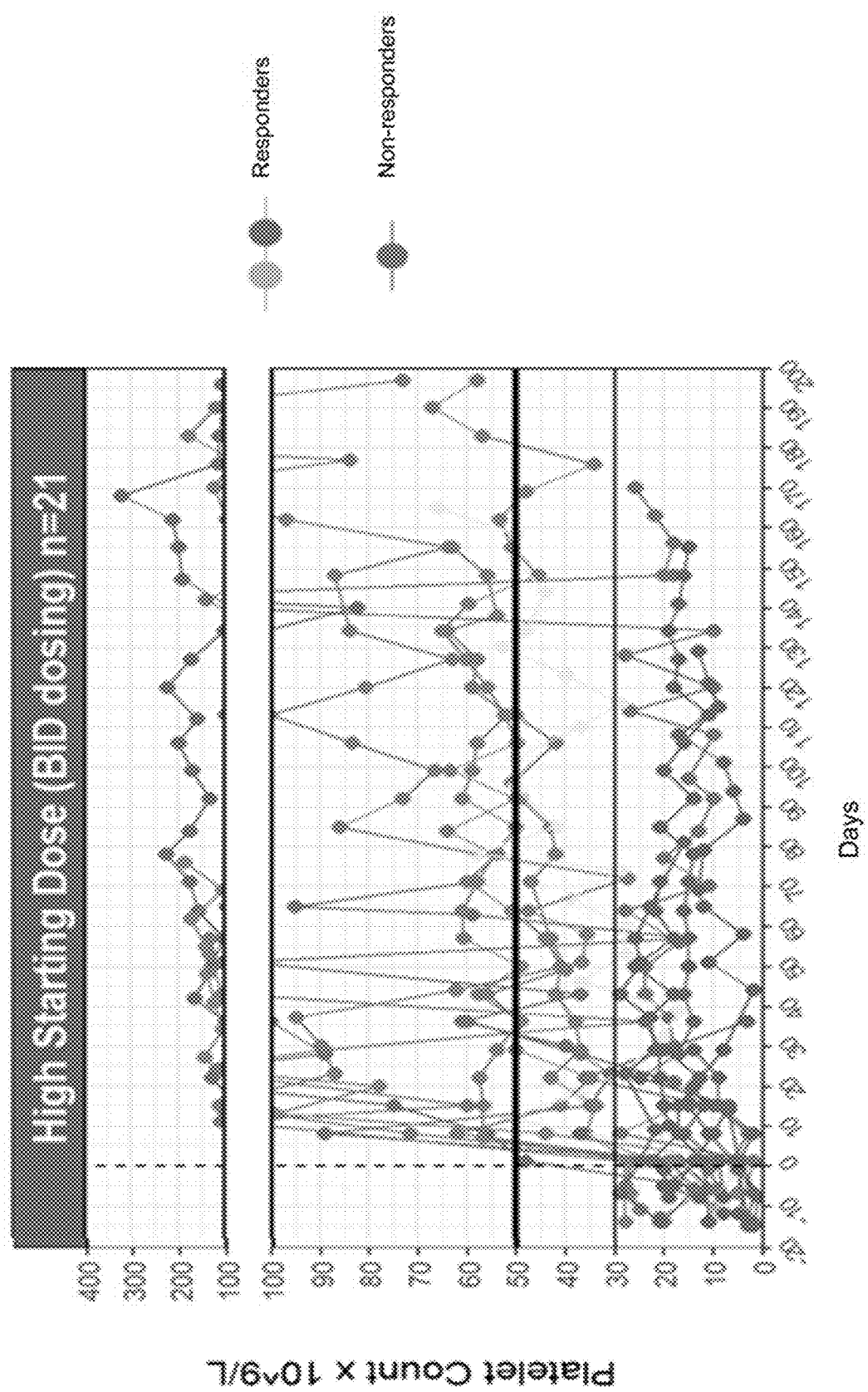
FIG. 7 depicts the platelet count response over time for phase ½ ITP dose-finding study patients who started on a high starting dose of PRN1008 (BID dosing) (n=21) (data cut-off: Nov. 13, 2019).

Table 6 provides a summary of platelet response by treatment duration and dose (data cut-off: Nov. 13, 2019). Individual platelet counts of dose levels over time for low starting dose (qd dosing, n=10) and high starting dose (bid dosing) (n=21) are depicted in FIGS. 6 and 7, respectively (data cut-off: Nov. 13, 2019). In FIGS. 6 and 7, responders are people who achieved ≥50,000/µL platelet counts at least one.

Figure 8:
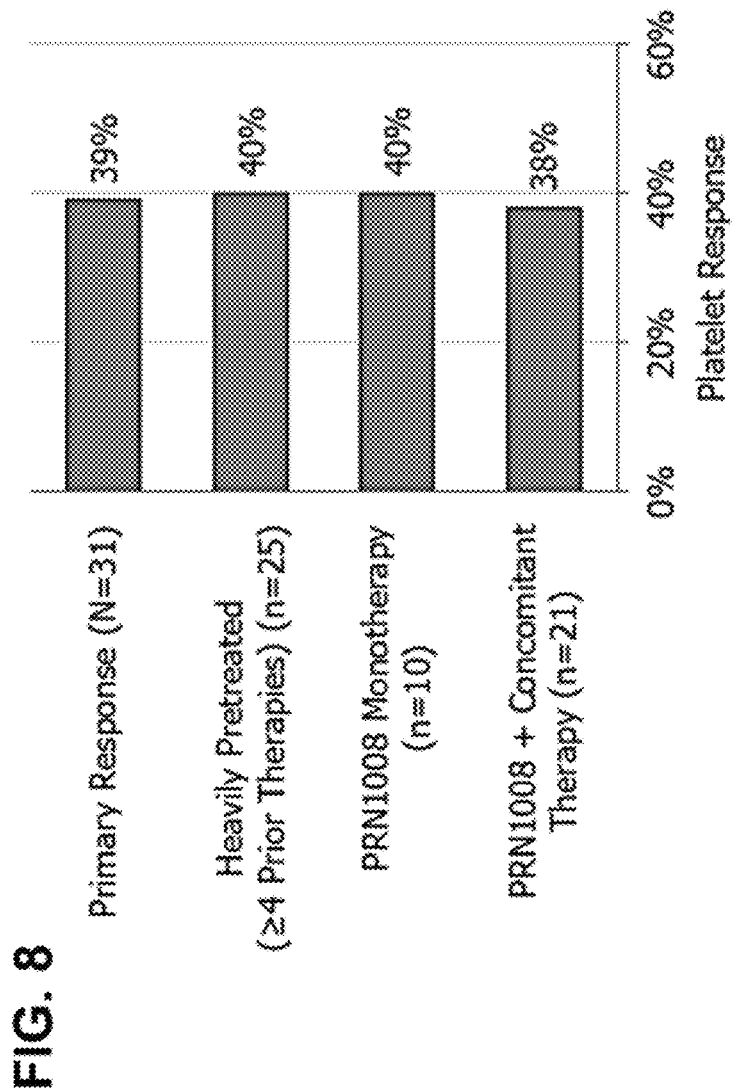
FIG. 8 depicts summary statistics for platelet response in phase ½ ITP patients (data cut-off: Nov. 13, 2019).

Subset analyses of primary platelet responses are depicted in FIG. 8 (data cut-off: Nov. 13, 2019). As of Nov. 13, 2019, 10 of 25 (40%) of heavily pretreated (≥4 prior therapies) patients were responding to PRN1008 treatment. Similar responses were achieved in patients receiving PRN1008 monotherapy (4 of 10 patients) and concomitant therapy (8 of 21 patients).

TABLE 6

Summary of Platelet Response by Treatment Duration and Dose (Data Cut-off: Nov. 13, 2019)

| | Patients Achieving Platelet Counts ≥50 × 10⁹/L (80% CI) | | |
|---|---|---|---|
| Treatment Duration and Dose | Primary Endpoint 2 consecutive | Any 2 | 4 of Final 8 |
| All patients enrolled (N = 31) | 39% (28%-50%) | 45% (34%-57%) | 29% (20%-40%) |
| ≥4 weeks, all doses (n = 26) | 46% (34%-59%) | 54% (41%-66%) | 35% (24%-47%) |
| ≥12 weeks, all doses (n = 17) | 47% (33%-62%) | 59% (43%-73%) | 35% (22%-51%) |
| ≥12 weeks at 300 and 400 mg bid (n = 13) | 54% (37%-70%) | 62% (44%-77%) | 39% (23%-56%) |

PRN1008 was well-tolerated in ITP patients across all doses as of Nov. 13, 2019 (Table 7). The median treatment duration at the Nov. 13, 2019, cut-off was 12.0 weeks (range: 0.1-41.9). Related TEAEs were reported in 11 patients (35%), with all reported TEAEs being grade 1 or 2 (mild to moderate). No treatment-related bleeding or thrombotic events were reported, nor were significant changes in the ITP-BAT bleeding scale from baseline to last visit. No dose-limiting toxicities were observed by data cut-off. The observed safety profile was consistent with the safety observed in pemphigus studies (Murrell D. et al., AAD 2018).

As of Apr. 22, 2020, 47 patients had enrolled in the study, with 32 patients initiated on a 400 mg bid dose. Demographic information for enrolled patients as of Apr. 22, 2020, is included in Table 8. ITP patient characteristics were similar across all treatment groups in a difficult-to-treat population. Similar to the Nov. 13, 2019, cut-off data, patients had ITP for a median of 7+ years at enrollment, were heavily pretreated (median of 6 prior medications), and 28% had undergone a prior splenectomy. Additionally, 31 patients (66%) were on ≥1 concomitant ITP medication (CS and/or TPO) and were considered inadequate responders.

TABLE 7

Summary of Related TEAEs (Data Cut-off: Nov. 13, 2019)

| Related TEAEs (≥2 Patients), n (%) | Grade 1/2 |
|---|---|
| All TEAEs | 11 (35) |
| Nausea | 8 (26) |
| Diarrhea | 7 (23) |
| Abdominal distension | 3 (10) |
| Fatigue | 3 (10) |

TABLE 8

Patient Demographics and Prior ITP Therapy (Data Cut-off: Apr. 22, 2020)

| | All Patients (N = 47) | 400 mg bid (n = 32) |
|---|---|---|
| Median age, y (range) | 50 (21-74) | 50 (21-74) |
| Female, n (%) | 27 (57) | 20 (63) |
| ITP classification, n (%) | | |
| Primary ITP | 44 (94) | 31 (97) |
| Secondary ITP | 3 (6) | 1 (3) |
| Median duration of ITP, y (range) | 7.8 (0.4-52.5) | 7.3 (0.4-52.5) |
| Median baseline platelet count, ×10⁹/L (range) | 14 (3-33) | 13 (4-33) |
| Median number of prior ITP therapies (range) | 6 (1-54) | 6 (1-54) |
| Splenectomy, n (%) | 13 (28) | 9 (28) |
| At least one prior ITP therapy | 100% | 100% |

Figure 9:
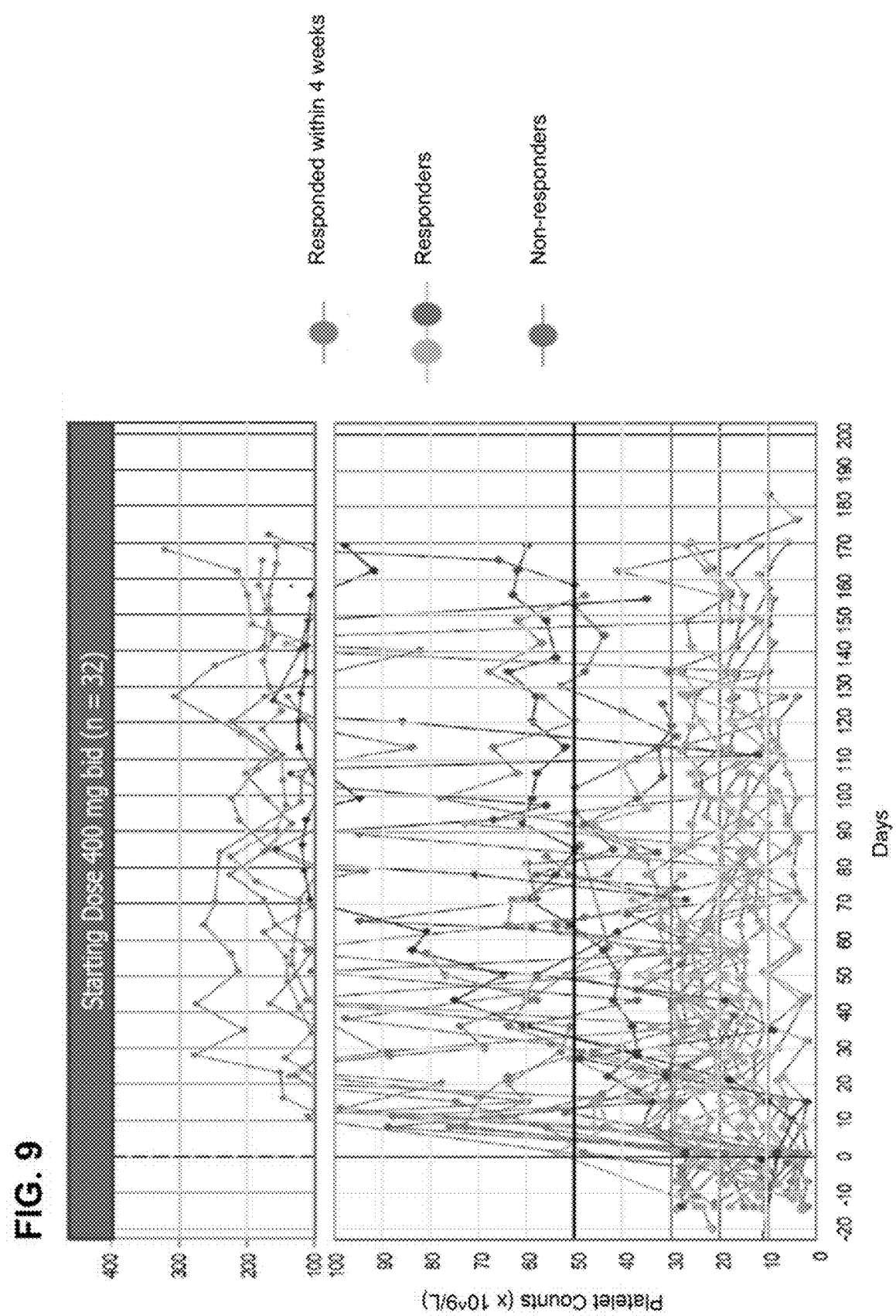
FIG. 9 depicts the platelet count response over time for phase ½ ITP patients who started on 400 mg PRN1008 bid (n=32) (data cut-off: Apr. 22, 2020).

As of Apr. 22, 2020, platelet responses had a fast onset and were maintained in the majority of patients who started on the PRN1008 400 mg bid dose (FIG. 9). By day 8 (the first platelet count taken after the start of treatment), platelets≥30×10$^9$/L (a clinically significant platelet count) were observed in 53% of patients initiated at 400 mg bid and 79% of primary endpoint responders, where the primary endpoint was defined as 2 consecutive platelet counts 50,000/ μL≥without requiring rescue medication. By week 4, 57% of responders achieved the primary endpoint. In addition, 50% of patients achieved the primary endpoint response when initiated on PRN1008 400 mg bid and treated for 12 weeks or more. Moreover, the response was durable, with responders maintaining platelet counts: 71% of time (weeks) at ≥50×10$^9$/L; and 88% of time (week) at ≥20×10$^9$/L above baseline.

Figure 10:
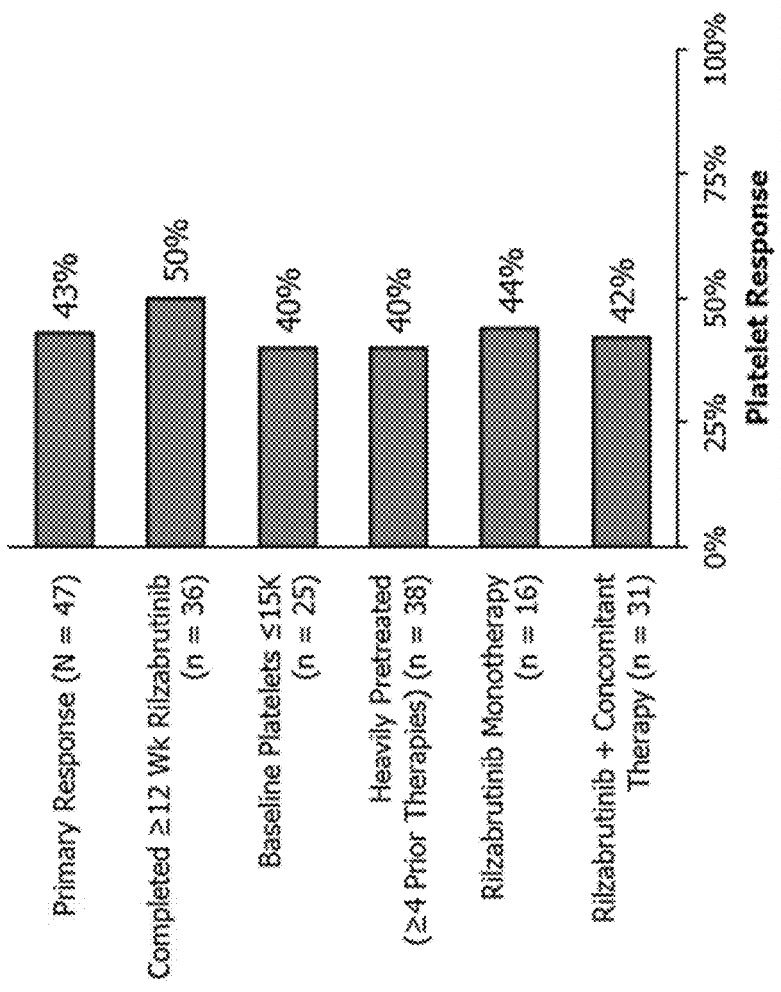
FIG. 10 depicts summary statistics for platelet response in phase ½ ITP patients (data cut-off: Apr. 22, 2020).

Subset analyses of platelet responses are depicted in FIG. 10 (data cut-off: Apr. 22, 2020). Overall, 43% of patients met the primary endpoint, which increased with ≥12 weeks of PRN1008. As of Apr. 22, 2020, 15 of 38 (40%) of heavily pretreated (≥4 prior therapies) patients were responding to PRN1008 treatment. Similar responses were achieved in patients receiving PRN1008 monotherapy (7 of 16 patients) and inadequate responders on concomitant therapy (13 of 31 patients).

PRN1008 was well-tolerated in ITP patients across all doses as of Apr. 22, 2020 (Table 9). The median treatment duration at the Apr. 22, 2020, data cut-off was 17.7 weeks for all patients (range: 0.6-41.9) and 18 weeks for patients initiated on 400 mg bid (range: 1.4-24.6). Related TEAEs were reported in 21 patients (45%), with all reported TEAEs being transient and grade 1 or 2 (mild to moderate). No related serious adverse events were reported. Additionally, no treatment-related bleeding or thrombotic events were reported, nor were significant changes in the ITP-BAT bleeding scale from baseline to last visit. The observed safety profile was consistent with the safety observed in pemphigus studies (Murrell D. et al., AAD 2018).

TABLE 9

Summary of Related TEAEs (Data Cut-off: Apr. 22, 2020)

| Related TEAEs | All Patients (N = 47) | | 400 mg bid (n = 32) | |
|---|---|---|---|---|
| (≥10%), n (%) | Grade 1 | Grade 2 | Grade 1 | Grade 2 |
| All related TEAEs | 10 (21) | 11 (23) | 15 (47) | 11 (34) |
| Diarrhea | 14 (30) | 2 (4) | 11 (34) | 2 (6) |
| Nausea | 12 (26) | 1 (2) | 8 (25) | 1 (3) |
| Fatigue | 5 (11) | 1 (2) | 3 (9) | 1 (3) |

As of May 5, 2020, oral PRN1008 achieved primary endpoint in 50% of patients treated for ≥12 weeks (n=26) and demonstrated fast onset and durable responses. PRN1008 treatment for ≥12 weeks further improved platelet responses. Similar to the Nov. 13, 2019, cut-off data, the primary endpoint was defined as 2 consecutive platelet counts≥50,000 μL without requiring rescue medication. Table 10 provides a summary of platelet response by treatment duration and dose (data cut-off: May 5, 2020).

TABLE 10

Summary of Platelet Response by Treatment Duration and Dose (Data Cut-off: May 5, 2020)

| Treatment Duration and Dose | Patients Achieving Platelet Counts ≥50 × 10$^9$/L (80% CI) | | |
|---|---|---|---|
| | Primary Endpoint 2 consecutive | 50% of Counts | 4 of Final 6 |
| All patients enrolled (N = 47) | 43% (34, 52) | 34% (26, 43) | 28% (20, 37) |
| ≥12 week treatment, all doses (n = 36), includes patients escalated to 400 mg bid | 50% (40, 60) | 39% (29, 50) | 33% (24, 44) |
| Initiated 400 mg bid (n = 32) | 44% (33, 55) | 38% (27, 49) | 31% (22, 42) |
| ≥12 week treatment (initial 400 mg bid) (n = 26) | 50% (38, 62) | 42% (31, 55) | 35% (24, 47) |

REFERENCES

Certain documents are referred to in this Application in short citation format. More detailed citations for some of the referenced documents are provided below.

Bussel J B, Cheng G, Saleh M N, Psaila B, Kovaleva L, et al. Eltrombopag for the treatment of chronic idiopathic thrombocytopenic purpura. N Engl J Med, 357:2237-47, 2007.

Cataland S R, Scully M A, Paskavitz J, Maruff P, Witkoff L, Jin M, Wu, H M. Evidence of persistent neurologic injury following thrombotic thrombocytopenic purpura. American Journal of Hematology. 2011; 86(1): 87-89.

Drug Development and Drug Interactions: Table of Substrates, Inhibitors and Inducers. U.S. Food and Drug Administration. https://www.fda.gov/Drugs/DevelopmentApprovalProcess/DevelopmentResources/DrugInteractionsLabeling/ucm093664.htm Montillo M, O'Brien S O, Tedeschi A, Byrd J C, Dearden C, et al. Ibrutinib in previously treated chronic lymphocytic leukemia patients with autoimmune cytopenias in the RESONATE study. Blood Cancer Journal 7, e524, (Letter to the editor) 2017.

Murrell D F, Stavropoulos P., Patsatsi A et al. Final results of the Believe-PV proof of concept study of PRN1008 in pemphigus. The 77$^{th}$ Annual Meeting of the American Academy of Dermatology; 2019 Mar. 1-5; Washington, DC: AAD; 2019. Session 5034: Late-breaking research-clinical trials.

Podolanczuk A, Lazarus A H, Crow A R, Grossbard E, Bussel J B. Of mice and men: an open-label pilot study for treatment of immune thrombocytopenic purpura by an inhibitor of Syk. Blood 2009; 113:3154-3160.

PRN1008 Investigator Brochure, Principia Biopharma.

Rodeghiero F, Michel M, Gernsheimer T, Ruggeri M, Blanchette V, et. al. Standardization of bleeding assessment in immune thrombocytopenia: report from the International Working Group. Blood 2013 121: 2596-2606.

Rogers K A, Ruppert A S, Bingman A, Andritsos L A, Awan F T, Blum K A, Flynn J M, Jaglowski S. Incidence and description of autoimmune cytopenias during treatment with ibrutinib for chronic lymphocytic leukemia. Leukemia 2016; 30:346-350.

Byrd J C, Furman R R, Coutre S E, Flinn I W, Burger J A, Blum K A, Grant B, Sharman J P, Coleman M, Wierda W G, Jones J A, Zhao W, Heerema N A, Johnson A J, Sukbuntherng J, Chang B Y, Clow F, Hedrick E, Buggy J J, James D F, O'Brien S. Targeting BTK with Ibrutinib in Relapsed Chronic Lymphocytic Leukemia. N Engl J Med., 369(1):32-42, 2013.

Evans E K, Tester R, Aslanian S, Karp R, Sheets M, Labenski M T, Witowski S R, Lounsbury H, Chaturvedi P, Mazdiyasni H, Zhu Z, Nacht M, Freed M I, Petter R C, Dubrovskiy A, Singh J, Westlin W F. Inhibition of Btk with CC-292 Provides Early Pharmacodynamic Assessment of Activity in Mice and Humans. J Pharmacol Exp Ther, 346(2):219-28, 2013.

Imbruvica [package insert]. Pharmacyclics, Inc., Sunnyvale, CA; 2015.

Mohamed A J, Yu L, Backesjo C M, Vargas L, Faryal R, et al. Bruton's tyrosine kinase (Btk): function, regulation, and transformation with special emphasis on the PH domain. Immunol Rev 228, 58-73, 2009.

Sideras P and Smith C I. Molecular and cellular aspects of X-linked agammaglobulinemia. Adv Immunol, 59: 135-223, 1995.

Tsukada, S., Saffran, D. C., Rawlings, D. J., Parolini, O., Allen, R. C., Klisak, I., Sparkes, R. S., Kubagawa, H., Mohandas, T., Quan, S., and et al. Deficient expression of a B cell cytoplasmic tyrosine kinase in human X-linked agammaglobulinemia. Cell, 72: 279-290, 1993.

Vetrie, D., Vorechovsky, I., Sideras, P., Holland, J., Davies, A., Flinter, F., Hammarstrom, L., Kinnon, C., Levinsky, R., Bobrow, M., and et al. The gene involved in X-linked agammaglobulinaemia is a member of the src family of protein-tyrosine kinases. Nature, 361: 226-233, 1993.

Wang M L, Rule S, Martin P, Goy A, Auer R, Kahl B S, Jurczak W, Advani R H, Romaguera J E, Williams M E, Barrientos J C, Chmielowska E, Radford J, Stilgenbauer S, Dreyling M, Jedrzejczak W W, Johnson P, Spurgeon S E, Li L, Zhang L, Newberry K, Ou Z, Cheng N, Fang B, McGreivy J, Clow F, Buggy J J, Chang B Y, Beaupre D M, Kunkel L A, Blum K A. Targeting BTK with Ibrutinib in Relapsed or Refractory Mantle-Cell Lymphoma. N Engl J Med. 2013 Jun. 19. [Epub ahead of print].

RITUXAN (rituximab) Highlights of Prescribing Information. 2018. at https://www.accessdata.fda.gov/drugsatfda_docs/label/2018/103705s5450lbl.pdf.)

Crofford L J, Nyhoff L E, Sheehan J H, Kendall P L. The role of Bruton's tyrosine kinase in autoimmunity and implications for therapy. Expert Rev Clin Immunol 2016; 12:763-73.

Pal Singh S, Dammeijer F, Hendriks R W. Role of Bruton's tyrosine kinase in B cells and malignancies. Mol Cancer 2018; 17:57.

Volmering S, Block H, Boras M, Lowell C A, Zarbock A. The Neutrophil Btk Signalosome Regulates Integrin Activation during Sterile Inflammation. Immunity 2016; 44:73-87.

Montalban X, Arnold D L, Weber M S, et al. Placebo-Controlled Trial of an Oral BTK Inhibitor in Multiple Sclerosis. N Engl J Med 2019; 380:2406-17.

Norman P. Investigational Bruton's tyrosine kinase inhibitors for the treatment of rheumatoid arthritis. Expert Opin Investig Drugs 2016; 25:891-9.

Tam C S, LeBlond V, Novotny W, et al. A head-to-head Phase III study comparing zanubrutinib versus ibrutinib in patients with Waldenstrom macroglobulinemia. Future Oncol 2018; 14:2229-37.

Crawford J J, Johnson A R, Misner D L, et al. Discovery of GDC-0853: A Potent, Selective, and Noncovalent Bruton's Tyrosine Kinase Inhibitor in Early Clinical Development. J Med Chem 2018; 61:2227-45.

Min T K, Saini S S. Emerging Therapies in Chronic Spontaneous Urticaria. Allergy Asthma Immunol Res 2019; 11:470-81.

Gillooly K M, Pulicicchio C, Pattoli M A, et al. Bruton's tyrosine kinase inhibitor BMS-986142 in experimental models of rheumatoid arthritis enhances efficacy of agents representing clinical standard-of-care. PLoS One 2017; 12: e0181782.

Nadeem A, Ahmad S F, Al-Harbi N O, et al. Inhibition of Bruton's tyrosine kinase and IL-2 inducible T-cell kinase suppresses both neutrophilic and eosinophilic airway inflammation in a cockroach allergen extract-induced mixed granulocytic mouse model of asthma using preventative and therapeutic strategy. Pharmacol Res 2019; 148:104441

Drug Record Kinase Inhibitors. In: Services NIoHUSDoHH, ed.2019.

Khan Y, O'Brien S. Acalabrutinib and its use in treatment of chronic lymphocytic leukemia. Future Oncol 2019; 15:579-89.

Paydas S. Management of adverse effects/toxicity of ibrutinib. Crit Rev Oncol Hematol 2019; 136:56-63.

IMBRUVICA (ibrutinib) Highlights of Prescribing Information. US Food and Drug Administration, 2013. at https://www.accessdata.fda.gov/drugsatfda_docs/label/2015/205552s002lbl.pdf.)

Rigg R A, Aslan J E, Healy L D, et al. Oral administration of Bruton's tyrosine kinase inhibitors impairs GPVI-mediated platelet function. Am J Physiol Cell Physiol 2016; 310: C373-80.

Tang C P S, McMullen J, Tam C. Cardiac side effects of bruton tyrosine kinase (BTK) inhibitors. Leuk Lymphoma 2018; 59:1554-64.

Smith P F, Krishnarajah J, Nunn P A, et al. A phase I trial of PRN1008, a novel reversible covalent inhibitor of Bruton's tyrosine kinase, in healthy volunteers. Br J Clin Pharmacol 2017; 83:2367-76.

Hill R B J, Bisconte A, Tam D, Owens T, Brameld K, et al. Preclinical Characterization of PRN1008, a Novel Reversible Covalent Inhibitor of BTK that Shows Efficacy in a RAT Model of Collagen-Induced Arthritis. EULAR. Rome 2015.

Serafimova I M, Pufall M A, Krishnan S, et al. Reversible targeting of noncatalytic cysteines with chemically tuned electrophiles. Nat Chem Biol 2012; 8:471-6.

Claims or descriptions that include "or" or "and/or" between at least one members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all the group members are present in, employed in, or otherwise relevant to a given product or process.

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

The foregoing disclosure has been described in some detail by way of illustration and example, for purposes of clarity and understanding. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

What is claimed is:

1. A method for achieving a platelet count of at least 50,000/μL in a human patient with immune thrombocytopenia (ITP) in need thereof comprising administering to the human patient a therapeutically effective amount of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof, once a day or twice a day for a treatment period, wherein the human patient has been identified as having a platelet count of less than 30,000/μL for two or more consecutive platelet counts prior to the start of the treatment period, wherein two of the two or more platelet counts were measured no sooner than 7 days apart in the 15 days prior to the start of the treatment period, and wherein the human patient has been identified as having at least one characteristic chosen from:

a history of taking at least one prior ITP therapy prior to the start of the treatment period; and splenectomy prior to the start of the treatment period.

2. The method of claim 1, wherein achieving a platelet count comprises achieving at least two platelet counts of at least 50,000/μL.

3. The method of claim 1, wherein achieving a platelet count comprises achieving at least two consecutive platelet counts of at least 50,000/μL.

4. The method of claim 1, wherein achieving a platelet count comprises achieving a platelet count of at least 50,000/μL in at least 50% of platelet counts measured during the treatment period.

5. The method of claim 1, wherein the human patient has been identified as having a history of taking at least two prior ITP therapies prior to the start of the treatment period.

6. The method of claim 1, wherein the human patient had a splenectomy prior to the start of the treatment period.

7. The method of claim 1, wherein the human patient has chronic ITP.

8. The method of claim 1, wherein the human patient has relapsing ITP.

9. The method of claim 1, wherein the human patient has refractory ITP.

10. The method of claim 1, wherein the treatment period is at least 28 days.

11. The method of claim 1, comprising administering to the human patient 400 mg of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof, once a day or twice a day.

12. The method of claim 1, comprising administering to the human patient 400 mg of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof, once a day.

13. The method of claim 1, comprising administering to the human patient 400 mg of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof, twice a day.

14. The method of claim 1, comprising administering to the human patient 300 mg of at least one compound chosen from (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof, twice a day.

15. The method of claim 1, wherein the at least one compound is administered as a monotherapy.

16. The method of claim 1, wherein the at least one compound is further administered in combination with at least one concomitant ITP therapy.

17. The method of claim 16, wherein the at least one concomitant ITP therapy is chosen from corticosteroids and thrombopoietin receptor agonists.

18. The method of claim 16, wherein the at least one concomitant ITP therapy is chosen from corticosteroids, eltrombopag, and romiplostim.

19. The method of claim 1, wherein the at least one compound comprises at least one compound chosen from the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

20. The method of claim 1, wherein the at least one compound comprises at least one compound chosen from the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and pharmaceutically acceptable salts thereof.

21. The method of claim 1, wherein the at least one compound comprises a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt of the foregoing.

22. The method of claim 1, wherein the at least one compound is orally administered to the human patient.

* * * * *